(12) United States Patent
Lange et al.

(10) Patent No.: US 8,821,842 B2
(45) Date of Patent: Sep. 2, 2014

(54) ISOALKANE MIXTURE, ITS PREPARATION AND USE

(75) Inventors: Arno Lange, Bad Dürkheim (DE); Armin Ulonska, Niederkirchen (DE); Volker Wendel, Frankfurt (DE)

(73) Assignee: BASF SE (DE)

( * ) Notice: Subject to any disclaimer, the term of this patent is extended or adjusted under 35 U.S.C. 154(b) by 0 days.

(21) Appl. No.: 11/913,248

(22) PCT Filed: May 11, 2006

(86) PCT No.: PCT/EP2006/004461
§ 371 (c)(1), (2), (4) Date: Oct. 31, 2007

(87) PCT Pub. No.: WO2006/120003
PCT Pub. Date: Nov. 16, 2006

(65) Prior Publication Data
US 2008/0193404 A1    Aug. 14, 2008

(30) Foreign Application Priority Data

May 12, 2005  (DE) .......... 10 2005 022 021
Apr. 3, 2006  (EP) .............. 06007065

(51) Int. Cl.
*A61K 8/72* (2006.01)
*C07C 9/22* (2006.01)
*A61K 8/31* (2006.01)
*A61Q 5/12* (2006.01)

(52) U.S. Cl.
CPC ... *C07C 9/22* (2013.01); *A61K 8/31* (2013.01); *A61Q 5/12* (2013.01)
USPC .................................................. 424/70.11

(58) Field of Classification Search
USPC ..................................................... 424/70.11
See application file for complete search history.

(56) References Cited

U.S. PATENT DOCUMENTS

| 4,225,743 A | 9/1980 | Hoshiyama et al. |
| 4,334,113 A * | 6/1982 | Pellegrini et al. ............... 585/18 |
| 4,520,008 A | 5/1985 | Ando et al. |
| 5,525,344 A | 6/1996 | Wivell |
| 5,849,972 A | 12/1998 | Vicari et al. |
| 6,737,555 B1 | 5/2004 | Maas et al. |
| 6,852,898 B2 * | 2/2005 | Schulz et al. ................. 585/531 |
| 2001/0051686 A1 * | 12/2001 | Tabacchi et al. ............. 524/832 |
| 2003/0130550 A1 | 7/2003 | Schulz et al. |
| 2004/0181105 A1 | 9/2004 | Heidemann et al. |
| 2005/0077211 A1 | 4/2005 | Catani et al. |
| 2007/0081959 A1 * | 4/2007 | Schmid et al. ............. 424/70.11 |

FOREIGN PATENT DOCUMENTS

| DE | 2360306 A | 7/1974 |
| DE | 43 39 713 A | 5/1995 |
| DE | 10 2004 018 753 A | 11/2005 |
| EP | 1 457 475 A | 9/2004 |
| FR | 2792328 | 10/2000 |
| GB | 1286571 A | 8/1972 |
| WO | WO-95/14647 A | 6/1995 |
| WO | WO-99/25668 | 5/1999 |
| WO | WO-00/53546 A | 9/2000 |
| WO | WO-00/59849 A | 10/2000 |
| WO | WO-01/72670 | 10/2001 |
| WO | WO 2004/091555 | * 10/2004 ........... A61K 7/00 |
| WO | WO-2004/091555 A | 10/2004 |
| WO | WO-2005040312 A1 | 5/2005 |

OTHER PUBLICATIONS

Abraham et al., "Proton chemical shifts in NMR spectroscopy", J. Chem. Soc., Perkin Trans. 2, 1997, pp. 31-39.*
INEOS Oligomers, Technical Data Sheet, Isohexadecane, Sep. 2006.*
Ansaldi, A., "Aliphatic Branched Chain Hydrocarbons," *Cosmetics and Toiletries Manufacture Worldwide*, pp. 128-133.

* cited by examiner

*Primary Examiner* — Brian Gulledge
(74) *Attorney, Agent, or Firm* — Drinker Biddle & Reath LLP

(57) ABSTRACT

The present invention relates to an isoalkane mixture, to a method for its preparation and to cosmetic or pharmaceutical compositions which comprise such a mixture.

33 Claims, No Drawings

ISOALKANE MIXTURE, ITS PREPARATION AND USE

CROSS REFERENCE TO RELATED APPLICATIONS

This application is a National Phase of International Application No. PCT/EP2006/004461 filed on May 11, 2006, which in turn claims priority to Application No. 102005022021.5 filed in Germany on May 12, 2005, and to Application No. 06007065.3 filed in Europe on Apr. 3, 2006; the entire contents of which are hereby incorporated by reference.

The present invention relates to an isoalkane mixture, to a method for its preparation and to cosmetic or pharmaceutical compositions which comprise such a mixture.

Hydrocarbon mixtures which comprise short-chain olefins, e.g. having 2 to 6 carbon atoms, are obtainable on a large industrial scale. Thus, for example, the processing of petroleum by steam cracking or fluidized catalyst cracking (FCC) gives rise to a hydrocarbon mixture referred to as a $C_4$ cut and which has a high total olefin content, the olefins essentially being olefins having 4 carbon atoms. Such $C_4$ cuts, i.e. mixtures of isomeric butenes and butanes, are very well suited, if appropriate following prior removal of the isobutene and hydrogenation of the butadiene present, to the preparation of oligomers, in particular of octenes and dodecenes.

The essentially linear oligomer mixtures obtainable from olefin mixtures containing predominantly linear starting olefins have acquired great importance. They are suitable, for example, as diesel fuel component, and as intermediates in the preparation of functionalized, predominantly linear hydrocarbons. Thus, hydroformylation and subsequent hydrogenation of the olefin oligomers gives the corresponding alcohols, which are used, inter alia, as starting materials for detergents and as plasticizers. For many fields of use, e.g. as plasticizer alcohols, the degree of branching of the olefins plays a decisive role. The degree of branching is described here, for example, by the ISO index, which specifies the average number of methyl branches in the particular olefin fraction. Thus, in a $C_8$ fraction, for example, the contribution to the ISO index of the fraction by the n-octenes, methylheptenes and dimethylhexenes is 0, 1 and 2, respectively. The lower the ISO index, the greater the linearity of the molecules in the particular fraction.

It is known to use catalysts which comprise metals and predominantly nickel as active component for the preparation of slightly branched, likewise olefinically unsaturated oligomers from lower olefins. Heterogeneous catalysts here have the advantage over homogeneous ones that separating off the catalyst from the reaction product is dispensed with. Thus, for example, DE-A-43 39 713 (=WO 95/14647) discloses a method for the oligomerization of unbranched $C_2$-$C_6$-olefins over a fixed-bed catalyst at increased pressure and elevated temperature, where the catalyst comprises, as essential active constituents, 10 to 70% by weight of nickel oxide, 5 to 30% by weight of titanium dioxide and/or zirconium dioxide, 0 to 20% by weight of aluminum oxide, and silicon oxide as the remainder. Further oligomerization catalysts and methods are described, for example, in WO 99/25668, WO 00/59849, WO 00/53546, WO 01/72670 and EP-A-1 457 475.

A. Ansaldi describes, in Cosmetics and Toiletries Manufacture Worldwide, pp. 128-133, highly branched isoparaffins which are sold commercially by Presperse Inc. under the name Permethyl.

Besides water, so-called oil bodies belong to the most important raw materials for the formulation of cosmetic and pharmaceutical compositions. A broad diversity of hydrophobic components are used both as base materials and auxiliaries, and also as active ingredients. These components include, quite generally, natural fats and oils, petroleum products, such as paraffins, silicone oils, fatty alcohols, fatty acids, etc. The provision of products with a complex profile of properties often presents difficulties. Thus, there is a requirement for oil bodies for cosmetic and pharmaceutical compositions which, for example, have very good dermatological compatibility, impart a pleasant feel to the hair and the skin, have a good conditioning effect (e.g. are able to improve the feel to the touch, shine and appearance, dry and wet combability, etc.), are compatible with a large number of other active ingredients and auxiliaries and permit adjustment of the Theological properties of the compositions in a wide range (e.g. from liquid to gel-like). Additionally, many consumers increasingly desire products which have only a discreet odor or are completely free from perfume substances.

DE 10 2004 018 753 A1 describes a method for the preparation of a $C_{16}$-alkane mixture in which a butene-containing $C_4$-hydrocarbon stream is oligomerized in the presence of a nickel-containing catalyst, then the $C_{16}$-olefin fraction is separated off and the separated-off $C_{16}$-fraction is hydrogenated. Also described are $C_{16}$-alkane mixtures which have a fraction of $C_{16}$-alkanes of ≥95% by mass, and their use. A use in cosmetics is also mentioned here quite generally, without information regarding formulation or support by a working example.

DE-OS 2360306 describes an oil for cosmetic purposes which is obtainable by:
1. polymerization of isobutene or an isobutene-containing $C_4$-olefin mixture in the presence of a Friedel-Crafts catalyst,
2. distillation,
3. hydrogenation and
4. steam distillation for deodorization.

WO 2004/091555 describes a cosmetic composition which comprises at least one branched α-olefin or a hydrogenation product thereof. Here, the α-olefin has at least one $C_2$- or longer-chain alkyl branch and is obtainable by oligomerization of certain linear or branched α-olefins in the presence of an acidic catalyst. A disadvantage of these products is their high degree of branching, their content of tert-butyl groups and their nonuniformity, meaning that the profile of properties achieved therewith is still in need of improvement for use in cosmetic and pharmaceutical formulations. Thus, the oligomers used, for example, have a marked intrinsic odor reminiscent of terpenes.

The object of the present invention is to provide saturated hydrocarbons which are suitable in an advantageous manner as oil bodies for cosmetic and pharmaceutical compositions. In particular, they should be suitable for the preparation of products which essentially have no intrinsic odor attributable to the oil body.

Surprisingly, it has now been found that this object is achieved by an isoalkane mixture with an average degree of branching.

The invention therefore provides an isoalkane mixture whose $^1$H NMR spectrum in the region of a chemical shift δ of from 0.6 to 1.0 ppm, based on tetramethylsilane, has a surface integral of from 25 to 70%, based on the total integral surface.

Preference is given to isoalkane mixtures whose $^1$H NMR spectrum in the region of a chemical shift δ of from 0.6 to 1.0 ppm, has a surface integral of from 30 to 60%, preferably from 35 to 55%, based on the total integral surface.

Preferably, the isoalkane mixtures according to the invention have no olefinic double bonds. Suitable isoalkane mixtures have, in the $^1$H NMR spectrum in the region of a chemical shift δ of from 4 to 6 ppm, no signals which are attributable to olefin protons.

Furthermore, the isoalkane mixture preferably has, in the $^1$H NMR spectrum in the region of a chemical shift δ of from 0.5 to 3 ppm (i.e. in the region of the aliphatic protons), a surface integral of up to 95%, particularly preferably of up to 98%, based on the total integral surface.

The isoalkane mixtures according to the invention essentially have no tert-butyl groups (—C(CH$_3$)$_3$). The fraction of terminal tert-butyl groups is preferably at most 20%, particularly preferably at most 10%, in particular at most 5% and specifically at most 2%.

Preferably, the isoalkanes according to the invention have a uniform structure. Thus, based on the longest continuous carbon chain, they had essentially or exclusively methyl branches. The fraction of side chains with alkyl groups which have 2 or more than two carbon atoms is less than 20%, preferably at most 10%, particularly preferably at most 5%, in particular at most 1%, based on the total number of branching sites.

Preferably, the isoalkane mixtures comprise at least 70% by weight, preferably at least 85% by weight, in particular at least 95% by weight, of alkanes having 8 to 20 carbon atoms.

Preferably, the isoalkane mixtures comprise at least 70% by weight, preferably at least 80% by weight, in particular at least 90% by weight (such as, for example, at least 94% by weight), of alkanes having 12 to 20 carbon atoms.

The alkane mixture according to the invention preferably comprises at least 70% by weight, preferably at least 85% by weight, in particular at least 95% by weight, of alkanes with an even number of carbon atoms. A specific embodiment is an isoalkane mixture which consists essentially of alkanes having 8 or 12 or 16 carbon atoms.

The isoalkane mixtures according to the invention (and obtainable by the method described below) preferably have an oligomeric distribution, i.e. nonuniformity with regard to the number of carbon atoms (and thus the molecular weight) of the alkanes present. Preferably, the isoalkane mixtures according to the invention comprise, based on their total weight, less than 95% by weight, particularly preferably at most 90% by weight, of alkanes of the same molecular weight. Such nonuniform isoalkane mixtures can have particularly advantageous application properties, specifically for use in cosmetic compositions. These include, specifically, the rheological properties of the isoalkane mixtures according to the invention, such as the spreading behavior. Thus, the relative spreading values of the isoalkane mixtures according to the invention (based on Paraffinum perliquidum as standard) are at least 130%, particularly preferably at least 140%, in particular at least 150%. They thus surpass the oil bodies used customarily from the prior art and in particular isohexadecane (C$_{16}$-isoalkane, and mixtures with very high C$_{16}$-isoalkane content, e.g. according to DE 10 2004 018 753).

The isoalkane mixtures according to the invention and obtainable by the method according to the invention preferably have a viscosity, determined in accordance with Brookfield, in the range from 2 to 10 mPas, particularly preferably in the range from 4 to 8 mPas. The kinematic viscosity is preferably in the range from 5 to 25 cSt, particularly preferably in the range from 10 to 20 cSt.

In addition, the isoalkane mixtures according to the invention are particularly advantageously suitable for the preparation of stable emulsions, in particular stable cosmetic emulsions.

The isoalkane mixtures according to the invention and obtainable by the method according to the invention preferably have a density in the range from 0.7 to 0.82 g/cm$^3$, particularly preferably in the range from 0.75 to 0.8 g/cm$^3$.

The isoalkane mixtures according to the invention and obtainable by the method according to the invention preferably have a refractive index in the range from 1.4 to 1.5.

The isoalkane mixtures according to the invention preferably have a degree of branching B in the range from 0.1 to 0.35, particularly preferably 0.12 to 0.3, in particular 0.15 to 0.27 and specifically 0.17 to 0.23.

For the purposes of the present invention, the degree of branching B is independent of molecular weight and defined as the number of branches per carbon atom (B=number of branches/number of carbon atoms, e.g. n-octane: 0/8=0, methylheptane: 1/8=0.125, dimethylhexane: 2/8=0.25, squalane: 6/30=0.2.

The isoalkane mixtures according to the invention are preferably not pure substances and/or natural products. In particular, the isoalkane mixtures according to the invention do not consist of squalane (2,6,10,15,19,23-hexamethyltetracosane) and in particular do not comprise it either. However, the isoalkane mixtures according to the invention are suitable in an advantageous way as substitute for squalane. Squalane is a high-value native oil which is obtained, for example, from shark liver. Being a natural product, it is available only in restricted amounts and, for reasons of species protection, there is a great need for a suitable replacement. Although the isoalkane mixtures according to the invention, on the evidence of their $^1$H NMR spectrum, differ significantly in structural terms from squalane, they have a similar degree of branching and are suitable in an advantageous way as replacement.

Suitable isoalkane mixtures are obtainable by a method in which a) a hydrocarbon feed material is provided which comprises at least one olefin having 2 to 6 carbon atoms, b) the hydrocarbon feed material is subjected to an oligomerization over a transition-metal-containing catalyst, c) the oligomerization product obtained in step b) is completely hydrogenated.

This method is likewise provided by the invention.

Step a)

Suitable olefin feed materials for step a) are in principle all compounds which comprise 2 to 6 carbon atoms and at least one ethylenically unsaturated double bond.

Preferably, in step a), an industrially available olefin-containing hydrocarbon mixture is used.

Preferred industrially available olefin mixtures result from the hydrocarbon cleavage during petroleum processing, for example by catalytic cracking, such as fluid catalytic cracking (FCC), thermocracking or hydrocracking with subsequent dehydrogenation. A preferred industrial olefin mixture is the C$_4$ cut. C$_4$ cuts are obtainable, for example, by fluid catalytic cracking or steam cracking of gas oil or by steam cracking of naphtha. Depending on the composition of the C$_4$ cut, a distinction is made between the whole C$_4$ cut (crude C$_4$ cut), so-called raffinate I obtained after separating off 1,3-butadiene, and raffinate II obtained after separating off isobutene. A further suitable industrial olefin mixture is the C$_5$ cut obtainable during the cleavage of naphtha. Olefin-containing hydrocarbon mixtures having 4 to 6 carbon atoms suitable for use in step a) can also be obtained by catalytic dehydrogenation of suitable industrially available paraffin mixtures. Thus, the preparation of C$_4$-olefin mixtures is possible, for example, from liquid gases (liquefied petroleum gas, LPG) and liquefiable natural gases (liquefied natural gas, LNG). Besides the LPG fraction, the latter also additionally comprise relatively large amounts of higher molecular weight hydrocarbons (light naphtha) and are thus also suitable for the preparation of $C_5$- and $C_6$-olefin mixtures. The preparation of olefin-containing hydrocarbon mixtures which comprise monoolefins having 4 to 6 carbon atoms from LPG or LNG streams is possible by customary methods known to the person skilled in the art which, besides dehydrogenation, usually also comprise one or more work-up steps. These include, for example, separating off at least some of the saturated hydrocarbons present in the abovementioned olefin feed mixtures. These can be reused, for example, for the preparation of olefin feed materials by cracking and/or dehydrogenation. The olefins used in step a), however, may also comprise a fraction of saturated hydrocarbons which behave inertly toward the oligomerization conditions. The fraction of these saturated components is generally at most 60% by weight, preferably at most 40% by weight, particularly preferably at most 20% by weight, based on the total amount of the olefins and saturated hydrocarbons present in the hydrocarbon feed material.

Preferably, in step a), a hydrocarbon mixture is provided which comprises 20 to 100% by weight of $C_4$-olefins, 0 to 80% by weight of $C_5$-olefins, 0 to 60% by weight of $C_6$-olefins and 0 to 10% by weight of olefins different from the abovementioned olefins, in each case based on the total olefin content.

Preferably, in step a), a hydrocarbon mixture is provided which has a content of linear monoolefins of at least 80% by weight, particularly preferably at least 90% by weight and in particular at least 95% by weight, based on the total olefin content. Here, the linear monoolefins are selected from 1-butene, 2-butene, 1-pentene, 2-pentene, 1-hexene, 2-hexene, 3-hexene and mixtures thereof. To establish the desired degree of branching of the isoalkane mixture, it may be advantageous if the hydrocarbon mixture used in step a) comprises up to 20% by weight, preferably up to 5% by weight, in particular up to 3% by weight, of branched olefins, based on the total olefin content.

In step a), a $C_4$-hydrocarbon mixture is particularly preferably provided.

The butene content, based on 1-butene, 2-butene and isobutene, of the $C_4$-hydrocarbon mixture provided in step a) is preferably 10 to 100% by weight, particularly preferably 50 to 99% by weight, and in particular 70 to 95% by weight, based on the total olefin content. Preferably, the ratio of 1-butene to 2-butene is in a range from 20:1 to 1:2, in particular about 10:1 to 1:1. Preferably, the $C_4$-hydrocarbon mixture used in step a) comprises less than 5% by weight, in particular less than 3% by weight, of isobutene.

The provision of the olefin-containing hydrocarbons in step a) can comprise separating off branched olefins. Of suitability are customary separation methods known from the prior art which are based on differing physical properties of linear and branched olefins or on differing reactivities, which permit selective reactions. Thus, for example, isobutene can be separated off from $C_4$-olefin mixtures, such as raffinate 1, by one of the following methods:

Molecular sieve separation,
fractional distillation,
reversible hydration to tert-butanol,
acid-catalyzed alcohol addition onto a tertiary ether, e.g. methanol addition to methyl tert-butyl ether (MTBE),
irreversible catalyzed oligomerization to di- and tri-isobutene,
irreversible polymerization to polyisobutene.

Such methods are described in K. Weissermel, H.-J. Arpe, Industrielle organische Chemie [Industrial Organic Chemistry], 4th edition, pp. 76-81, VCH-Verlagsgesellschaft Weinheim, 1994, to which reference is hereby made in its entirety.

Preferably, in step a), a raffinate II is provided.

A raffinate II suitable for use in the method according to the invention has, for example, the following composition:
0.5 to 5% by weight of isobutane,
5 to 20% by weight of n-butane,
20 to 40% by weight of trans-2-butene,
10 to 20% by weight of cis-2-butene,
25 to 55% by weight of 1-butene,
0.5 to 5% by weight of isobutene
and traces of gases, such as 1,3-butadiene, propene, propane, cyclopropane, propadiene, methylcyclopropane, vinylacetylene, pentenes, pentanes etc. in the region of in each case at most 1% by weight.

A suitable raffinate II has the following typical composition:

| | |
|---|---|
| iso-, n-butane | 26% by weight |
| isobutene | 1% by weight |
| 1-butene | 26% by weight |
| trans-2-butene | 31% by weight |
| cis-2-butene | 16% by weight |

If diolefins or alkynes are present in the olefin-rich hydrocarbon mixture, then these can be removed from same to preferably less than 10 ppm by weight prior to the oligomerization. They are preferably removed by selective hydrogenation, e.g. as in EP-81 041 and DE-15 68 542, particularly preferably by a selective hydrogenation to a residual content of below 5 ppm by weight, in particular 1 ppm by weight.

Expediently, oxygen-containing compounds, such as alcohols, aldehydes, ketones or ethers, are furthermore largely removed from the olefin-rich hydrocarbon mixture. For this, the olefin-rich hydrocarbon mixture can advantageously be passed over an adsorbent, such as, for example, a molecular sieve, in particular one with a pore diameter of >4 Å to 5 Å. The concentration of oxygen-containing, sulfur-containing, nitrogen-containing and halogen-containing compounds in the olefin-rich hydrocarbon mixture is preferably less than 1 ppm by weight, in particular less than 0.5 ppm by weight.

Step b)

For the purposes of the present invention, the term "oligomers" comprises dimers, trimers, tetramers and higher products from the synthesis reaction of the olefins used. Preferably, the oligomers obtained in step b) are selected from dimers, trimers and tetramers. The oligomers are for their part olefinically unsaturated. The desired isoalkanes can be obtained through appropriate choice of the hydrocarbon feed material and the oligomerization catalyst used for the oligomerization, as described below.

For the oligomerization in step b), a reaction system can be used which comprises one or more, identical or different reactors. In the simplest case, a single reactor is used for the oligomerization in step b). However, it is also possible to use a plurality of reactors which in each case have identical or different mixing characteristics. The individual reactors can, if desired, be divided one or more times by internals. If two or more reactors form the reaction system, then these can be connected with one another as desired, e.g. in parallel or in series. In one suitable embodiment, for example, a reaction system is used which consists of two reactors connected in series.

Suitable pressure-resistant reaction apparatuses for the oligomerization are known to the person skilled in the art. These include the generally customary reactors for gas-solid and gas-liquid reactions, such as, for example, tubular reactors, stirred-tank reactors, gas circulation reactors, bubble columns etc., which may, if appropriate, be divided by internals. Preferably, tube-bundle reactors or shaft furnaces are used. If, for the oligomerization, a heterogeneous catalyst is used, then this can be arranged in a single or in a plurality of catalyst fixed beds. In this connection, it is possible to use different catalysts in different reaction zones. However, preference is given to using the same catalyst in all reaction zones.

The temperature during the oligomerization reaction is generally in a range from about 20 to 280° C., preferably from 25 to 200° C., in particular from 30 to 140° C. The pressure during the oligomerization is generally in a range from about 1 to 300 bar, preferably from 5 to 100 bar and in particular from 20 to 70 bar. If the reaction system comprises more than one reactor, then these may have identical or different temperatures and identical or different pressures. Thus, for example, in the second reactor of a reactor cascade, a higher temperature and/or a higher pressure than in the first reactor can be set, e.g. in order to achieve as complete a conversion as possible.

In a specific embodiment, the temperature and pressure values used for the oligomerization are selected so that the olefin-containing feed material is in the form of a liquid or is present in the supercritical state.

The reaction in step b) is preferably carried out adiabatically. For the purposes of the present invention, this term is to be understood in the industrial sense and not in the physicochemical sense. Thus, the oligomerization reaction generally proceeds exothermally, meaning that the reaction mixture, upon flowing through the reaction system, for example a catalyst bed, experiences a temperature increase. Under adiabatic reaction control is understood as meaning a procedure in which the amount of heat liberated in an exothermic reaction is absorbed by the reaction mixture in the reactor and no cooling by cooling devices is applied. The heat of the reaction is thus dissipated with the reaction mixture from the reactor, apart from a residual amount which is released through natural thermal conduction and thermal radiation from the reactor to the surroundings.

For the oligomerization in step b), a catalyst containing transition metal is used. These are preferably heterogeneous catalysts. Preferred catalysts which known a low oligomer branching nickel-comprising catalysts for the reaction in step a), which as are known bring about low oligomer branching, are generally known to the person skilled in the art. These include the catalysts described in Catalysis Today, 6, 329 (1990), in particular pages 336-338, and the catalysts described in DE-A-43 39 713 (=WO-A 95/14647) and DE-A-199 57 173, to which reference is hereby expressly made. A suitable oligomerization process in which the feed stream used for the oligomerization is divided and passed to at least two reaction zones operated at different temperatures is described in EP-A-1 457 475, to which reference is likewise made.

The heterogeneous nickel-comprising catalysts used can have different structures. In principle, unsupported catalysts and also supported catalysts are suitable. The latter are preferably used. The carrier materials may be, for example, silica, clay earth, aluminosilicates, aluminosilicates with layer structures and zeolites, such as mordenite, faujasite, zeolite X, zeolite Y and ZSM-5, zirconium oxide, which is treated with acids, or sulfated titanium dioxide. Of particular suitability are precipitation catalysts which are obtainable by mixing aqueous solutions of nickel salts and silicates, e.g. sodium silicate with nickel nitrate, and, if appropriate, aluminum salts, such as aluminum nitrate, and calcination. It is also possible to use catalysts which are obtained through intercalation of $Ni^{2+}$ ions by ion exchange into natural or synthetic sheet silicates, such as montmorillonites. Suitable catalysts can also be obtained by impregnation of silica, clay earth or alumosilicates with aqueous solutions of soluble nickel salts, such as nickel nitrate, nickel sulfate or nickel chloride, and subsequent calcination.

Catalysts comprising nickel oxide are preferred. Particular preference is given to catalysts which consist essentially of NiO, $SiO_2$, $TiO_2$ and/or $ZrO_2$, and, if appropriate, $Al_2O_3$. Most preference is given to a catalyst which comprises, as essential active constituents, 10 to 70% by weight of nickel oxide, 5 to 30% by weight of titanium dioxide and/or zirconium dioxide, 0 to 20% by weight of aluminum oxide and, as the remainder, silicon dioxide. Such a catalyst is obtainable by precipitation of the catalyst mass at pH 5 to 9 by adding an aqueous solution comprising nickel nitrate to give an alkali waterglass solution which comprises titanium dioxide and/or zirconium dioxide, filtration, drying and heat-treatment at 350 to 650° C. For the preparation of these catalysts, reference is made specifically to DE-43 39 713. Reference is made to the disclosure of this specification and the prior art cited therein in their entirety.

In a further embodiment, the catalyst used in step b) is a nickel catalyst as in DE-A-199 57 173. This is essentially aluminum oxide which has been supplied with a nickel compound and a sulfur compound. Preferably, a molar ratio of sulfur to nickel in the range from 0.25:1 to 0.38:1 is present in the finished catalyst.

The catalyst is preferably in piece form, e.g. in the form of tablets, e.g. having a diameter of from 2 to 6 mm and a height of from 3 to 5 mm, rings with, for example, an outer diameter of from 5 to 7 mm, a height of from 2 to 5 mm and a hole diameter from 2 to 3 mm, or strands of varying length with a diameter of, for example, 1.5 to 5 mm. Such forms are obtained in a manner known per se by tableting or extrusion, mostly using a tableting auxiliary, such as graphite or stearic acid.

Step c)

In step c), the hydrogenation catalysts which can be used are usually all catalysts of the prior art which catalyze the hydrogenation of olefins to the corresponding alkanes. The catalysts can be used either in heterogeneous phase or as homogeneous catalysts. Preferably, the hydrogenation catalysts comprise at least one metal of group VIII.

Particularly suitable metals of group VIII are chosen from ruthenium, cobalt, rhodium, nickel, palladium and platinum.

The metals can also be used as mixtures. Furthermore, besides the metals of group VIII, the catalysts can also comprise small amounts of further metals, for example metals of group VIIa, in particular rhenium, or metals of group Ib, i.e. copper, silver or gold. Particularly preferred metals of group VIII are ruthenium, nickel, palladium and platinum, in particular platinum, nickel and palladium, and more preferably palladium and nickel. Specifically, the catalyst comprises palladium as catalytically active species.

If a heterogeneous catalyst is used, then this is suitably in finely divided form. The finely divided form is achieved, for example, as follows:

Black catalyst: the metal is reductively deposited from the solution of one of its salts shortly prior to use as catalyst.

Adams catalyst: the metal oxides, in particular the oxides of platinum and palladium, are reduced in situ by the hydrogen used for the hydrogenation.

Skeleton or Raney catalyst: the catalyst is prepared as "metal sponge" from a binary alloy of the metal (in particular nickel or cobalt) with aluminum or silicon by leaching out one partner with acid or alkali. Remains of the original alloy partner often have a synergistic effect.

Supported catalyst: black catalysts can also be precipitated on the surface of a support substance. Suitable supports and support materials are described below.

Such heterogeneous catalysts are described in general form, for example, in Organikum, 17th edition, VEB Deutscher Verlag der Wissenschaften, Berlin, 1988, p. 288. Furthermore, heterogeneous hydrogenation catalysts which are suitable for the reduction of olefins to alkanes are described in more detail in the following specifications:

U.S. Pat. No. 3,597,489, U.S. Pat. No. 2,898,387 and GB 799,396 describe the hydrogenation of benzene to cyclohexane over nickel and platinum catalysts in the gas or liquid phase. GB 1,155,539 describes the use of a nickel catalyst doped with rhenium for the hydrogenation of benzene. U.S. Pat. No. 3,202,723 describes the hydrogenation of benzene with Raney nickel. Ruthenium-containing suspension catalysts which are doped with palladium, platinum or rhodium are used in SU 319582 for the hydrogenation of benzene to cyclohexane. Aluminum oxide-supported catalysts are described in U.S. Pat. No. 3,917,540 and U.S. Pat. No. 3,244,644. Reference is made to the hydrogenation catalysts described in these specifications in their entirety.

Depending on the version of the hydrogenation method, the support material can have various forms. If the hydrogenation is carried out in the liquid-phase procedure, then the support material is generally used in the form of a finely divided powder. By contrast, if the catalyst is used in the form of a fixed-bed catalyst, then moldings, for example, are used as support material. Such moldings can be in the form of spheres, tablets, cylinders, hollow cylinders, Raschig rings, strands, saddle packings, stars, spirals, etc. with a size (measurement of the longest expanse) of from about 1 to 30 mm. Furthermore, the supports can be in the form of monoliths, as are described, for example, in DE-A-19642770. Furthermore, the supports can be used in the form of wires, sheets, grids, meshes, fabrics and the like.

The supports can consist of metallic or nonmetallic, porous or nonporous material.

Suitable metallic materials are, for example, high-alloy stainless steels. Suitable nonmetallic materials are, for example, mineral materials, e.g. natural and synthetic minerals, glasses or ceramics, plastics, e.g. synthetic or natural polymers, or a combination of the two.

Preferred support materials are carbon, in particular activated carbon, silicon dioxide, in particular amorphous silicon dioxide, aluminum oxide, and furthermore the sulfates and carbonates of the alkaline earth metals, calcium carbonate, calcium sulfate, magnesium carbonate, magnesium sulfate, barium carbonate and barium sulfate.

The catalyst can be applied to the support by customary methods, e.g. by impregnation, wetting or spraying the support with a solution which comprises the catalyst or a suitable precursor thereof.

Suitable supports and methods of applying the catalyst to these are described, for example, in DE-A-10128242, to which reference is hereby made in its entirety.

Homogeneous hydrogenation catalysts can also be used in the method according to the invention. Examples thereof are the nickel catalysts which are described in EP-A-0668257. A disadvantage of using homogeneous catalysts, however, is their production costs and also the fact that they cannot usually be regenerated.

Therefore, in the method according to the invention, heterogeneous hydrogenation catalysts are preferably used.

The heterogeneous catalysts used in the method according to the invention particularly preferably comprise at least one metal from subgroup VIII which is selected from ruthenium, nickel, cobalt, palladium and platinum, and which is, if appropriate, doped with a further transition metal, in particular with one from subgroup VIIa, Ib or IId and in particular with rhenium.

The metal is particularly preferably used in supported form or as metal sponge. Examples of supported catalysts are, in particular, palladium, nickel or ruthenium on carbon, in particular activated carbon, silicon dioxide, in particular on amorphous silicon dioxide, barium carbonate, calcium carbonate, magnesium carbonate or aluminum oxide, where the supports may be present in the forms described above. Preferred support forms are the moldings described above.

The metallic catalysts can also be used in the form of their oxides, in particular palladium oxide, platinum oxide or nickel oxide, which are then reduced to the corresponding metals under the hydrogenation conditions.

As metal sponge, Raney nickel in particular is used.

Specifically, use is made in the method according to the invention of palladium on support materials, such as activated carbon, as hydrogenation catalyst.

The amount of catalyst to be used depends inter alia on the particular catalytically active metal and on its use form and can be determined in a particular case by the person skilled in the art. Thus, for example, a nickel- or cobalt-containing hydrogenation catalyst is used in an amount of preferably from 0.5 to 70% by weight, particularly preferably from 1 to 20% by weight and in particular from 2 to 10% by weight, based on the weight of the oligomerization product to be hydrogenated. The stated amount of catalyst refers here to the amount of active metal, i.e. to the catalytically effective component of the catalyst. When using precious metal catalysts which comprise, for example, platinum or palladium, the values are about a factor of 10 smaller.

The hydrogenation takes place at a temperature of from preferably 20 to 250° C., particularly preferably from 50 to 240° C. and in particular from 150 to 220° C.

The reaction pressure of the hydrogenation reaction is preferably in the range from 1 to 300 bar, particularly preferably from 50 to 250 bar and in particular from 150 to 230 bar.

Both reaction pressure and reaction temperature depend, inter alia, on the activity and amount of the hydrogenation catalyst used and can be determined in a particular case by the person skilled in the art.

If desired, the oligomerization product can be hydrogenated several times ("after hydrogenated") to achieve as complete a hydrogenation as possible. In this connection, as soon as hydrogen consumption can no longer be established, further hydrogen is injected. Preferably, before injecting hydrogen, fresh catalyst is firstly added.

The hydrogenation can in a suitable solvent or preferably without a diluent preferably. Suitable solvents are those which are inert under the reaction conditions, i.e. neither react with the starting material or product, nor are themselves changed, and which can be separated off from the resulting isoalkanes without problems. Suitable solvents include open-chain and cyclic ethers, such as diethyl ether, methyl tert-butyl ether, tetrahydrofuran or 1,4-dioxane and alcohols, in particular $C_1$-$C_3$-alkanols, such as methanol, ethanol, n-propanol or isopropanol. Also suitable are mixtures of the above-mentioned solvents.

The hydrogen required for the hydrogenation can be used either in pure form or in the form of hydrogen-containing gas mixtures. However, the latter must comprise no harmful amounts of catalyst poisons, such as CO. Examples of suitable hydrogen-containing gas mixtures are those from the reforming process. However, preference is given to using hydrogen in pure form.

The hydrogenation can be configured either continuously or discontinuously.

The hydrogenation is usually carried out such that the oligomerization product, if appropriate in a solvent, is initially introduced. This reaction solution is then preferably firstly admixed with the hydrogenation catalyst before the introduction of hydrogen starts. Depending on the hydrogenation catalyst used, the hydrogenation takes place at elevated temperature and/or at increased pressure. For carrying out the reaction under pressure, the customary pressurized vessels known from the prior art, such as autoclaves, stirred autoclaves and pressurized reactors, can be used. If a superatmospheric hydrogen pressure is not used, then the customary reaction devices of the prior art which are suitable for atmospheric pressure are contemplated. Examples thereof are customary stirred vessels, which are preferably equipped with evaporative cooling, suitable mixers, feed devices, if appropriate heat exchanger elements and inertization devices. If the reaction is carried out continuously, the hydrogenation can be carried out under atmospheric pressure in reaction vessels, tubular reactors, fixed-bed reactors and the like customary for this purpose.

When the hydrogenation is complete, the catalyst and the solvent are usually removed. The heterogeneous catalyst is preferably separated off by filtration or by sedimentation and removal of the upper, product-containing phase. Other separation methods for removing solids from solutions, such as, for example, centrifugation, are also suitable for removing the heterogeneous catalyst. Homogeneous catalysts are removed by customary methods for the separation of equiphasal mixtures, for example by chromatographic methods. If appropriate, it may be necessary, depending on the type of catalyst, to deactivate it prior to the removal. This can be carried out by customary methods, for example by washing the reaction solution with protic solvents, e.g. with water or with $C_1$-$C_3$-alkanols, such as methanol, ethanol, propanol or isopropanol, which are, if required, rendered basic or acidic.

The solvent is removed by customary methods, for example by distillation, in particular under reduced pressure.

In a specific embodiment of the method according to the invention, the oligomerization product obtained in step b) and/or the hydrogenation product obtained in step c) are/is subjected to a separation. Here, at least one fraction enriched in one specific oligomer, or hydrogenated oligomers, is obtained. Thus, for example, a $C_4$-hydrocarbon mixture can in step b) be subjected to an oligomerization and then, before the hydrogenation, be subjected to a separation, where at least one fraction enriched in $C_8$-, $C_{12}$- or $C_{16}$-oligomers is obtained. This (these) oligomer-enriched fraction(s) is/are then used for the hydrogenation. It is equally possible for an oligomer mixture from step b) to firstly be hydrogenated without separation and then for the product mixture of hydrogenation to be subjected to separation, where, for example when using a $C_4$ hydrocarbon mixture for the oligomerization, at least one fraction enriched in $C_8$—, $C_{12}$- or $C_{16}$-isoalkanes is obtained. The fractions enriched in one of the abovementioned alkanes comprise, in a preferred embodiment, as stated at the beginning, further alkanes different therefrom. These are preferably essentially alkanes with a higher molecular weight than the enriched alkane. Preferably, then, for example, a fraction enriched in $C_{16}$-isoalkanes is obtained which essentially comprises no $C_8$— and/or $C_{12}$-isoalkanes, but which comprises $C_{20}$-isoalkanes and, if appropriate, higher homologs.

For the separation, the reaction mixture of the oligomerization or of the hydrogenation can be subjected to one or more separation steps. Suitable separation devices are the customary apparatuses known to the person skilled in the art. These include, for example, distillation columns, e.g. plate columns, which may, if desired, be equipped with bubble caps, sieve plates, sieve trays, valves, side take-offs, etc., evaporators, such as thin-film evaporators, falling-film evaporators, wiper-blade evaporators, Sambay evaporators, etc. and combinations thereof. Isolation of the olefin fraction preferably takes place by single-stage or multistage fractional distillation.

The isoalkane mixtures according to the invention are particularly advantageously suitable for use in cosmetic and pharmaceutical compositions. They are generally odorless and in particular have no odor components perceived by the consumer of cosmetic and pharmaceutical formulations as "strange" or "chemical", e.g. a terpene-like odor, which requires the use of intensively fragrant or relatively large quantities of perfume oils for masking.

Although the isoalkane mixtures according to the invention have no intrinsic odor as such, it may be advantageous to subject the hydrogenated oligomerization product obtained in step c) to at least one work-up step to remove undesired components.

These include, for example, components which possibly still adversely affect the optical and/or olfactory properties. Preferably, the hydrogenated oligomerization product obtained in step c) is subjected to a work-up by bringing it into contact with at least one adsorbent. Suitable adsorbents are described, for example, in Ullmann's Encyclopedia of Industrial Chemistry, 6th Edition, 2000 Electronic Release, "Adsorption", 3. Absorbents and the corresponding tables 1 and 2, to which reference is made here in its entirety.

The adsorbents are preferably selected from silicone dioxides, kieselguhr, natural and synthetic aluminum silicates, aluminum oxides, solids containing aluminum oxide, aluminum phosphates, phosphates different from aluminum phosphates, titanium dioxides, zirconium dioxides, adsorbents containing carbon, organic absorber resins and mixtures thereof.

Suitable adsorbents are, for example, active aluminum oxides. They are prepared, for example, starting from aluminum hydroxide, which is obtainable by customary precipitation methods from aluminum salt solutions. Active aluminum oxides suitable for the method according to the invention are also obtainable starting from aluminum hydroxide gels. To prepare such gels, precipitated aluminum hydroxide, for example, can be activated by customary work-up steps, such as filtration, washing and drying, and then, if appropriate, be ground or agglomerated. If desired, the resulting aluminum oxide can then also be subjected to a shaping method, such as extrusion, granulation, tableting etc. Suitable adsorbents are preferably the Selexsorb™ grades from Alcoa.

Suitable adsorbents are furthermore solids containing aluminum oxide. These include, for example, the so-called clay earths, which likewise have aluminum oxides as main constituent. Natural and synthetic aluminum silicates are also suitable. These include sheet silicates, such as clay minerals, and particularly preferably tectosilicates, specifically zeolites.

Furthermore, suitable adsorbents are aluminum phosphates.

Further suitable adsorbents are silicon dioxides, which are obtainable, for example, by dewatering and activating silica gels. A further method of producing silicon dioxide is the flame hydrolysis of silicon tetrachloride, where, through appropriate variations of the reaction parameters, such as, for example, the stoichiometric composition of the starting mixture and the temperature, the desired surface properties of the resulting silicon dioxide can be varied within wide ranges.

Further suitable adsorbents are kieselguhrs, which likewise have silicon dioxides as main constituent. These include, for example, the diatomaceous earth obtained from silica sediments.

Further suitable adsorbents are titanium dioxides and zirconium dioxides, as are described, for example, in Römpp, Chemie Lexikon, 9th edition (Paperback), Vol. 6, p. 4629ff. and p. 5156ff. and the literature cited therein. Reference is made to this in its entirety.

Further suitable adsorbents are phosphates, in particular condensed phosphates, such as, for example, melt phosphates or high-temperature phosphates, which have a large active surface area. Suitable phosphates are described, for example, in Römpp, Chemie Lexikon, 9th edition (Paperback), Vol. 4, p. 3376ff. and the literature cited therein. Reference is made here to this in its entirety.

Further suitable adsorbents are carbon-containing adsorbents, preferably activated carbon. Activated carbon is generally understood here as meaning carbon with a porous structure and high internal surface area. To produce activated carbon, vegetable, animal and/or mineral carbon-containing raw materials are heated, e.g. with dehydrating agents, such as zinc chloride or phosphoric acid, or are carbonized by dry distillation and then oxidatively activated. For this, the carbonized material can, for example, be treated at elevated temperatures of from about 700 to 1000° C. with steam, carbon dioxide and/or mixtures thereof.

It is also possible to use ion exchangers and/or adsorber resins.

The adsorbents generally have a specific surface area, determined according to BET, in the range from about 10 to 2000 $m^2/g$, in particular in the range from 10 to 1500 $m^2/g$ and specifically in the range from 20 to 600 $m^2/g$.

The isoalkane mixtures according to the invention are furthermore generally colorless or have only a slight intrinsic color. Preferably, the isoalkane mixtures according to the invention and obtainable by the method according to the invention have a Hazen or APHA color number (determined in accordance with DIN 6271) of at most 6, particularly preferably of at most 5. Depending on the molecular weight, the isoalkanes are of liquid to oil-like consistency. For a use in cosmetic and pharmaceutical compositions, preference is given to using isoalkane mixtures which have isoalkanes having 8 to 28, preferably 8 to 20, carbon atoms. These isoalkane mixtures are liquid under standard conditions (25° C., 1013 mbar).

In a specific embodiment, isoalkane mixtures which have a high uniformity with regard to the molecular weight of the isoalkanes present are used in cosmetic and pharmaceutical compositions. These are preferably dimers, trimers or tetramers. These isoalkane mixtures have then preferably at least 70% by weight, particularly preferably at least 85% by weight and in particular at least 95% isoalkanes with the same number of carbon atoms.

Compared to the oil bodies known from the prior art for cosmetic and pharmaceutical compositions, the isoalkanes according to the invention are characterized by comparable or better application properties. For example, they have excellent skin compatibility, do not lead to irritations and are suitable for alleviating the irritating effect of other ingredients or for improving the dermal application of active ingredients. They can be formulated with a large number of cosmetic active ingredients and auxiliaries. In this connection, they usually have a lower volatility than corresponding silicone oils of the same molecular weight. Their flame points are sufficiently high to satisfy stringent safety standards during production and use. Thus, for example, a $C_{16}$-isoalkane mixture according to the invention generally has a flame point of at least 100° C., such as, for example, of 105° C. Furthermore, the isoalkane mixtures according to the invention have excellent sensory properties. They leave behind a good feel on the skin, absorb readily on keratin surfaces and impart good combability to hair treated therewith. They are thus suitable in a particularly advantageous way for partially or completely replacing other hydrophobic components of cosmetic and pharmaceutical compositions, in particular silicone oils and mineral oils.

Besides the isoalkane mixtures according to the invention and obtainable according to the inventive method, isoalkane mixtures which have a very high fraction of alkanes of the same molecular weight are also suitable for use in cosmetic or pharmaceutical compositions. These include isoalkane mixtures which have greater than or equal to 95% by weight, preferably at least 96% by weight, in particular at least 97% by weight, of alkanes of the same molecular weight. These are preferably $C_{16}$-isoalkane mixtures (referred to below as "high $C_{16}$-containing isoalkane mixtures"). The invention therefore further provides a cosmetic or pharmaceutical composition which comprises at least one mixture having $C_{16}$-alkanes, where the mixture has a fraction of $C_{16}$-alkanes of greater than or equal to 95% by weight. Preferably, the cosmetic or pharmaceutical compositions then comprise a mixture having $C_{16}$-alkanes wherein the mixture has a composition in which the molecules present comprise, on average, fewer than 1.0 quaternary carbon atoms per molecule, where the mixture has a fraction of $C_{16}$-alkanes of greater than or equal to 95% by mass and where the mixture has a fraction of less than 5% by mass of n-hexadecane.

Such mixtures having $C_{16}$-isoalkanes are obtainable by a method where a) a butene-containing $C_4$-hydrocarbon stream which has less than 5% by mass, based on the total of all butenes, of isobutene, is oligomerized in the presence of a nickel-containing catalyst, b) that a $C_{16}$-olefin fraction is separated off from the reaction mixture and c) that the $C_{16}$ fraction is hydrogenated.

Suitable $C_{16}$-isoalkane mixtures and a method for their preparation are described in DE 10 2004 018 753 A1, to which reference is made here in its entirety. In DE 10 2004 018 753 A1, the hydrocarbon mixtures are referred to as "$C_{16}$-alkane" mixtures although they also have only a very small fraction of n-hexadecane. For the purposes of the present application, the synonymous term "iso" alkane mixture has been used in order to denote alkane mixtures which comprise branched alkanes.

However, particular preference is given to the use of the isoalkane mixtures according to the invention and obtainable according to the inventive method which, as detailed above, have particularly advantageous properties. In particular, they surpass, with regard to the rheological properties and specifically spreading behavior, all oil bodies known from the prior art, including those of DE 10 2004 018 753 A1, which otherwise have good application properties.

The invention therefore further provides a cosmetic or pharmaceutical composition comprising A) at least one isoalkane mixture, as defined above, B) at least one cosmetically or pharmaceutically acceptable active ingredient or effect substance, C) if appropriate at least one further cosmetically or pharmaceutically acceptable auxiliary different from B).

The isoalkane mixtures according to the invention and high $C_{16}$-containing isoalkane mixtures are suitable both for the preparation of homogeneous-phase hydrophobic compositions and also for the formulation of heterogeneous-phase compositions which additionally comprise at least one water-soluble (hydrophilic) liquid or solid compound. Irrespective of the number of their constituents, "homogeneous-phase compositions" have only a single phase. "Heterogeneous-phase compositions" are disperse systems of two or more immiscible components. These include solid/liquid, liquid/liquid and solid/liquid/liquid compositions, such as dispersions and emulsions, e.g. O/W and W/O formulations which have at least one isoalkane mixture according to the invention as oil or fat component and water as immiscible phases.

The isoalkane mixtures according to the invention and high $C_{16}$-containing isoalkane mixtures are also suitable in an advantageous way for producing cosmetic compositions and pharmaceutical compositions in the form of opaque to clear gels.

Active ingredients for cosmetics and drugs are generally understood as meaning substances which develop an effect even in low concentration, e.g. a cosmetic effect on skin and/or hair or a pharmacological effect in an organism. Effect substances are substances which impart a certain property to living things or inanimate substrates, for example colored pigments for make-up.

The cosmetic or pharmaceutical compositions according to the invention comprise component A) preferably in a fraction of from 0.01 to 99.9% by weight, particularly preferably 0.1 to 75% by weight, in particular 1 to 50% by weight, based on the total weight of the composition.

The compositions according to the invention are preferably in the form of an ointment, cream, emulsion, suspension, lotion, milk, paste, gel, foam or spray.

If the isoalkanes A) do not already serve as carriers for the preparation of the compositions, said compositions preferably have a carrier component C) which is chosen from water, hydrophilic components, hydrophobic components and mixtures thereof.

Suitable hydrophilic carriers C) are, for example, mono-, di- or polyhydric alcohols having preferably 1 to 8 carbon atoms, such as ethanol, n-propanol, isopropanol, propylene glycol, glycerol, sorbitol, etc.

Suitable hydrophobic carriers C) are preferably chosen from
i) oils, fats, waxes different from component A),
ii) esters of $C_6$-$C_{30}$-monocarboxylic acids with mono-, di- or trihydric alcohols,
iii) saturated acyclic and cyclic hydrocarbons different from component A),
iv) fatty acids,
v) fatty alcohols,
vi) propellant gases,
and mixtures thereof.

The compositions according to the invention have, for example, an oil or fat component C) which is selected from: hydrocarbons of low polarity, such as mineral oils; linear saturated hydrocarbons, preferably having more than 8 carbon atoms, such as tetradecane, hexadecane, octadecane etc.; cyclic hydrocarbons, such as decahydronaphthalene; branched hydrocarbons different from A); animal and vegetable oils; waxes; wax esters; vaseline; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils C) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example, under the name cyclomethicone.

Preferred oil and fat components C) are chosen from paraffin and paraffin oils; vaseline; natural fats and oils, such as castor oil, soya oil, peanut oil, olive oil, sunflower oil, sesame oil, avocado oil, cocoa butter, almond oil, peach kernel oil, ricinus oil, cod-liver oil, pig fat, spermaceti, spermaceti oil, sperm oil, wheatgerm oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candililla wax, spermaceti, and mixtures of the abovementioned oil and fat components.

Suitable cosmetically and pharmaceutically compatible oil and fat components C) are described in Karl-Heinz Schrader, Grundlagen und Rezepturen der Kosmetika [Fundamentals and formulations of cosmetics], 2nd edition, Verlag Huthig, Heidelberg, pp. 319-355, to which reference is hereby made.

Components B) and C) are selected according to the desired field of use of the composition. Besides components typical of the field of use (e.g. certain pharmaceutical active ingredients), they are selected from carriers, excipients, emulsifiers, surfactants, preservatives, fragrances, perfume oils, thickeners, polymers, gel formers, dyes, pigments, photoprotective agents, consistency regulators, antioxidants, antifoams, antistats, resins, solvents, solubility promoters, neutralizing agents, stabilizers, sterilizing agents, propellants, drying agents, opacifiers, cosmetically active ingredients, hair polymers, hair and skin conditioners, graft polymers, water-soluble or dispersible silicone-containing polymers, bleaches, care agents, colorants, tinting agents, tanning agents, humectants, refatting agents, collagen, protein hydrolyzates, lipids, emollients and softeners.

The cosmetic or pharmaceutical compositions according to the invention can comprise, as cosmetic and/or pharmaceutical active ingredient B) (and also if appropriate as auxiliary C)), at least one cosmetically or pharmaceutically acceptable polymer. These include, very generally, anionic, cationic, amphoteric and neutral polymers.

Examples of anionic polymers are homopolymers and copolymers of acrylic acid and methacrylic acid or salts thereof, copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luviumer® MAE), copolymers of N-tert-butylacrylamide, ethyl acrylate, acrylic acid (Ultrahold® 8, strong), copolymers of vinyl acetate, crotonic acid and if appropriate further vinyl esters (e.g. Luviset® grades), maleic anhydride copolymers, if appropriate reacted with alcohol, anionic polysiloxanes, e.g. carboxy-functional ones, t-butyl acrylate, methacrylic acid (e.g. Luviskol® VBM), copolymers of acrylic acid and meth acrylic acid with hydrophobic monomers, such as, for example, $C_4$-$C_{30}$-alkyl esters of meth (acrylic acid), $C_4$-$C_{30}$-alkylvinyl esters, $C_4$-$C_{30}$-alkyl vinyl ethers and hyaluronic acid. Examples of anionic polymers are also vinyl acetate/crotonic acid copolymers, as are sold, for example, under the names Resyn® (National Starch) and Gafset® (GAF), and vinylpyrrolidone/vinyl acrylate copolymers obtainable, for example, under the trade name Luviflex® (BASF). Further suitable polymers are the vinylpyrrolidone/acrylate terpolymer obtainable under the name Luviflex® VBM-35 (BASF) and polyamides containing sodium sulfonate or polyesters containing sodium sulfonate. Also suitable are vinylpyrrolidone/ethyl methacrylate/methacrylic acid copolymers, as are sold by Stepan under the names Stepanhold-Extra and —R1, and the Carboset® grades from BF Goodrich.

Suitable cationic polymers are, for example, cationic polymers with the INCI name Polyquaternium, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamido copolymers (Polyquaternium-7) and chitosan. Suitable cationic (quaternized) polymers are also Merquat® (polymer based on dimethyldiallylammonium chloride), Gafquat® (quaternary polymers which are formed by reacting polyvinylpyrrolidone with quaternary ammonium compounds), Polymer JR (hydroxyethylcellulose with cationic groups) and cationic polymers based on plants, e.g. guar polymers, such as the Jaguar® grades from Rhodia.

Further suitable polymers are also neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include, for example, Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF); polyamides, e.g. based on itaconic acid and aliphatic diamines, as are described, for example, in DE-A-43 33 238.

Suitable polymers are also amphoteric or zwitterionic polymers, such as the octylacrylamide/methyl methacrylate/tert-butylaminoethyl methacrylate/2-hydroxypropyl methacrylate copolymers obtainable under the names Amphomer® (National Starch), and zwitterionic polymers, as are disclosed, for example, in the German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacroylethylbetaine/methacrylate copolymers, which are commercially available under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or water-dispersible polymers, e.g. polyether siloxanes, such as Tegopren® (Goldschmidt) or Belsil® (Wacker).

Suitable thickeners are crosslinked polyacrylic acids and derivatives thereof, polysaccharides and derivatives thereof, such as xanthan gum, agar agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone.

Suitable cosmetically and/or dermatologically active ingredients are, for example, coloring active ingredients, skin and hair pigmentation agents, tinting agents, tanning agents, bleaches, keratin-hardening substances, antimicrobial active ingredients, photofilter active ingredients, repellant active ingredients, hyperemic substances, keratolytic and keratoplastic substances, antidandruff active ingredients, antiphlogistics, keratinizing substances, active ingredients which act as antioxidants and/or as free-radical scavengers, skin moisturizing or humectant substances, refatting active ingredients, deodorizing active ingredients, sebostatic active ingredients, plant extracts, antierythematous or antiallergic active ingredients and mixtures thereof.

Artificially skin-tanning active ingredients which are suitable for tanning the skin without natural or artificial irradiation with UV rays are, for example, dihydroxyacetone, alloxan and walnut shell extract. Suitable keratin-hardening substances are generally active ingredients as are also used in antiperspirants, such as, for example, potassium aluminum sulfate, aluminum hydroxychloride, aluminum lactate, etc. Antimicrobial active ingredients are used in order to destroy microorganisms and/or to inhibit their growth and thus serve both as preservatives and also as deodorizing substance which reduces the formation or the intensity of body odor. These include, for example, customary preservatives known to the person skilled in the art, such as p-hydroxybenzoates, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc. Suitable repellent active ingredients are compounds which are able to keep or drive certain animals, in particular insects, away from people. These include, for example, 2-ethyl-1,3-hexanediol, N,N-diethyl-m-toluamide etc. Suitable hyperemic substances, which stimulate blood flow in the skin, are, for example, essential oils, such as dwarf-pine, lavender, rosemary, juniper berry, horse chestnut extract, birch leaf extract, hayflower extract, ethyl acetate, camphor, menthol, peppermint oil, rosemary extract, eucalyptus oil, etc. Suitable keratolytic and keratoplastic substances are, for example, salicylic acid, calcium thioglycolate, thioglycolic acid and its salts, sulfur, etc. Suitable antidandruff active ingredients are, for example, sulfur, sulfur polyethylene glycol sorbitan monooleate, sulfur ricinol polyethoxylate, zinc pyrithione, aluminum pyrithione, etc. Suitable antiphlogistics, which counteract skin irritations, are, for example, allantoin, bisabolol, dragosantol, camomile extract, panthenol, etc.

Suitable photofilter active ingredients are substances which absorb UV rays in a UV-B and/or UV/A region. These include photoprotective pigments, e.g. finely disperse metal oxides and salts. These include, for example, titanium dioxide, talc, zinc oxide, barium sulfate, zinc stearate, etc.

Advantageous broadband filters, UV-A filter substances or UV-B filter substances are, for example, representatives of the following classes of compounds:

Bisresorcinyltriazine derivatives with the following structure:

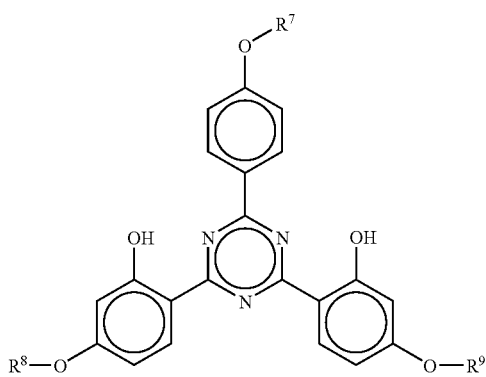

in which $R^7$, $R^8$ and $R^9$ are chosen, independently of one another, from the group of branched and unbranched alkyl groups having 1 to 10 carbon atoms or are a single hydrogen atom. Particular preference is given to 2,4-bis{[4-(2-ethylhexyloxy)-2-hydroxy]phenyl}-6-(4-methoxyphenyl)-1,3,5-triazine (INCI: Aniso Triazine), which can be obtained from CIBA Chemikalien GmbH under the trade name Tinosorb® S.

In addition, other UV filter substances exhibiting the structural unit

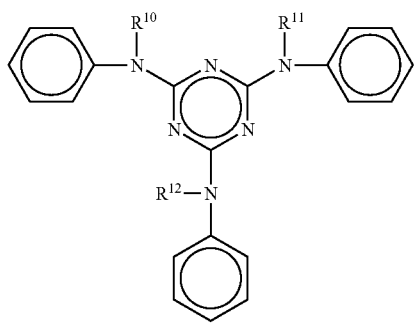

are advantageous UV filter substances for the purposes of the present invention, for example the s-triazine derivatives disclosed in the European Laid-Open Application EP 570 838 A1, the chemical structure of which is represented by the generic formula

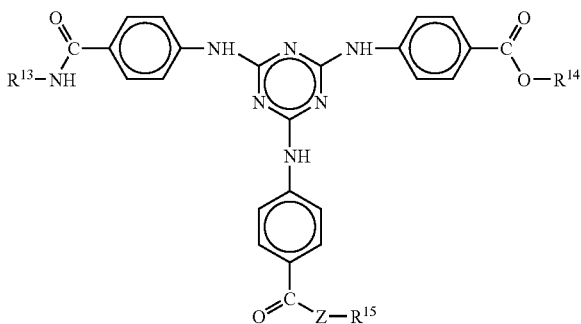

in which $R^{13}$ is a branched or unbranched $C_1$-$C_{18}$-alkyl radical or a $C_5$-$C_{12}$-cycloalkyl radical, optionally substituted by one or more $C_1$-$C_4$-alkyl groups, Z is an oxygen atom or an NH group, $R^{14}$ is a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

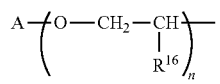

in which

A is a branched or unbranched $C_1$-$C_{18}$-alkyl radical, a $C_5$-$C_{12}$-cycloalkyl radical or an aryl radical, optionally substituted by one or more $C_1$-$C_4$-alkyl groups, $R^{16}$ is a hydrogen atom or a methyl group, n is a number from 1 to 10, $R^{15}$ is a branched or unbranched $C_1$-$C_{18}$-alkyl radical or a $C_5$-$C_{12}$-cycloalkyl radical, optionally substituted by one or more $C_1$-$C_4$-alkyl groups, if X is the NH group, and is a branched or unbranched $C_1$-$C_{18}$-alkyl radical or a $C_5$-$C_{12}$-cycloalkyl radical, optionally substituted by one or more $C_1$-$C_4$-alkyl groups, or a hydrogen atom, an alkali metal atom, an ammonium group or a group of the formula

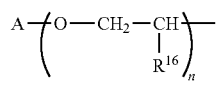

in which

A is a branched or unbranched $C_1$-$C_{18}$-alkyl radical, a $C_5$-$C_{12}$-cycloalkyl radical or an aryl radical, optionally substituted by one or more $C_1$-$C_4$-alkyl groups, $R^{16}$ is a hydrogen atom or a methyl group, n is a number from 1 to 10, if X is an oxygen atom.

Furthermore, a particularly preferred UV filter substance for the purposes of the present invention is an asymmetrically substituted s-triazine, the chemical structure of which is represented by the formula

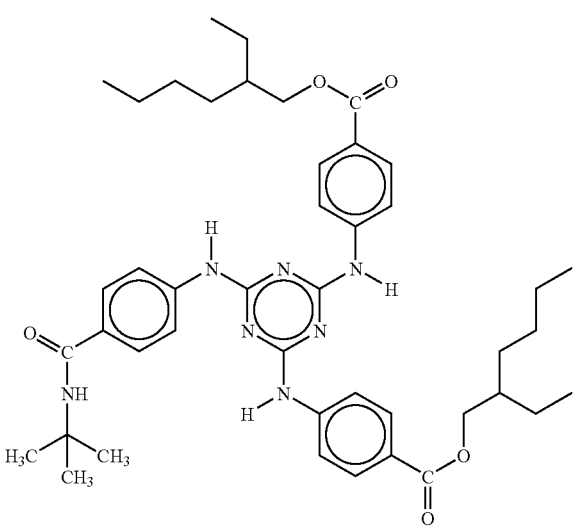

which is also described below as dioctyl butylamido triazone (INCI: Diethylhexylbutamidotriazone) and is available from Sigma 3V under the trade name UVASORB® HEB.

Also advantageous for the purposes of the present invention is a symmetrically substituted s-triazine, tris(2-ethylhexyl) 4,4',4''-(1,3,5-triazine-2,4,6-triyltriimino)trisbenzoate, synonym: 2,4,6-tris[anilino(p-carbo-2'-ethyl-1'-hexyloxy)]-1,3,5-triazine (INCI: Ethylhexyl Triazone), which is sold by BASF Aktiengesellschaft under the trade name UVINUL® T 150.

In addition, European Laid-Open Application 775 698 discloses bisresorcinyltriazine derivatives which are preferably to be used, the chemical structure of which is represented by the generic formula

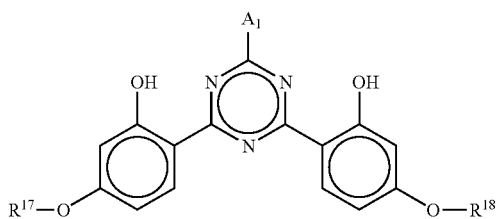

in which $R^{17}$ and $R^{18}$ are, inter alia, $C_3$-$C_{18}$-alkyl or $C_2$-$C_{18}$-alkenyl and $A_1$ is an aromatic radical.

The following compounds are also advantageous for the purposes of the present invention: 2,4-bis{[4-(3-sulfonato)-2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethylcarboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenylamino]-1,3,5-triazine, 2,4-bis{[4-(2-ethylhexyloxy)-2-hydroxy]phenyl}-6-(1-methylpyrrol-2-yl)-1,3,5-triazine, 2,4-bis{[4-tris(trimethylsiloxysilylpropyloxy)-2-hydroxy]phenyl}-6-(4-methoxyphenyl)-1,3,5-triazine, 2,4-bis{[4-(2''-methylpropenyloxy)-2-hydroxy]phenyl}-6-(4-methoxyphenyl)-1,3,5-triazine and 2,4-bis{[4-(1',1',1',3',5',5',5'-heptamethylsiloxy-2''-methylpropyloxy)-2-hydroxy]phenyl}-6-(4-methoxyphenyl)-1,3,5-triazine.

Advantageous oil-soluble UV-B and/or broadband filter substances are, e.g.:
3-benzylidenecamphor derivatives, preferably 3-(4-methylbenzylidene)camphor or 3-benzylidenecamphor;
4-aminobenzoic acid derivatives, preferably 4-(dimethylamino)benzoic acid (2-ethylhexyl) ester or 4-(dimethylamino)benzoic acid amyl ester;
benzophenone derivatives, preferably 2-hydroxy-4-methoxybenzophenone (available from BASF under the trade name Uvinul® M40), 2-hydroxy-4-methoxy-4'-methylbenzophenone, 2,2'-dihydroxy-4-methoxybenzophenone or 2,2',4,4'-tetrahydroxybenzophenone (available from BASF under the trade name Uvinul® D 50).

Particularly advantageous UV filter substances for the purposes of the present invention which are liquid at ambient temperature are homomethyl salicylate, 2-ethylhexyl 2-cyano-3,3-diphenylacrylate, 2-ethylhexyl 2-hydroxybenzoate and esters of cinnamic acid, preferably 4-methoxycinnamic acid (2-ethylhexyl) ester and 4-methoxycinnamic acid isopentyl ester.

Homomethyl salicylate (INCI: Homosalate) is characterized by the following structure:

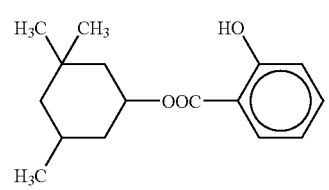

2-Ethylhexyl 2-cyano-3,3-diphenylacrylate (INCI: Octocrylene) is available from BASF under the name Uvinul® N 539T and is characterized by the following structure:

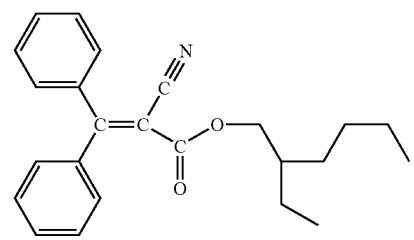 [SMILES: CCCCC(CC)COC(=O)C(C#N)=C(c1ccccc1)c1ccccc1]

2-Ethylhexyl 2-hydroxybenzoate (2-ethylhexyl salicylate, octyl salicylate, INCI: Ethylhexyl Salicylate) is available, for example, from Haarmann & Reimer under the trade name Neo Heliopan® OS and is characterized by the following structure:

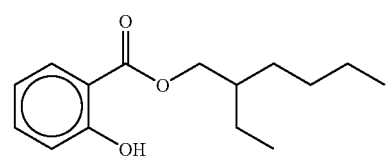

4-Methoxycinnamic acid (2-ethylhexyl) ester (2-ethylhexyl 4-methoxycinnamate, INCI: Ethylhexyl Methoxycinnamate) is, for example, available from BASF under the trade name Uvinul® MC 80 and is characterized by the following structure:

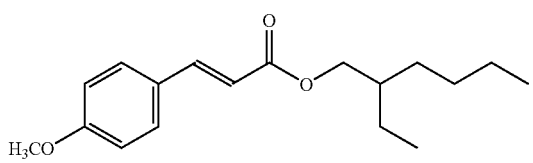 [SMILES: CCCCC(CC)COC(=O)/C=C/c1ccc(OC)cc1]

4-Methoxycinnamic acid isopentyl ester (isopentyl 4-methoxycinnamate, INCI: Isoamyl p-methoxycinnamate) is, for example, available from Haarmann & Reimer under the trade name Neo Heliopan® E 1000 and is characterized by the following structure:

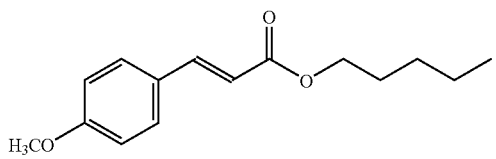 [SMILES: CCCCCOC(=O)/C=C/c1ccc(OC)cc1]

Advantageous dibenzoylmethane derivatives for the purposes of the present invention are, in particular, 4-(tert-butyl)-4'-methoxydibenzoylmethane (CAS No. 70356-09-1), which is sold by BASF under the trade name Uvinul® BMBM and by Merck under the trade name Eusolex® 9020 and which is characterized by the following structure:

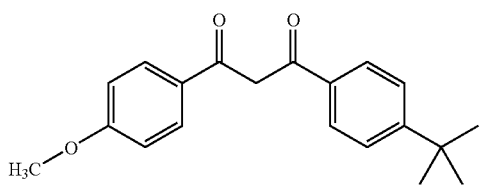 [SMILES: COc1ccc(C(=O)CC(=O)c2ccc(C(C)(C)C)cc2)cc1]

A further advantageous dibenzoylmethane derivative is 4-isopropyldibenzoylmethane (CAS No. 63250-25-9), which is sold by Merck under the name Eusolex® 8020. Eusolex 8020 is characterized by the following structure:

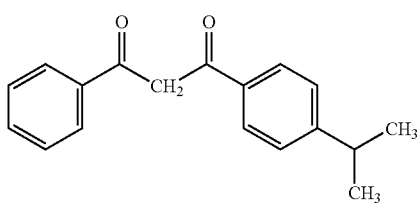 [SMILES: CC(C)c1ccc(C(=O)CC(=O)c2ccccc2)cc1]

Benzotriazoles are characterized by the following structural formula:

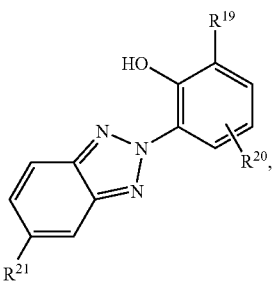

in which
$R^{19}$ and $R^{20}$ are, independently of one another, linear or branched, saturated or unsaturated, substituted (e.g., substituted by a phenyl radical) or unsubstituted alkyl radicals having 1 to 18 carbon atoms.

An advantageous benzotriazole for the purposes of the present invention is furthermore 2-(2H-benzotriazol-2-yl)-4-methyl-6-[2-methyl-3-[1,3,3,3-tetramethyl-1-[(trimethyl-silyl)oxy]disiloxanyl]propyl]phenol (CAS No.: 155633-54-8) with the INCI name Drometrizole Trisiloxane, which is sold by Chimex under the trade name Mexoryl® XL and is characterized by the following structural chemical formula

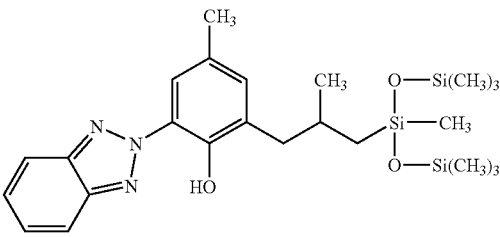

Further advantageous benzotriazoles for the purposes of the present invention are [2,4'-dihydroxy-3-(2H-benzotriazol-2-yl)-5-(1,1,3,3-tetramethylbutyl)-2'-n-octoxy-5'-benzoyl]diphenylmethane, 2,2'-methylenebis[6-(2H-benzotriazol-2-yl)-4-(methyl)phenol], 2,2'-methylenebis[6-(2H-benzotriazol-2-yl)-4-(1,1,3,3-tetramethylbutyl)phenol], 2-(2'-hydroxy-5'-octylphenyl)benzotriazole, 2-(2'-hydroxy-3',5'-di-t-amylphenyl)benzotriazole and 2-(2'-hydroxy-5'-methylphenyl)benzotriazole.

A further UV filter advantageous for the purposes of the present invention is the diphenylbutadiene compound disclosed in EP-A-0 916 335 of the following formula.

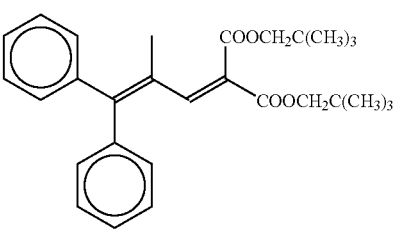

A further UV-A filter advantageous for the purposes of the present invention is the 2-(4-ethoxyanilinomethylene)propanedicarboxylic acid diethyl ester disclosed in EP-A-0 895 776 of the following formula.

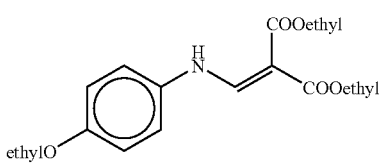

Likewise advantageous for the purposes of the present invention is an amino-substituted hydroxybenzophenone of the following formula:

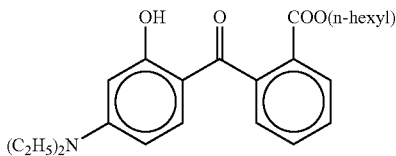

which is sold by BASF Aktiengesellschaft as UV-A filter under the trade name UVINUL® A Plus.

According to a preferred embodiment, the compositions according to the invention are a skin-cleansing composition.

Preferred skin-cleansing compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, shower and bath preparations, such as washing lotions, shower baths and shower gels, foam baths, oil baths and scrub preparations, shaving foams, shaving lotions and shaving creams.

According to a further preferred embodiment, the compositions according to the invention are cosmetic compositions for the care and protection of the skin, nail care compositions or preparations for decorative cosmetics.

Suitable skin cosmetic compositions are, for example, face tonics, face masks, deodorants and other cosmetic lotions. Compositions for use in decorative cosmetics comprise, for example, concealing sticks, stage make-up, mascara and eye shadows, lipsticks, lip gloss, kohl pencils, eye liners, blushers, powder and eyebrow pencils.

Furthermore, the isoalkane mixtures A) can be used in nose strips for pore cleansing, in antiacne compositions, repellents, shaving compositions, hair-removal compositions, intimate care compositions, foot care compositions, and in baby care.

The skin care compositions according to the invention are, in particular, W/O or O/W skin creams, day and night creams, eye creams, face creams, antiwrinkle creams, moisturizing creams, bleach creams, vitamin creams, skin lotions, care lotions and moisturizing lotions.

Skin cosmetic and dermatological compositions based on the above-described isoalkane mixtures A) exhibit advantageous effects. The polymers can, inter alia, contribute to the moisturization and conditioning of the skin and to the improvement in the feel of the skin. By adding the polymers according to the invention, a considerable improvement in the skin compatibility can be achieved in certain formulations.

Skin cosmetic and dermatological compositions comprise preferably at least one isoalkane mixture A) in a fraction of from about 0.001 to 30% by weight, preferably 0.01 to 20% by weight, very particularly preferably 0.1 to 12% by weight, based on the total weight of the composition.

Particularly photoprotective compositions based on the isoalkane mixtures A) have the property of increasing the residence time of the UV-absorbing ingredients compared to customary auxiliaries such as polyvinylpyrrolidone.

Depending on the field of use, the compositions according to the invention can be applied in a form suitable for skin care, such as, for example, in the form of a cream, foam, gel, stick, mousse, milk, spray (pump spray or propellant-containing spray) or lotion.

Besides the isoalkane mixtures A) and suitable carriers, the skin cosmetic preparations can also comprise further active ingredients and auxiliaries customary in skin cosmetics, as described above. These include preferably emulsifiers, preservatives, perfume oils, cosmetic active ingredients, such as phytantriol, vitamin A, E and C, retinol, bisabolol, panthenol, photoprotective agents, bleaches, colorants, tinting agents, tanning agents, collagen, protein hydrolyzates, stabilizers, pH regulators, dyes, salts, thickeners, gel formers, consistency regulators, silicones, humectants, refatting agents and further customary additives.

Preferred additional oil and fat components of the skin cosmetic and dermatological compositions are the above-mentioned mineral and synthetic oils, such as, for example, paraffins, silicone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof.

The isoalkane mixtures according to the invention and high $C_{16}$-containing isoalkane mixtures can also be mixed with conventional oil bodies, as described above, if specific properties are to be set.

The isoalkane mixtures used according to the invention and high $C_{16}$-containing isoalkane mixtures are advantageously suitable for improving the feel to the touch, the spreading behavior, the water resistance and/or the binding of active ingredients and auxiliaries, such as pigments. In addition, the cosmetic preparations can comprise conditioning substances based on silicone compounds. Suitable silicone compounds are, for example, polyalkylsiloxanes, polyarylsiloxanes, polyarylalkylsiloxanes, polyethersiloxanes or silicone resins.

The cosmetic or dermatological preparations are prepared in accordance with customary processes known to the person skilled in the art.

Preferably, the cosmetic and dermatological compositions are in the form of emulsions, in particular in the form of water-in-oil (W/O) emulsions or oil-in-water (O/W) emulsions. It is, however, also possible to choose other types of formulation, for example hydrodispersions, gels, oils, oleogels, multiple emulsions, for example in the form of W/O/W or O/w/O emulsions, anhydrous ointments and ointment bases, etc.

Emulsions are prepared by known methods. Besides at least one isoalkane mixture A) and water, the emulsions comprise, if appropriate, further customary constituents, such as fatty alcohols, fatty acid esters and, in particular, fatty acid triglycerides, fatty acids, lanolin and derivatives thereof, natural or synthetic oils or waxes and emulsifiers in the presence of water. The selection of additives specific to the type of emulsion and the preparation of suitable emulsions is described, for example, in Schrader, Grundlagen und Rezepturen der Kosmetika [Fundamentals and formulations of cosmetics], Hüthig Buch Verlag, Heidelberg, 2nd edition, 1989, third part, which is hereby expressly incorporated by reference.

A suitable emulsion, e.g. for a skin cream etc., generally comprises an aqueous phase which is emulsified by means of a suitable emulsifier system in an oil phase or fat phase. To prepare the hydrophobic phase, an isoalkane mixture A) and if appropriate further oil bodies are used.

Preferred fat components which may additionally be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils whose distillation start point under atmospheric pressure is at about 250° C. and whose distillation end point is at 410° C., such as, for example, vaseline oil; esters of saturated or unsaturated fatty acids, such as alkyl myristates, e.g. isopropyl myristate, butyl myristate or cetyl myristate, hexadecyl stearate, ethyl or isopropyl palmitate, octanoic acid or decanoic acid triglycerides and cetyl ricinoleate.

The fat phase can also comprise silicone oils which are soluble in other oils, such as dimethylpolysiloxane, methylphenylpolysiloxane and the silicone glycol copolymer, fatty acids and fatty alcohols.

Besides the isoalkane mixtures A), waxes can also be used, such as, for example, carnauba wax, candililla wax, beeswax, microcrystalline wax, ozokerite wax and Ca, Mg and Al oleates, myristates, linoleates and stearates.

In addition, an emulsion according to the invention can be in the form of an O/W emulsion. Such an emulsion usually comprises an oil phase, emulsifiers which stabilize the oil phase in the water phase, and an aqueous phase, which is usually in thickened form. Suitable emulsifiers are preferably O/W emulsifiers, such as polyglycerol esters, sorbitan esters or partially esterified glycerides.

According to a further preferred embodiment, the compositions according to the invention are a shower gel, a shampoo formulation or a bath preparation.

Such formulations comprise at least one isoalkane mixture A) and usually anionic surfactants as base surfactants and amphoteric and/or nonionic surfactants as cosurfactants. Further suitable active ingredients and/or auxiliaries are generally chosen from lipids, perfume oils, dyes, organic acids, preservatives and antioxidants, and thickeners/gel formers, skin conditioners and humectants.

These formulations comprise preferably 2 to 50% by weight, preferably 5 to 40% by weight, particularly preferably 8 to 30% by weight of surfactants, based on the total weight of the formulation.

In the washing, shower and bath preparations it is possible to use all of the anionic, neutral, amphoteric or cationic surfactants which are customarily used in body-cleansing compositions.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mols per mole of alcohol. In addition, alkylamine oxides, mono- or dialkylalkanolamides, fatty acid esters of polyethylene glycols, ethoxylated fatty acid amides, alkyl polyglycosides or sorbitan ether esters are suitable.

Furthermore, the washing, shower and bath preparations can comprise customary cationic surfactants, such as, for example, quaternary ammonium compounds, for example cetyltrimethylammonium chloride.

In addition, the shower gel/shampoo formulations can comprise thickeners, such as, for example, sodium chloride, PEG-55, propylene glycol oleate, PEG-120 methylglucose dioleate and others, and also preservatives, further active ingredients and auxiliaries and water.

According to a further preferred embodiment, the compositions according to the invention are a hair-treatment composition.

Hair-treatment compositions according to the invention comprise preferably at least one isoalkane mixture A) in an amount in the range from about 0.1 to 30% by weight, preferably 0.5 to 20% by weight, based on the total weight of the composition.

Preferably, the hair-treatment compositions according to the invention are in the form of a setting foam, hair mousse, hair gel, shampoo, hair spray, hair foam, end fluids, neutralizers for permanent waves, hair colorants and bleaches or hot oil treatments. Depending on the field of use, the hair cosmetic preparations can be applied in the form of (aerosol) spray, (aerosol) foam, gel, gel spray, cream, lotion or wax. Hair sprays here comprise both aerosol sprays and also pump sprays without propellant gas. Hair foams comprise both aerosol foams and pump foams without propellant gas. Hair sprays and hair foams comprise preferably predominantly or exclusively water-soluble or water-dispersible components. If the compounds used in the hair sprays and hair foams according to the invention are water-dispersible, they can be used in the form of aqueous microdispersions having particle diameters of usually 1 to 350 nm, preferably 1 to 250 nm. The solids contents of these preparations are usually in a range from about 0.5 to 20% by weight. These microdispersions generally require no emulsifiers or surfactants for their stabilization.

The hair cosmetic formulations according to the invention comprise, in a preferred embodiment, a) 0.05 to 20% by weight of at least one hair polymer,
b) 20 to 99.95% by weight of carrier material based on an isoalkane mixture according to the invention or a high $C_{16}$-containing isoalkane mixture, and water and/or alcohol,
c) 0 to 50% by weight of at least one propellant gas,
d) 0 to 5% by weight of at least one emulsifier,
e) 0 to 3% by weight of at least one thickener, and
f) up to 25% by weight of further constituents.

Alcohol is understood as meaning all alcohols customary in cosmetics, e.g. ethanol, isopropanol, n-propanol.

Further constituents are understood as meaning the additives customary in cosmetics, for example propellants, antifoams, interface-active compounds, i.e. surfactants, emulsifiers, foam formers and solubilizers. The interface-active compounds used may be anionic, cationic, amphoteric or neutral. Further customary constituents may also be, for example, preservatives, perfume oils, opacifiers, active ingredients, UV filters, care substances, such as panthenol, collagen, vitamins, protein hydrolyzates, alpha- and beta-hydroxycarboxylic acids, stabilizers, pH regulators, dyes, viscosity regulators, gel formers, salts, humectants, refatting agents, complex formers and further customary additives.

Suitable hair polymers are all styling and conditioner polymers known in cosmetics. Suitable conventional hair cosmetic polymers are, for example, the abovementioned cationic, anionic, neutral, nonionic and amphoteric polymers, to which reference is made here.

To set certain properties, the preparations can additionally also comprise conditioning substances based on silicone compounds. Suitable silicone compounds are, for example, polyalkylsiloxanes, polyarylsiloxanes, polyarylalkylsiloxanes, polyethersiloxanes, silicone resins or dimethicone copolyols (CTFA) and amino-functional silicone compounds such as amodimethicone (CTFA).

The polymers according to the invention are particularly suitable as setting agents in hairstyling preparations, in particular hair sprays (aerosol sprays and pump sprays without propellant gas) and hair foams (aerosol foams and pump foams without propellant gas).

In a preferred embodiment, spray preparations comprise
a) 0.1 to 10% by weight of at least one hair polymer,
b) 20 to 99.9% by weight of water and/or alcohol,
c) 0 to 70% by weight of at least one propellant,
d) 0 to 20% by weight of further constituents,
e) 0.01 to 10% by weight of isoalkane mixture according to the invention or high $C_{16}$-containing isoalkane mixture.

Propellants are the propellants used customarily for hair sprays or aerosol foams. Preference is given to mixtures of propane/butane, pentane, dimethyl ether, 1,1-difluoroethane (HFC-152 a), carbon dioxide, nitrogen or compressed air.

A formulation for aerosol hair foams preferred according to the invention comprises
a) 0.1 to 10% by weight of at least one hair polymer,
b) 55 to 99.8% by weight of water und/or alcohol,
c) 5 to 20% by weight of a propellant,
d) 0.1 to 5% by weight of an emulsifier,
e) 0 to 10% by weight of further constituents,
f) 0.01 to 10% by weight of isoalkane mixture according to the invention or high $C_{16}$-containing isoalkane mixture.

Emulsifiers which may be used are all of the emulsifiers customarily used in hair foams. Suitable emulsifiers may be nonionic, cationic or anionic or amphoteric.

Examples of nonionic emulsifiers (INCI nomenclature) are laureths, e.g. laureth-4; ceteths, e.g. ceteth-1, polyethylene glycol cetyl ether; cetheareths, e.g. ceteareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimonium bromide, cocotrimonium methylsulfate, quaternium-1 to x (INCI).

Anionic emulsifiers may be chosen, for example, from the group of alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

A preparation suitable according to the invention for styling gels can, for example, have the following composition:
a) 0.1 to 10% by weight of at least one hair polymer,
b) 80 to 99.85% by weight of water and/or alcohol,
c) 0 to 3% by weight, preferably 0.05 to 2% by weight, of an isoalkane mixture according to the invention or high $C_{16}$-containing isoalkane mixture,
d) 0 to 20% by weight of further constituents.

In the preparation of gels based on the isoalkane mixtures A) according to the invention or based on high $C_{16}$-containing isoalkane mixtures, customary gel formers can, if required, additionally be used, for example in order to set specific rheological or other application properties of the gels. Gel formers which can be used are all gel formers customary in cosmetics. These include lightly crosslinked polyacrylic acid, for example Carbomer (INCI), cellulose derivatives, e.g. hydroxypropylcellulose, hydroxyethylcellulose, cationically modified celluloses, polysaccharides, e.g. xanthan gum, caprylic/capric triglyceride, sodium acrylate copolymers, polyquaternium-32 (and) Paraffinum Liquidum (INCI), sodium acrylate copolymers (and) Paraffinum Liquidum (and) PPG-1 Trideceth-6, acrylamidopropyltrimonium chloride/acrylamide copolymers, Steareth-10 allyl ether acrylate copolymers, Polyquaternium-37 (and) Paraffinum Liquidum (and) PPG-1 Trideceth-6, Polyquaternium 37 (and) propylene glycol dicaprate dicaprylate (and) PPG-1 Trideceth-6, Polyquaternium-7, Polyquaternium-44. Crosslinked homopolymers of acrylic acid which are suitable as gel formers are, for example, commercially available under the name Carbopol® from BF GOODRICH. Preference is also given to hydrophobically modified crosslinked polyacrylate polymers, such as Carbopol® Ultrez 21 from Noveon. Further examples of anionic polymers suitable as gel formers are copolymers of acrylic acid and acrylamide and salts thereof; acrylate copolymers, such as Luvigel® EM; sodium salts of polyhydroxycarboxylic acids, water-soluble or water-dispersible polyesters, polyurethanes and polyureas. Particularly suitable polymers are copolymers of (meth)acrylic acid and polyether acrylates, where the polyether chain is terminated with a $C_8$-$C_{30}$-alkyl radical. These include, for example, acrylate/Beheneth-25 methacrylate copolymers, which are available under the name Aculyn® from Rohm and Haas.

The isoalkane mixtures A) according to the invention can be used in cosmetic preparations as conditioners.

The isoalkane mixtures A) according to the invention can preferably be used in shampoo formulations as setting agents and/or conditioners. Preferred shampoo formulations comprise
a) 0.05 to 10% by weight of at least one isoalkane mixture according to the invention or high $C_{16}$-containing isoalkane mixture,
b) 25 to 94.95% by weight of water,
c) 5 to 50% by weight of surfactants,
c) 0 to 5% by weight of a further conditioner,
d) 0 to 10% by weight of further cosmetic constituents.

In the shampoo formulations, all of the anionic, neutral, amphoteric or cationic surfactants used customarily in shampoos can be used.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

For example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate are suitable.

Suitable amphoteric surfactants are, for example, alkylbetaines, alkylamidopropylbetaines, alkylsulfobetaines, alkyl glycinates, alkyl carboxyglycinates, alkyl amphoacetates or -propionates, alkyl amphodiacetates or -dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mols per mole of alcohol. In addition, alkylamine oxides, mono- or dialkylalkanolamides, fatty acid esters of polyethylene glycols, alkyl polyglycosides or sorbitan ether esters are suitable.

Furthermore, the shampoo formulations can comprise customary cationic surfactants, such as, for example, quaternary ammonium compounds, for example cetyltrimethylammonium chloride.

In the shampoo formulations, in order to achieve certain effects, customary conditioners can be used in combination with the isoalkane mixtures A). These include, for example, the abovementioned cationic polymers with the INCI name Polyquaternium, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinyl-imidazolium salts (Luviquat® Hold); cationic cellulose derivatives (Polyquaternium-4 and -10), acrylamide copolymers (Polyquaternium-7). It is also possible to use protein hydrolyzates, and conditioning substances based on silicone compounds, for example polyalkylsiloxanes, polyarylsiloxanes, polyarylalkylsiloxanes, polyethersiloxanes or silicone resins. Further suitable silicone compounds are dimethicone copolyols (CTFA) and amino-functional silicone compounds, such as amodimethicone (CTFA). In addition, cationic guar derivatives such as guar hydroxypropyltrimonium chloride (INCI) can be used.

The isoalkane mixtures according to the invention and the high $C_{16}$-containing isoalkane mixtures are particularly advantageously suitable for the preparation of and/or joint use with copolymers Ca), which are obtainable by copolymerization of (A) at least one ethylenically unsaturated dicarboxylic acid anhydride derived from at least one dicarboxylic acid having 4 to 8 carbon atoms, (B) at least one oligomer derived from at least one branched or unbranched $C_3$-$C_{10}$-alkene, where the oligomer has an average molecular weight $M_n$ in the range from 300 to 5000 g/mol, preferably up to 1200 g/mol, or is obtainable by oligomerization of at least 3 equivalents of $C_3$-$C_{10}$-alkene, (C) optionally at least one α-olefin having up to 24, preferably having up to 16, carbon atoms, (D) optionally at least one further ethylenically unsaturated comonomer different from (A), (B) and (C), if appropriate reaction with (E) at least one compound of the general formula Ia, Ib, Ic or Id

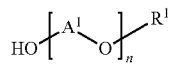

Ia

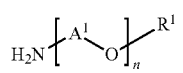

Ib

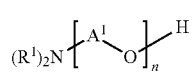

Ic

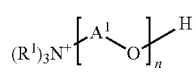

Id where
$A^1$ $C_2$-$C_{20}$-alkylene, identical or different,
$R^1$ $C_1$-$C_{30}$-alkyl, linear or branched, phenyl or hydrogen,
n an integer from 1 to 200 and
if appropriate subsequent contacting with water.

If appropriate, the copolymers Ca) can be in a mixture with at least one additional oligomer Z), as defined previously as component B).

Suitable oligomers B) are the isoalkane mixtures according to the invention. Suitable oligomers B) are also oligomers different therefrom, in particular oligomers of propylene or unbranched or preferably branched $C_4$-$C_{10}$-olefins, where at least one oligomer has an average molecular weight $M_n$ in the range from 300 to 5000 g/mol, preferably up to 1200 g/mol, or is obtainable by oligomerization of at least 3 equivalents of $C_3$-$C_{10}$-alkene. Also suitable as component B) are mixtures of the isoalkane mixtures according to the invention with oligomers different therefrom. Also suitable as additional oligomer component Z) are the isoalkane mixtures according to the invention. Furthermore, suitable oligomers Z) are also oligomers different therefrom, in particular oligomers of propylene or unbranched or preferably branched $C_4$-$C_{10}$-olefins, where at least one oligomer has an average molecular weight $M_n$ in the range from 300 to 5000 g/mol, preferably up to 1200 g/mol or is obtainable by oligomerization of at least 3 equivalents of $C_3$-$C_{10}$-alkene. Also suitable as component Z) are mixtures of the isoalkane mixtures according to the invention with oligomers different therefrom.

According to the invention, component B) and/or oligomer Z) comprises at least one isoalkane mixture, as defined above, or consists of such an isoalkane mixture.

Formulations of the copolymers Ca) based on the isoalkane mixtures according to the invention are particularly suitable for cosmetic compositions for the treatment of keratin surfaces.

With regard to suitable formulation components of these cosmetic compositions, reference is made to the previous statements. Suitable copolymers Ca) are described below.

The copolymers Ca) or mixtures thereof with at least one further oligomer Z) are present in the compositions according to the invention in an amount of from 0.1 to 15% by weight, particularly preferably 1 to 10% by weight, in particular 2 to 6% by weight, based on the weight of the composition. If the copolymer Ca) is present in a mixture with an oligomer component Z), then the weight ratio of oligomer component Z) to copolymer Ca) is preferably 1:10 to 3:1, particularly preferably 1:5 to 2:1 and very particularly preferably 1:2 to 1.5:1.

The copolymer Ca) is obtainable by preferably free-radical copolymerization of

A) at least one ethylenically unsaturated dicarboxylic acid anhydride derived from at least one dicarboxylic acid having 4 to 8 carbon atoms, for example maleic anhydride, itaconic anhydride, citraconic anhydride, methylenemalonic anhydride, preferably itaconic anhydride and maleic anhydride and very particularly preferably maleic anhydride;
B) at least one oligomer of branched or unbranched $C_3$-$C_{10}$-alkene, where at least one oligomer has an average molecular weight $M_n$ in the range from 300 to 5000 g/mol, preferably up to 1200 g/mol, or is obtainable by oligomerization of at least 3 equivalents of $C_3$-$C_{10}$-alkene,
C) optionally at least one α-olefin having up to 24, preferably having up to 16, carbon atoms,
D) optionally at least one further ethylenically unsaturated comonomer different from A), B) and C), if appropriate reaction with
E) at least one compound of the general formula Ia, Ib, Ic or Id

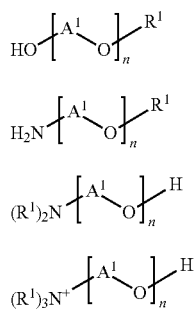

where
$A^1$ $C_2$-$C_{20}$-alkylene, identical or different,
$R^1$ $C_1$-$C_{30}$-alkyl, linear or branched, phenyl or hydrogen,
n an integer from 1 to 200,
where the carboxyl groups of the copolymer a) may be at least partially esterified or amidated, and, if appropriate, subsequent contacting with water.

Suitable oligomers B) and/or Z) are, as detailed above, the isoalkane mixtures according to the invention and the high $C_{16}$-containing isoalkane mixtures, oligomers different therefrom, and mixtures of the isoalkane mixtures according to the invention with oligomers different therefrom.

By way of example of the oligomers different from the isoalkane mixtures according to the invention, mention may be made of oligomers of propylene, isobutene, 1-pentene, 2-methylbutene-1,1-hexene, 2-methylpentene-1,2-methylhexene-1,2,4-dimethyl-1-hexene, diisobutene (mixture of 2,4,4-trimethyl-1-pentene and 2,4,4-trimethyl-2-pentene), 2-ethylpentene-1,2-ethylhexene-1 and 2-propylheptene-1,1-octene, 1-decene and 1-dodecene, very particular preference being given to oligomers of isobutene, diisobutene and 1-dodecene.

These oligomers B) and Z) have an ethylenically unsaturated group which may be in the form of a vinyl, vinylidene or alkylvinylidene group.

Co-oligomers of the abovementioned olefins with one another or with up to 20% by weight, based on B) and Z), of vinylaromatics, such as styrene and α-methylstyrene, $C_1$-$C_4$-alkylstyrene, such as, for example, 2-, 3- and 4-methylstyrene, and 4-tert-butylstyrene, are also suitable.

Particularly preferred oligomers B) and Z) are oligopropylenes and oligoisobutenes with an average molecular weight $M_n$ up to 1200 g/mol, preferably in the range from 300 to 1000 g/mol, particularly preferably of at least 400 g/mol, very particularly preferably of at least 500 g/mol, for example determined by means of gel permeation chromatography (GPC).

In one embodiment of the present invention, oligomers B) and Z) have a polydispersity $M_w/M_n$ in the range from 1.1 to 10, preferably up to 5 and particularly preferably from 1.5 to 1.8.

In one embodiment of the present invention, oligomers B) and Z) have a bimodal molecular weight distribution with a maximum of $M_n$ in the range from 500 to 1200 g/mol and a local maximum of $M_n$ in the range from 2000 to 5000 g/mol.

Oligomer B) may be identical to or different from additionally used oligomers Z), if appropriate. In one embodiment of the present invention, oligomer B) and additional oligomer Z) are identical.

Suitable additional oligomers Z) are preferably oligomers of $C_4$-olefins. In one embodiment of the invention, the oligomers Z) are hydrogenated oligomers of $C_4$-olefins. As oligomers Z), particular preference is also given to, optionally hydrogenated, oligomers of 3, 4, 5, 6, 7 or 8 $C_4$-olefin molecules.

Comonomer C)

α-Olefins having up to 16 carbon atoms used as comonomer C) are selected from propylene, 1-butene, isobutene, 1-pentene, 4-methylbut-1-ene, 1-hexene, diisobutene (mixture of 2,4,4-trimethyl-1-pentene and 2,4,4-trimethyl-2-pentene), 1-heptene, 1-octene, 1-decene, 1-dodecene, 1-tetradecene and 1-hexadecene; particular preference is given to isobutene, diisobutene and 1-dodecene.

To prepare copolymer Ca) used according to the invention, the components A), B) and, if appropriate, C) can be copolymerized with one another. It is also possible, for the preparation of copolymer Ca) according to the invention, to copolymerize the components A), B) and, if appropriate, C) with one another and, if appropriate, to react with E), or to copolymerize A), B) and, if appropriate, C) and, if appropriate, a further comonomer D) with one another, or it is possible to copolymerize A) and B) and, if appropriate, C) and, if appropriate, a further comonomer D) with one another and, if appropriate, to react with E).

If it is desired to use a copolymer Ca) whose carboxyl groups are at least partially esterified or amidated, then the compound E) selected is at least one compound of the general formula Ia to Id, preferably Ia,

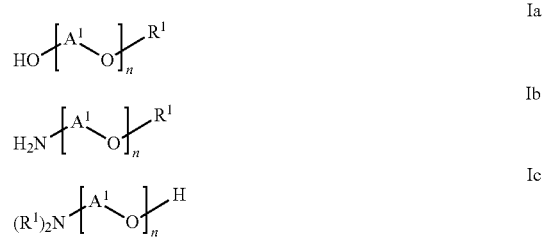

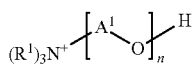

where the variables are defined as follows:

$A^1$ $C_2$-$C_{20}$-alkylene, for example —$(CH_2)_2$—, —$CH_2$—CH($CH_3$)—, —$(CH_2)_3$—, —$CH_2$—CH($C_2H_5$)—, —$(CH_2)_4$—, —$(CH_2)_5$—, —$(CH_2)_6$—, preferably $C_2$-$C_4$-alkylene; in particular —$(CH_2)_2$—, —$CH_2$—CH($CH_3$)— and —$CH_2$—CH($C_2H_5$)—;

$R^1$ phenyl,
hydrogen
or preferably $C_1$-$C_{30}$-alkyl, linear or branched, such as methyl, ethyl, n-propyl, iso-propyl, n-butyl, isobutyl, sec-butyl, tert-butyl, n-pentyl, isopentyl, sec-pentyl, neo-pentyl, 1,2-dimethylpropyl, isoamyl, n-hexyl, isohexyl, sec-hexyl, n-heptyl, n-octyl, n-nonyl, n-decyl, n-dodecyl, n-hexadecyl, n-octadecyl, n-eicosyl; particularly preferably $C_1$-$C_4$-alkyl, such as methyl, ethyl, n-propyl, isopropyl,
n-butyl, isobutyl, sec-butyl and tert-butyl, very particularly preferably methyl.

n an integer in the range from 1 to 200, preferably 4 to 20.

The groups $A^1$ may of course only be different if n is a number greater than 1 or if different compounds of the general formulae I a to I d are used.

Particular examples of compounds of the general formulae Ia are
- methyl terminally-capped polyethylene glycols of the formula HO—$(CH_2CH_2O)_m$—$CH_3$ where m=1 to 200, preferably 4 to 100, particularly preferably 4 to 50;
- methyl terminally-capped block copolymers of ethylene oxide, propylene oxide and/or butylene oxide with a molecular weight $M_n$ of from 300 to 5000 g/mol;
- methyl terminally-capped random copolymers of ethylene oxide, propylene oxide and/or butylene oxide with a molecular weight $M_n$ of from 300 to 5000 g/mol;
- alkoxylated $C_2$-$C_{30}$-alcohols, in particular fatty alcohol alkoxylates, oxo alcohol alkoxylates or Guerbet alcohol alkoxylates, where the alkoxylation can be carried out with ethylene oxide, propylene oxide and/or butylene oxide. Examples are:
- $C_{13}$-$C_{15}$-oxo alcohol ethoxylates with 3 to 30 ethylene oxide units;
- $C_{13}$-oxo alcohol ethoxylates with 3 to 30 ethylene oxide units;
- $C_{12}C_{14}$-fatty alcohol ethoxylates with 3 to 30 ethylene oxide units;
- $C_{10}$-oxo alcohol ethoxylates with 3 to 30 ethylene oxide units;
- $C_{10}$-Guerbet alcohol ethoxylates with 3 to 30 ethylene oxide units;
- $C_9$-$C_{11}$-oxo alcohol alkoxylates with 2 to 20 ethylene oxide units, 2 to 20 propylene oxide units and/or 1 to 5 butylene oxide units;
- $C_{13}$-$C_{15}$-oxo alcohol alkoxylates with 2 to 20 ethylene oxide units, 2 to 20 propylene oxide units and/or 1 to 5 butylene oxide units;
- $C_4$-$C_{20}$-alcohol ethoxylates with 2 to 20 ethylene oxide units.

Preferred examples of compounds of the formula Ib are methyl terminally-capped polyethylene glycolamines of the formula $H_2N$—$(CH_2CH_2O)_m$—$CH_3$ where m=1 to 200, preferably 4 to 100, particularly preferably 4 to 50.

If reaction with compound Id is desired, then compound Ic can be reacted with alkylating agents such as, for example, halides or sulfates of the formula $R^1$—Y where Y is chosen from Cl, Br and I or $(R^1)_2SO_4$. Depending on the alkylating agent or agents used, compound Id with Y, $SO_4^{2-}$ or $R^1$—$SO_4^-$ as counterion is obtained.

In one embodiment of the present invention, mixtures of different components E), for example of the formula Ia, are used. In particular, it is possible to use those mixtures of compounds of the formula Ia in which—based in each case on the mixture—at least 95 mol %, preferably at least 98 mol % to at most 99.8 mol %, of $R^1$ is $C_1$-$C_{30}$-alkyl and at least 0.2 mol % and at most 5 mol %, preferably at most 2 mol %, is hydrogen.

In one embodiment of the present invention, for the preparation of the copolymer Ca) used according to the invention, the reaction mixture is contacted after the preferably free-radical copolymerization and, if appropriate, the reaction with E), with water, where the water can also comprise Brønsted acid or preferably Brønsted base. Examples of Brønsted acids are sulfuric acid, hydrochloric acid, tartaric acid and citric acid. Examples of Brønsted base are alkali metal hydroxide, such as, for example, NaOH and KOH, alkali metal carbonate, such as, for example, $Na_2CO_3$ and $K_2CO_3$, alkali metal hydrogencarbonate, such as, for example, $NaHCO_3$ and $KHCO_3$, ammonia, amines, such as, for example, trimethylamine, triethylamine, diethylamine, ethanolamine, N,N-diethanolamine, N,N,N-triethanolamine, N-methylethanolamine.

In another embodiment of the present invention, it is possible to contact with water during the preferably free-radical copolymerization.

Monomers D)

The monomer or monomers D) which can optionally be used for preparing copolymer Ca) used according to the invention are different from A), B) and C). Preferred monomers D) to be mentioned are:

$C_3$-$C_8$-Carboxylic acids or carboxylic acid derivatives of the general formula II

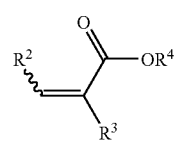

carboxamides of the formula III,

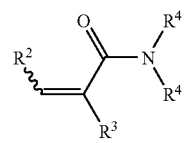

noncyclic amides of the general formula IV a and cyclic amides of the general formula IV b

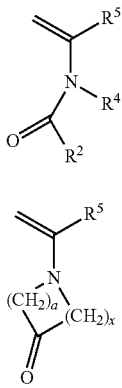

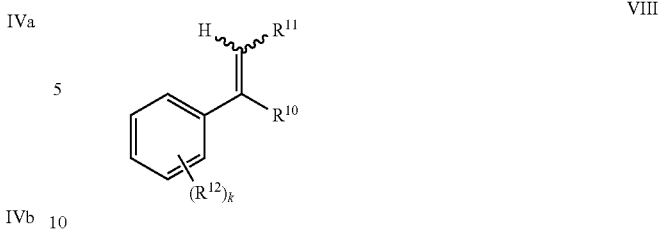

$C_1$-$C_{20}$-alkyl vinyl ethers, such as methyl vinyl ether, ethyl vinyl ether, n-propyl vinyl ether, isopropyl vinyl ether, n-butyl vinyl ether, isobutyl vinyl ether, 2-ethylhexyl vinyl ether or n-octadecyl vinyl ether;

N-vinyl derivatives of nitrogen-containing aromatic compounds, preferably N-vinylimidazole, 2-methyl-1-vinylimidazole, N-vinyloxazolidone, N-vinyltriazole, 2-vinylpyridine, 4-vinylpyridine, 4-vinylpyridine N-oxide, N-vinylimidazoline, N-vinyl-2-methylimidazoline, α,β-unsaturated nitriles, such as, for example, acrylonitrile, methacrylonitrile;

alkoxylated unsaturated ethers of the general formula V,

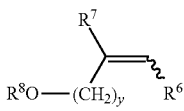

esters and amides of the general formula VI,

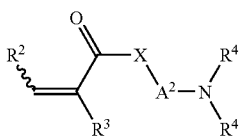

unsaturated esters of the general formula VII

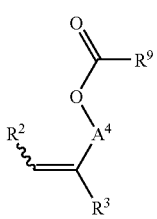

vinylaromatic compounds of the general formula VIII phosphate-, phosphonate-, sulfate-, and sulfonate-containing comonomers, such as, for example, [2-{(meth)acryloyloxy}ethyl]phosphate, 2-(meth)acrylamido-2-methyl-1-propanesulfonic acid;

α-olefins, linear or branched, having 18 to 40 carbon atoms, preferably having up to 24 carbon atoms, for example 1-octadecene, 1-eicosene, α-$C_{22}H_{44}$, α-$C_{24}H_{48}$ and mixtures of the abovementioned α-olefins.

Here, the variables are defined as follows:

$R^2$, $R^3$ identical or different and selected from unbranched or branched $C_1$-$C_5$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, particularly preferably $C_1$-$C_4$-alkyl, such as methyl, ethyl, n-propyl, isopropyl, n-butyl, isobutyl, sec-butyl and tert-butyl;

and in particular hydrogen;

$R^4$ identical or different and $C_1$-$C_{22}$-alkyl, branched or unbranched, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, n-nonyl, n-decyl, n-dodecyl, n-eicosyl; particularly preferably $C_1$-$C_4$-alkyl, such as methyl, ethyl, n-propyl, isopropyl, n-butyl, isobutyl, sec-butyl and tert-butyl;

or particularly preferably hydrogen;

$R^5$ hydrogen or methyl;

x an integer in the range from 2 to 6, preferably 3 to 5;

y an integer selected from 0 or 1, preferably 1;

a an integer in the range from 0 to 6, preferably in the range from 0 to 2;

$R^6$, $R^7$ identical or different and selected from hydrogen, unbranched or branched $C_1$-$C_{10}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, iso-amyl, n-hexyl, isohexyl, sec-hexyl, n-heptyl, n-octyl, n-nonyl, n-decyl, preferably $C_1$-$C_4$-alkyl, such as methyl, ethyl, n-propyl, isopropyl, n-butyl, isobutyl, sec-butyl and tert-butyl, very particularly preferably methyl;

X oxygen or N—$R^4$;

$R^8$ [$A^3$-O]$_n$—$R^4$;

$R^9$ selected from unbranched or branched $C_1$-$C_{20}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, iso-amyl, n-hexyl, isohexyl, sec-hexyl, n-heptyl, n-octyl, n-nonyl, n-decyl, n-dodecyl, n-tetradecyl, n-hexadecyl, n-octadecyl, n-eicosyl; preferably $C_1$-$C_{14}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, n-nonyl, n-decyl, n-dodecyl, n-tetradecyl, and in particular hydrogen or methyl;

$R^{10}$, $R^{11}$ independently of one another, in each case hydrogen, methyl or ethyl, preferably $R^{10}$ and $R^{11}$ are each hydrogen;

$R^{12}$ methyl or ethyl;

k is an integer in the range from 0 to 2, preferably k=0;

$A^2$, $A^3$ identical or different and $C_2$-$C_{20}$-alkylene, for example —(CH$_2$)$_2$—, —CH$_2$—CH(CH$_3$)—, —(CH$_2$)$_3$—, —CH$_2$—CH(C$_2$H$_5$)—, —(CH$_2$)$_4$—, —(CH$_2$)$_5$—, —(CH$_2$)$_6$—, preferably $C_2$-$C_4$-alkylene; in particular —(CH$_2$)$_2$—, —CH$_2$—CH(CH$_3$)— and —(CH$_2$)$_3$—;

$A^4$ $C_1$-$C_{20}$-alkylene, for example —CH$_2$—, —CH(CH$_3$)—, —CH(C$_6$H$_5$)—, —C(CH$_3$)$_2$—, —(CH$_2$)$_2$—, —CH$_2$—CH(CH$_3$)—, —(CH$_2$)$_3$—, —CH$_2$—CH(C$_2$H$_5$)—, —(CH$_2$)$_4$—, —(CH$_2$)$_5$—, —(CH$_2$)$_6$—, preferably $C_2$-$C_4$-alkylene; in particular —(CH$_2$)$_2$—, —CH$_2$—CH(CH$_3$)— and —(CH$_2$)$_3$—, or in particular a single bond.

The other variables are as defined above.

Compounds of the formula III selected by way of example are (meth)acrylamides, such as acrylamide, N-methylacrylamide, N,N-dimethylacrylamide, N-ethylacrylamide, N-propylacrylamide, N-tert-butylacrylamide, N-tert-octylacrylamide, N-undecylacrylamide or the corresponding methacrylamides.

Compounds of the formula IV a selected by way of example are N-vinylcarboxamides, such as N-vinylformamide, N-vinyl-N-methylformamide, N-vinylacetamide or N-vinyl-N-methylacetamide; representatives of compounds of the formula IV b selected by way of example are N-vinylpyrrolidone, N-vinyl-4-piperidone and N-vinyl-ε-caprolactam.

Compounds of the formula VI selected by way of example are (meth)acrylic acid esters and amides, such as N,N-dialkylaminoalkyl(meth)acrylates or N,N-dialkylaminoalkyl(meth)acrylamides; examples are N,N-dimethylaminoethyl acrylate, N,N-dimethylaminoethyl methacrylate, N,N-diethylaminoethyl acrylate, N,N-diethylaminoethyl methacrylate, N,N-dimethylaminopropyl acrylate, N,N-dimethylaminopropyl methacrylate, N,N-diethylaminopropyl acrylate, N,N-diethylaminopropyl methacrylate, 2-(N,N-dimethylamino)ethylacrylamide, 2-(N,N-dimethylamino)ethylmethacrylamide, 2-(N,N-diethylamino)ethylacrylamide, 2-(N,N-diethylamino)ethylmethacrylamide, 3-(N,N-dimethylamino)propylacrylamide and 3-(N,N-dimethylamino)propylmethacrylamide.

Compounds of the formula VII selected by way of example are vinyl acetate, allyl acetate, vinyl propionate, vinyl butyrate, vinyl 2-ethylhexanoate or vinyl laurate.

Vinylaromatic compounds of the general formula VIII selected by way of example are α-methylstyrene, para-methylstyrene and in particular styrene.

As comonomer D), very particular preference is given to using: acrylic acid, 1-octadecene, methacrylic acid, methyl acrylate, methyl methacrylate, acrylamide, vinyl n-butyl ether, vinyl isobutyl ether, styrene, N-vinylformamide, N-vinylpyrrolidone, 1-vinylimidazole and 4-vinylpyridine.

As regards A), B), if appropriate C) and if appropriate D), the copolymers Ca) can be block copolymers, alternating copolymers or random copolymers, preference being given to alternating copolymers.

In one embodiment of the present invention, the anhydride groups of copolymer Ca) are present in completely or partially hydrolyzed and, if appropriate, neutralized form after the polymerization.

In one embodiment of the present invention, the anhydride groups of copolymer Ca) are present as anhydride groups after the copolymerization.

In one embodiment of the present invention, the molar ratios of copolymer Ca) used according to the invention are A) in the range from 5 to 60 mol %, preferably 10 to 55 mol %, B) in the range from 1 to 95 mol %, preferably 5 to 70 mol %, C) in the range from 0 to 60 mol %, preferably 10 to 55 mol %, D) 0 to 70 mol %, preferably 1 to 50 mol %, in each case based on copolymer, where the sum of A), B), C) and D) gives 100 mol %, and E) in the range from 0 to 50 mol %, preferably 1 to 30 mol %, particularly preferably 2 to 20 mol %, based on all carboxyl groups in the copolymer.

In one embodiment, a weight ratio of additional oligomers Z) to copolymer Ca) in the range from 0.1:1 to 100:1, preferably from 0.5:1 to 10:1, is chosen.

In another embodiment, a weight ratio of additional oligomers Z) to copolymer Ca) in the range from 1:1 to 100:1, preferably from 10:1 to 50:1, is chosen.

The copolymers Ca) used according to the invention and their mixtures of oligomers Z) are described in the German patent applications with the application numbers DE 10353557.8, DE 10355402.5 and DE 10345094.7, to which reference is hereby made in their entirety.

In one embodiment of the present invention, the copolymers Ca) of A), B) and if appropriate C) and D) used according to the invention have an average molar mass $M_w$ in the range from 1000 g/mol to 50 000 g/mol, preferably 1500 g/mol to 25 000 g/mol, determined, for example, by gel permeation chromatography with dimethylacetamide as solvent and polymethyl methacrylate as standard.

Copolymers Ca) of A), B) and, if appropriate, C) and D) and E) used according to the invention can be, as regards A), B) and if appropriate C) and D), block copolymers, alternating copolymers or random copolymers, with alternating copolymers being preferred.

The polydispersity $M_w/M_n$ of the copolymers Ca) is generally in the range from 1.1 to 20, preferably from 2 to 10.

Preferably, the copolymers Ca) have K values in accordance with Fikentscher in the range from 5 to 100, preferably 8 to 30 (measured in accordance with H. Fikentscher at 25° C. in cyclohexanone and a polymer concentration of 2% by weight).

To prepare suitable copolymers Ca), the starting materials are A), B) and if appropriate C) and D), which are preferably free-radically copolymerized with one another and if appropriate reacted with E). The reaction with E) can take place before, during and after the copolymerization. During or preferably after the copolymerization, the mixture can be contacted with water. However, to prepare the copolymers Ca), it is also possible to dispense with the contacting with water.

If a reaction of copolymer of A), B) and if appropriate C) and D) with E) or a free-radical copolymerization in the presence of E) is desired, then the total amount of E) is preferably calculated in such a way that a complete conversion of E) is assumed and up to 50 mol %, preferably 1 to 30 mol %, particularly preferably 2 to 20 mol % of E), based on all carboxyl groups of the copolymer, is used. For the purposes of the present invention, the term "all carboxyl groups present in the polymer" is to be understood as meaning those carboxyl groups from copolymerized comonomers A) and if appropriate D) which are present as anhydride, as $C_1$-$C_4$-alkyl ester and as carboxylic acid.

The free-radical copolymerization is advantageously started by the customary initiators known for this purpose, for example peroxides or hydroperoxides.

The copolymerization can be carried out in the presence or the absence of solvents and precipitants. Suitable solvents for the free-radical copolymerization are polar solvents inert toward acid anhydride, such as, for example, acetone, tetrahydrofuran and dioxane. Suitable precipitants are, for example, toluene, ortho-xylene, meta-xylene and aliphatic hydrocarbons.

In a preferred embodiment, the method is carried out without solvents or in the presence of only small amounts of solvent, i.e. 0.1 to at most 10% by weight, based on the total mass of comonomers A), B) and if appropriate C) and D). Solvents are to be understood as meaning substances inert under the conditions of the copolymerization and the esterification or amide formation, in particular aliphatic and aromatic hydrocarbons, such as, for example, cyclohexane, n-heptane, isododecane, benzene, toluene, ethylbenzene, xylene as isomer mixture, meta-xylene, ortho-xylene. If, in the reaction with E), no acidic catalyst is used, or if the reaction with E) is dispensed with, then the free-radical copolymerization and, if appropriate, reaction with E) can also be carried out in solvents selected from ketones, such as, for example, acetone, methyl ethyl ketone, or cyclic or noncyclic ethers, such as, for example, tetrahydrofuran or di-n-butyl ether.

The copolymerization and, if appropriate, the reaction with E) is preferably carried out with the exclusion of oxygen, for example in a nitrogen or argon atmosphere, preferably in a stream of nitrogen.

Preferably, the temperature for the copolymerization of A), B) and if appropriate C) and D) is in the range from 80 to 300° C., preferably 90 to 200° C.

The pressure is, for example, in the range from 1 to 15 bar, preferably 1 to 10 bar.

Regulators can be used, for example $C_1$-$C_4$-aldehydes, formic acid and organic compounds comprising SH groups, such as 2-mercaptoethanol, 2-mercaptopropanol, mercaptoacetic acid, tert-butyl mercaptan, n-dodecyl mercaptan. Polymerization regulators are generally used in amounts of from 0.1 to 10% by weight, based on the total mass of the comonomers used. Preference is given to working without the use of regulators.

During the copolymerization, one or more polymerization inhibitors can be added in small amounts, for example hydroquinone monomethyl ether. Polymerization inhibitor can advantageously be metered in with B) and if appropriate C) and D). Suitable amounts of polymerization inhibitor are 0.01 to 1% by weight, preferably 0.05 to 0.5% by weight, calculated on the mass of all of the comonomers. The addition of polymerization inhibitor is preferred particularly if the copolymerization is carried out at temperatures above 80° C.

When the addition of A), B) and if appropriate C) and D), if appropriate E), and if appropriate initiator is complete, the mixture can be left to afterreact.

The reaction with E) can be carried out in the absence or presence of catalysts, in particular acidic catalysts, such as, for example, sulfuric acid, methanesulfonic acid, p-toluenesulfonic acid, n-dodecylbenzenesulfonic acid, hydrochloric acid or acid ion exchangers.

In a further variant of the described method, the reaction with E) is carried out in the presence of an entrainer which forms an azeotrope with water forming, if appropriate, during the reaction.

In general, under the conditions of the above-described steps, E) reacts completely or to a certain percentage with the carboxyl groups of the anhydrides A) and, if appropriate, the carboxyl groups from D). In general, less than 40 mol % remain as unreacted E).

It is possible, through methods known per se, such as, for example, extraction, to separate off unreacted E) from copolymer obtainable by the preparation method according to the invention.

In one embodiment, it is possible to dispense with the further step of separating off unreacted E) from the prepared copolymers. In this embodiment, copolymers are used together with a certain percentage of unreacted E) for the treatment of fibrous substrates.

The above-described copolymerization of A), B) and if appropriate C) and D) gives copolymers. The resulting copolymers can be subjected to purification by conventional methods, for example reprecipitation or extractive removal of unreacted monomers. If a solvent or precipitant has been used, it is possible to remove this once copolymerization is complete, for example by distillation.

For the purposes of the present invention, copolymer prepared as described above can be contacted with water, and the amount of added water is calculated so that dispersions according to the invention are obtained which have a water content in the range from 30 to 99.5% by weight, based on the total mass of auxiliaries.

In one embodiment, after the free-radical copolymerization and, if appropriate, the reaction with E), water is added, where the water can also comprise Brønsted acid or preferably Brønsted base. Examples of Brønsted acids are sulfuric acid, hydrochloric acid, tartaric acid and citric acid. Examples of Brønsted bases are alkali metal hydroxide, such as, for example, NaOH and KOH, alkali metal carbonate, such as, for example, $Na_2CO_3$ and $K_2CO_3$, alkali metal hydrogencarbonate, such as, for example, $NaHCO_3$ and $KHCO_3$, ammonia, amines, such as, for example, trimethylamine, triethylamine, diethylamine, ethanolamine, N,N-diethanolamine, N,N,N-triethanolamine, N-methylethanolamine. The concentration of Brønsted acid or preferably Brønsted base is generally 1 to 20% by weight, based on the sum of water and Brønsted acid or water and Brønsted base.

Water can be added during the free-radical copolymerization, although it is preferably added only towards the end of the free-radical copolymerization. If the free-radical copolymerization and the reaction with E) has been carried out in the presence of solvents, then it is preferred to firstly remove solvents, for example by distillation, and only then to contact with water.

As a result of the contacting with water, which, if appropriate, can comprise Brønsted acid or preferably Brønsted base, the carboxylic acid anhydride groups present in the copolymer Ca) can be partially or completely hydrolyzed. After the contacting with water, which can, if appropriate, comprise Brønsted acid or preferably Brønsted base, the mixture can be left to afterreact at temperatures in the range from 20 to 120° C., preferably up to 100° C., for a period of from 10 minutes to 48 hours.

The isoalkane mixtures A) to be used according to the invention are likewise suitable in pharmaceutical preparations of any type, e.g. as oil bodies, for modifying the rheological properties, and as solubilizer.

The invention therefore further provides a pharmaceutical composition comprising A) at least one isoalkane mixture, as defined above,
B) at least one pharmaceutically acceptable active ingredient and
C) if appropriate at least one further pharmaceutically acceptable active ingredient or auxiliary different from B).

In a further suitable embodiment, the pharmaceutical compositions comprise, as component A), at least one high $C_{16}$-containing isoalkane mixture, as defined above.

The formulation base of the pharmaceutical compositions according to the invention preferably comprises pharmaceutically acceptable auxiliaries. Of pharmaceutical acceptability are the auxiliaries known for use in the field of pharmacy, food technology and related fields, in particular the auxiliaries listed in the relevant pharmacopoeia (e.g. DAB Ph. Eur. BP NF), and other auxiliaries whose properties do not preclude a physiological use.

Suitable auxiliaries may be: glidants, wetting agents, emulsifying and suspending agents, preservatives, antioxidants, antiirritants, chelating agents, emulsion stabilizers, film formers, gel formers, odor masking agents, resins, hydrocolloids, solvents, solubility promoters, neutralizing agents, permeation accelerators, pigments, quaternary ammonium compounds, refatting and superfatting agents, ointment, cream or oil base substances, silicone derivatives, stabilizers, sterilizing agents, propellants, drying agents, opacifiers, thickeners, waxes, emollients, white oils. One embodiment in this regard is based on specialist knowledge, as represented, for example, in Fiedler, H. P. Lexikon der Hilfsstoffe für Pharmazie, Kosmetik und angrenzende Gebiete, [Lexikon of Auxiliaries for Pharmacy, Cosmetics and Related Fields], 4th edition, Aulendorf: ECV-Editio-Kantor-Verlag, 1996.

To prepare pharmaceutical compositions according to the invention, the active ingredients can be mixed or diluted with a suitable auxiliary (excipient). Excipients may be solid, semisolid or liquid materials which can serve as vehicles, carriers or medium for the active ingredient. The admixing of further auxiliaries takes place, if desired, in the manner known to the person skilled in the art. In particular, these are aqueous solutions or solubilizates for oral or parenteral application. Furthermore, the copolymers to be used according to the invention are also suitable for use in oral administration forms such as tablets, capsules, powders, solutions. Here, they can make the drug available with increased bioavailability. In the case of parenteral application, besides solubilizers, it is also possible to use emulsions, for example fatty emulsions. The isoalkane mixtures A) according to the invention are also suitable for this purpose in order to process a drug that is sparingly soluble in, for example, aqueous media.

Pharmaceutical formulations of the abovementioned type can be obtained by processing the copolymers A) to be used according to the invention with pharmaceutical active ingredients by conventional methods and using known and novel active ingredients.

The composition according to the invention can additionally comprise pharmaceutical auxiliaries and/or diluents. Cosolvents, stabilizers, preservatives are especially listed as auxiliaries.

The pharmaceutical active ingredients used are substances which are soluble or insoluble or a little soluble in water. According to DAB 9 (German Pharmacopoeia), the solubility of pharmaceutical active ingredients is graded as follows: a little soluble (soluble in 30 to 100 parts of solvent); sparingly soluble (soluble in 100 to 1000 parts of solvent); virtually insoluble (soluble in more than 10 000 parts of solvent). The active ingredients here can come from any indication area.

Of the abovementioned pharmaceutical compositions, particular preference is given to those which are formulations which can be applied parenterally.

The content of isoalkane mixture A) in the pharmaceutical compositions is, depending on the active ingredient, in the range from 0.01 to 50% by weight, preferably 0.1 to 40% by weight, particularly preferably 1 to 30% by weight, based on the total weight of the composition.

In principle, all pharmaceutical active ingredients and prodrugs are suitable for preparing the pharmaceutical compositions according to the invention. These include benzodiazepines, antihypertensives, vitamins, cytostatics—in particular taxol, anesthetics, neuroleptics, antidepressants, antibiotics, antimycotics, fungicides, chemotherapeutics, urologics, platelet aggregation inhibitors, sulfonamides, spasmolytics, hormones, immunglobulins, sera, thyroid therapeutics, psychotropics, Parkinson's drugs and other antihyperkinetics, ophthalmics, neuropathic preparations, calcium metabolism regulators, muscle relaxants, narcotics, antilipemics, hepatotherapeutics, coronary drugs, cardiac drugs, immunotherapeutics, regulatory peptides and their inhibitors, hypnotics, sedatives, gynecological drugs, gout remedies, fibrinolytics, enzyme preparations and transport proteins, enzyme inhibitors, emetics, drugs which promote circulation, diuretics, diagnostics, corticoids, cholinergics, bile duct therapeutics, antiasthmatics, broncholytics, beta receptor blockers, calcium antagonists, ACE inhibitors, arterrosclerosis drugs, antiphlogistics, anticoagulants, antihypotensive drugs, antihypoglycemic drugs, antihypertensive drugs, antifibrinolytic drugs, antiepileptic drugs, antiemetics, antidotes, antidiabetic drugs, antiarrhythmia drugs, antianemia drugs, antiallergic drugs, anthelmintics, analgesics, analeptics, aldosterone antagonists, slimming products. Examples of suitable pharmaceutical active ingredients are in particular the active ingredients specified in paragraphs 0105 to 0131 of US 2003/0157170.

The isoalkane mixtures obtainable according to the invention and by the method according to the invention are free from intrinsic odors and have an extremely wide liquid interval (at least from −70 to +200° C.). They are therefore suitable in a particularly advantageous manner as heat transfer liquid, e.g. for solar energy plants, geothermal plants, heat exchangers used industrially etc. They are further suitable as solvents for fuel additives and low-temperature fuel (e.g. as or in jet fuel(s)).

The isoalkane mixture according to the invention is also suitable as shock absorber oil. In this connection, it can be used in pure form or in a mixture with at least one further oil, e.g. a mineral oil and/or synthetic oil (e.g. polyalphaolefin). Further components such as viscosity improvers, pour-point depressants or antioxidants can likewise be added.

The invention is illustrated in more detail by reference to the following nonlimiting examples.

EXAMPLES

I. Preparation Examples

Example 1

Preparation of an Isoalkene Mixture

An oligomer as in example 3 of WO 95/14647 was prepared starting from the $C_4$ hydrocarbon mixture described therein using the catalyst described in example 1 of WO 95/14647. 2 kg of this oligomer were subjected to fractionation over an 80 cm packed column (wire-mesh coils) with a reflux ratio of 1:5. This gave:

| Fraction | Boiling interval [° C.] | Pressure [mbar] | Amount [g] | Name |
|---|---|---|---|---|
| 1a | 100-130 | 950 | 1450 | Butene dimer |
| 1b | 100-120 | 100 | 350 | Butene trimer |
| 1c | Bottom | — | 180 | Butene tetramer |

According to GC analysis, fraction 1c consisted of 7% $C_{12}$ oligomerization product, 70% $C_{16}$ oligomerization product, 17% $C_{20}$ oligomerization product, and higher homologs.

Example 2

Hydrogenation of Fraction 1c 6 l of butene tetramer 1c from example 1 and 50 g of Pd/activated carbon (10% Pd) were introduced into a 9 l stirred pressurized container. Firstly, up to a maximum of 50 bar (5 MPa) of hydrogen was injected, such that the temperature did not exceed 50° C. Then, at 50° C., the hydrogen pressure was increased to 200 bar (20 MPa) and the mixture was after-hydrogenated for 2 hours. When hydrogenation was complete, the catalyst was separated off firstly over a fluted filter and then over a short column containing $Al_2O_3$. This gave 4.4 kg of a clear, pale, odorless liquid.

$^1$H-NMR (16 scans, 400 MHz, 10% in $CDCl_3$): no signals in the range δ 7.0-2.5 ppm detectable; 48% of the integral in the range δ 0.6-1 ppm.

Example 3

Hydrogenation of Fraction 1a 2 l of a butene dimer 1a from example 1 and 20 g of Pd/activated carbon (10% Pd) were introduced into a 3.5 l stirred pressurized container. Firstly, up to a maximum of 20 bar (2 MPa) of hydrogen was injected, such that the temperature did not exceed 50° C. Then, at 50° C., the hydrogen pressure was increased to 200 bar (20 MPa) and the mixture was after-hydrogenated for 2 hours. When hydrogenation was complete, the catalyst was separated off firstly over a fluted filter and then over a short column containing $Al_2O_3$. This gave 1.2 kg of a clear, pale, odorless liquid.

$^1$H-NMR (16 scans, 400 MHz, 10% in $CDCl_3$): no signals in the range δ 7.0-2.5 ppm detectable; 53% of the integral in the range δ 0.6-1 ppm.

Example 4

Hydrogenation of Fraction 1b 2 l of a butene trimer 1b from example 1 and 20 g of Pd/activated carbon (10% Pd) were introduced into a 3.5 l stirred pressurized container. Firstly, up to a maximum of 20 bar (2 MPa) of hydrogen was injected, such that the temperature did not exceed 50° C. Then, at 50° C., the hydrogen pressure was increased to 200 bar (20 MPa) and the mixture was after-hydrogenated for 2 hours. When hydrogenation was complete, the catalyst was separated off firstly over a fluted filter and then over a short column containing $Al_2O_3$. This gave 1.2 kg of a clear, pale, odorless liquid. 1.2 kg of a clear, pale, odorless liquid.

$^1$H-NMR (16 scans, 400 MHz, 10% in $CDCl_3$): no signals in the range δ 7.0-2.5 ppm detectable; 51% of the integral in the range δ 0.6-1 ppm.

Example 5

Comparative Example, in Accordance with Example 5 of WO 2004/091555)

800 g of isobutene and 200 g of 1-butene were initially introduced into a 3 l stirred pressurized container, and also 100 g of Lewatit® SPC 112. (In contrast to WO 2004/091555, the ion exchanger resin was converted beforehand into the active H$^+$ form with 10% $H_2SO_4$, washed thoroughly with $H_2O$ and dried. Without this catalyst activation, no conversion was achieved.). The mixture was stirred for 3 hours at 100° C., a maximum pressure of 20 bar (2 MPa) being achieved. The reactor contents were discharged, separated from the catalyst and degassed on a rotary evaporator at 40° C./100 mbar (0.02 MPa). This gave 815 g of a water-pale, low viscosity liquid with an olefinic odor.

$^1$H-NMR (16 scans, 400 MHz, 10% in $CDCl_3$): 7.7% of the integral in the olefin range δ 5.5-4.5 ppm 770 g of the above olefin mixture and 5 g of Pd/activated carbon (10% Pd) were introduced into a 3 l stirred pressurized container. Firstly, up to a maximum of 20 bar (2 MPa) of hydrogen was injected, such that the temperature does not exceed 50° C. Then, at 100° C., the hydrogen pressure is increased to 200 bar (20 MPa) and the mixture is hydrogenated for a total of 12 hours. When hydrogenation was complete, the catalyst was separated off firstly over a fluted filter and then over a short column containing $Al_2O_3$. This gave 670 g of a clear, pale liquid with a slight terpene odor.

$^1$H-NMR (16 scans, 400 MHz, 10% in $CDCl_3$): no signals in the range δ 7.0-2.5 ppm detectable; 83% of the integral in the range δ 0.6-1 ppm.

Table 1 gives the degree of branching B (=number of branches/C atom), and the integral in the range δ 0.6-1 ppm of the isoalkane mixtures from examples 2, 3, 4 and 5. Squalane serves as control.

TABLE 1

| Example | Isoalkane mixture | Integral 0.6-1 ppm | Branches/C |
|---|---|---|---|
| 2 | Hydrogenated butene tetramer | 48% | 0.21 |
| 3 | Hydrogenated butene dimer | 53% | 0.15 |
| 4 | Hydrogenated butene trimer | 51% | 0.2 |
| 5 (comparison) | Example 5 from WO 2004/091555 | 83% | 0.38 |
| Control squalane | | 40% | 0.2 |

II. Spreading Behavior

The spreading values given below were determined by the following method: A piece of filter paper (filter paper grade 1243/90, white, 500×500 mm sheet, manufacturer: Pörringer, ca. 200×200 mm) is placed in freely suspended form onto a watchglass or a Petri dish, and 10 μl of the lipid to be measured is placed in the middle. After 10 minutes, the lipid-wetted area is marked, cut out and weighed. The same method is used with the internal standard (Paraffinum perliquidum). The relative spreading value is calculated from the values obtained by the following formula:

relative spreading value=(area of measured substance×100)/area of Paraffinum perliquidum

TABLE 2

| Oil (trade names) | Relative spreading value [%] | INCI/chemical name/manufacturer |
|---|---|---|
| Abil 350 | 55 | Dimethicone |
| Panalane L14E | 82 | Hydrogenated polyisobutene |
| Polysynlan | 97 | Hydrogenated polyisobutene |
| DC 245 fluid | 109 | Cyclopentasiloxane |
| Finsolv TN | 109 | $C_{12-15}$ Alkyl benzoate |
| Fitoderm | 111 | Squalane |
| IPP | 111 | Isopropyl palmitate |
| IPM | 113 | Isopropyl myristate |
| Cetiol CC | 113 | Dicaprylyl carbonate |
| Creasil ISO 20 | 122 | Hydrogenated polyisobutene |
| Sophim MC30 | 127 | Hydrogenated polyisobutene |
| Permethyl 101A | 134 | Isohexadecane |
| Isohexadecane | 152 | Isohexadecane |
| Isoalkane mixture according to the invention from example 2 | 156 | |

III. Application Examples

Application Examples 1-3

Skin Cream

Application Example 1

A water/oil cream emulsion (skin cream A) was prepared according to the following formulation:

| | CTFA Name | % by wt. |
|---|---|---|
| Cremophor ® A6 (BASF AG) | Ceteareth-6 (stearyl alcohol ethoxylate) and stearyl alcohol | 2.0 |
| Cremophor ® A25 (BASF AG) | Ceteareth-25 (fatty alcohol ethoxylate) | 2.0 |
| Lanette ® O | Cetearyl alcohol | 2.0 |
| Imwitor ® 960K | Glyceryl stearate SE | 3.0 |
| Isoalkane mixture from example 2 | | 4.0 |
| Luvitol ® EHO (BASF AG) | Cetearyl octanoate (2-ethylhexanoic acid cetylstearyl ester) | 3.0 |
| ABIL ® 350 (Goldschmidt) | Dimethicone (polydimethylsiloxane) | 1.0 |
| Amerchol ® L101 (Amerchol Edison) | Mineral oil and lanolin alcohol | 3.0 |
| Veegum Ultra | Magnesium aluminum silicate | 0.5 |
| 1,2-Propylene glycol | Propylene glycol | 5.0 |
| Abiol | Imidazolindinylurea | 0.3 |
| Phenoxyethanol | | 0.5 |
| D-Panthenol USP | | 1.0 |
| Polymer vinylpyrrolidone/stearyl methacrylate 70/30% by wt. (K value 50; 1% in isopropanol) | | 0.5 |
| Water | | ad 100 |

Application Example 2 and Application Example 3

Application example 1 was repeated but using the isoalkane mixture from example 3 or from example 4, respectively, instead of the isoalkane mixture from example 2.

Application Examples 4-6

Moisturizing Formulation

Application Example 4

| | CTFA-Name | % by wt. |
|---|---|---|
| Cremophor ® A6 (BASF AG) | Ceteareth-6 (stearyl alcohol ethoxylate) and stearyl alcohol | 2.0 |
| Cremophor ® A25 (BASF AG) | Ceteareth-25 (fatty alcohol ethoxylate) | 2.0 |
| Isoalkane mixture from example 2 | | 10 |
| Lanette ® O | Cetearyl alcohol | 2.0 |
| Stearic acid | | 3.0 |
| Nip-Nip - (Nipa Laboratories Ltd., USA) | Methyl and propyl 4-hydroxybenzoate (7:3) | 0.5 |
| Abiol | Imidazolindinylurea | 0.5 |
| Polymer vinylpyrrolidone/stearyl methacrylate 80/20% by wt. (K value 25; 1% in isopropanol) | | 3.0 |
| Water | | ad 100 |

To prepare the formulation, both phases were heated to 80° C., phase a) and b) (phase b=water) were stirred in, homogenized and stirred while cold, and then adjusted to pH 6 with 10% strength aqueous NaOH solution.

Application Example 5 and Application Example 6

Application example 4 was repeated but using the isoalkane mixture from example 3 or from example 4, respectively, instead of the isoalkane mixture from example 2.

Application Examples 7-9

O/W Cream for Skin Moisturization

Application Example 7

| Additive | % by wt. |
|---|---|
| Glycerol monostearate | 2.0 |
| Cetyl alcohol | 3.0 |
| Isoalkane mixture from example 2 | 15.0 |
| Vaseline | 3.0 |
| Caprylic/capric triglyceride | 4.0 |
| Octyldodecanol | 2.0 |
| Hydrogenated coconut fat | 2.0 |
| Cetyl phosphate | 0.4 |
| Polymer vinylpyrrolidone/acrylic acid/stearyl methacrylate 60/5/35% by wt. (K value 41; 1% in isopropanol) | 3.0 |
| Glycerol | 3.0 |
| Sodium hydroxide | q.s. |
| Perfume oil | q.s. |
| Preservative | q.s. |
| Water | ad 100 |

Application Example 8 and Application Example 9

Application example 7 was repeated but using the isoalkane mixture from example 3 or from example 4, respectively, instead of the isoalkane mixture from example 2.

Application Examples 10-12

O/W Lotion

Application Example 10

| Additive | % by wt. |
|---|---|
| Stearic acid | 1.5 |
| Sorbitan monostearate | 1.0 |
| Sorbitan monooleate | 1.0 |
| Isoalkane mixture from example 2 | 7.0 |
| Cetyl alcohol | 1.0 |
| Polydimethylsiloxane | 1.5 |
| Glycerol | 3.0 |
| Polymer vinylpyrrolidone/acrylic acid/stearyl methacrylate 50/10/40% by wt. (K value 36; 1% in isopropanol) | 0.5 |
| Perfume oil | q.s. |
| Preservative | q.s. |
| Water | ad 100 |

Application Example 11 and Application Example 12

Application example 10 was repeated but using the isoalkane mixture from example 3 or from example 4, respectively, instead of the isoalkane mixture from example 2.

Application Examples 13-15

W/O Lotion

Application Example 13

| Additive | % by wt. |
|---|---|
| PEG-7-hydrogenated castor oil | 4.0 |
| Wool wax alcohol | 1.5 |
| Beeswax | 3.0 |
| Triglyceride, liquid | 5.0 |
| Vaseline | 9.0 |
| Ozokerite | 4.0 |
| Isoalkane mixture from example 2 | 4.0 |
| Glycerol | 2.0 |
| Polymer vinylpyrrolidone/acrylic acid/stearyl methacrylate 80/10/10% by wt. (K value 45; 1% in isopropanol) | 10.0 |
| Magnesium sulfate*$7H_2O$ | 0.7 |
| Perfume oil | q.s. |
| Preservative | q.s. |
| Water | ad 100 |

Application Example 14 and Application Example 15

Application example 13 was repeated but using the isoalkane mixture from example 3 or from example 4, respectively, instead of the isoalkane mixture from example 2.

Application Example 16-18

Hydrogel for Skincare

Application Example 16

| Additive | % by wt. |
|---|---|
| Polymer vinylpyrrolidone/acrylic acid/stearyl methacrylate 50/20/30% by wt. (K value 36; 1% in isopropanol) | 20.0 |
| Sorbitol | 2.0 |
| Isoalkane mixture from example 2 | 3.0 |
| Polyethylene glycol 400 | 5.0 |
| Ethanol | 1.0 |
| Perfume oil | q.s. |
| Preservative | q.s. |
| Water | ad 100 |

Application Example 17 and Application Example 18

Application example 16 was repeated but using the isoalkane mixture from example 3 or from example 4, respectively, instead of the isoalkane mixture from example 2.

Application Examples 19-21

Liquid Soap

Application Example 19

| Additive | % by wt. |
|---|---|
| Coconut fatty acid, potassium salt | 15 |
| Potassium oleate | 3 |
| Isoalkane mixture from example 2 | 5 |
| Polymer vinylpyrrolidone/stearyl methacrylate 70/30% by wt. (K value 47; 1% in isopropanol) | 2 |
| Glycerol stearate | 1 |
| Ethylene glycol distearate | 2 |
| Specific additives, complexing agents, fragrances, water | ad 100 |

Application Example 20 and Application Example 21

Application example 19 was repeated but using the isoalkane mixture from example 3 or from example 4, respectively, instead of the isoalkane mixture from example 2.

Application Examples 22-24

W/O Sunscreen Emulsion

Application Example 22

| Additive | % by wt. |
|---|---|
| Magnesium stearate | 0.5 |
| Aluminum stearate | 0.5 |
| Hydrogenated castor oil, 7 EO | 6.0 |
| Polymer vinylpyrrolidone/stearyl methacrylate 70/30% by wt. (K value 47; 1% in isopropanol) | 5.0 |
| Isoalkane mixture from example 2 | 1.0 |
| Cetylstearyl 2-ethylhexanoate | 10.0 |
| 2-hydroxy-4-methoxybenzophenone | 2.0 |
| Polyethoxyethyl 4-bis(polyethoxy)aminobenzoate | 5.0 |
| α-Bisabolol | 0.2 |
| 1,2-Propylene glycol | 3.0 |
| Perfume oil | q.s. |
| Preservative | q.s. |
| Water | ad 100 |

Application Example 23 and Application Example 24

Application example 22 was repeated but using the isoalkane mixture from example 3 or from example 4, respectively, instead of the isoalkane mixture from example 2.

Application Examples 25-27

Sunscreen Oil

Application Example 25

| Additive | % by wt. |
|---|---|
| Polymer vinylpyrrolidone/stearyl methacrylate 70/30% by wt. (K value 45; 1% in isopropanol) | 10.0 |
| 3-(4'-Methyl)benzylidenebornan-2-one | 2.5 |
| 2-Hydroxy-4-methoxybenzophenone | 5.5 |
| Caprylic/capric triglyceride | 10.0 |
| Dibutyl adipate | 22.5 |
| Isopropyl myristate | 7.5 |
| Isoalkane mixture from example 2 | 42.0 |

Application Example 26 and Application Example 27

Application example 25 was repeated but using the isoalkane mixture from example 3 or from example 4, respectively, instead of the isoalkane mixture from example 2.

Application Examples 28-57

PIT—Emulsions

Application Examples 28-32

| Additive | App. Ex. 28 | App. Ex. 29 | App. Ex. 30 | App. Ex. 31 | App. Ex. 32 |
|---|---|---|---|---|---|
| Glycerol monostearate self-emulsifying | 0.50 | | 3.00 | 2.00 | 4.00 |
| Polyoxyethylene(12)cetylstearyl ether | | 5.00 | | 1.00 | 1.50 |
| Polyoxyethylene(20)cetylstearylether | | | | 2.00 | |
| Polyoxyethylene(30)cetylstearylether | 5.00 | | 1.00 | | |
| Stearyl alcohol | | | 3.00 | | 0.50 |
| Cetyl alcohol | 2.50 | 1.00 | | 1.50 | |
| 2-Ethylhexyl methoxycinnamate | | | | 5.00 | 8.00 |
| 2,4-bis(4-(2-ethylhexyloxy)-2-hydroxyl)phenyl)-6-(4-methoxyphenyl)(1,3,5)-triazine | | 1.50 | | 2.00 | 2.50 |
| Butyldimethoxydibenzoylmethane | | | 2.00 | | |
| Diethylhexylbutamidotriazone | 1.00 | 2.00 | | 2.00 | |
| Ethylhexyltriazone | 4.00 | | 3.00 | 4.00 | |
| 4-Methylbenzylidenecamphor | | 4.00 | | | 2.00 |
| Octocrylene | | 4.00 | | | 2.50 |
| Phenylene-1,4-bis(monosodium, 2-benzimidazyl-5,7)-disulfonic acid | | | 0.50 | | 1.50 |

-continued

| Additive | App. Ex. 28 | App. Ex. 29 | App. Ex. 30 | App. Ex. 31 | App. Ex. 32 |
|---|---|---|---|---|---|
| Phenylbenzimidazolesulfonic acid | 0.50 | | | 3.00 | |
| $C_{12\text{-}15}$-Alkylbenzoate | | 2.50 | | | 5.00 |
| Titanium dioxide | 0.50 | 1.00 | | 3.00 | 2.00 |
| Zinc oxide | 2.00 | | 3.00 | 0.50 | 1.00 |
| Dicaprylyl ether | | | 3.50 | | |
| Butylene glycol dicaprylate/dicaprate | 5.00 | | | 6.00 | |
| Dicaprylyl carbonate | | | 6.00 | | 2.00 |
| Dimethicone polydimethylsiloxane | | 0.50 | 1.00 | | |
| Phenylmethylpolysiloxane | 2.00 | | | 0.50 | 0.50 |
| Shea butter | | 2.00 | | | 0.50 |
| PVP Hexadecene copolymer | 0.50 | | | 0.50 | 1.00 |
| Glycerol | 3.00 | 7.50 | 5.00 | 7.50 | 2.50 |
| Tocopherol acetate | 0.50 | | 0.25 | | 1.00 |
| Isoalkane mixture as in example 2 | 0.2 | 1.1 | 0.3 | 0.8 | 0.5 |
| Alpha-glucosylrutin | 0.10 | | 0.20 | | |
| Preservative | q.s. | q.s. | q.s. | q.s. | q.s. |
| Ethanol | 3.00 | 2.00 | 1.50 | | 1.00 |
| Perfume | q.s. | q.s. | q.s. | q.s. | q.s. |
| Water | ad 100 | ad 100 | ad 100 | ad 100 | ad 100 |

App. Ex. Application example

Application Examples 33-37 and Application Examples 38-42

Application examples 28-32 were repeated but using the isoalkane mixture from example 3 or from example 4, respectively, instead of the isoalkane mixture from example 2.

Application Examples 43-47

| Additive | App. Ex. 43 | App. Ex. 44 | App. Ex. 45 | App. Ex. 46 | App. Ex. 47 |
|---|---|---|---|---|---|
| Glycerol monostearate self-emulsifying | 0.50 | | 3.00 | 2.00 | 4.00 |
| Polyoxyethylene(12) cetylstearyl ether | | 5.00 | | 1.00 | 1.50 |
| Polyoxyethylene(20)cetylstearyl ether | | | | 2.00 | |
| Polyoxyethylene(30)cetylstearyl ether | 5.00 | | 1.00 | | |
| Stearyl alcohol | | | 3.00 | | 0.50 |
| Cetyl alcohol | 2.50 | 1.00 | | 1.50 | |
| 2-ethylhexyl methoxycinnamate | | | | 5.00 | 8.00 |
| 2,4-bis(4-(2-ethylhexyloxy)-2-hydroxyl)phenyl)-6-(4-methoxyphenyl)-(1,3,5)-triazine | | 1.50 | | 2.00 | 2.50 |
| Butyldimethoxydibenzoylmethane | | | 2.00 | | |
| Dimethicodiethylbenzalmalonate | | 6.50 | | | |
| Diethylhexylbutamidotriazone | 1.00 | 2.00 | | 2.00 | |
| Ethylhexyltriazone | 4.00 | | 3.00 | 4.00 | |
| Hexyl 2-(4'-(diethylamino)-2'-hydroxybenzoyl)benzoate | 1.50 | 4.00 | 3.50 | 5.00 | 2.00 |
| Octocrylene | | 4.00 | | | 2.50 |
| Phenylene-1,4-bis(monosodium) 2-benzimidazyl-5,7-disulfonic acid | | | 0.50 | | 1.50 |
| Phenylbenzimidazolesulfonic acid | 0.50 | | | 3.00 | |
| $C_{12\text{-}15}$-Alkyl benzoate | | 2.50 | | | 5.00 |
| Dicaprylyl ether | | | 3.50 | | |
| Butylene glycol dicaprylate/dicaprate | 5.00 | | | 6.00 | |
| Dicaprylyl carbonate | | | 6.00 | | 2.00 |
| Dimethicone polydimethylsiloxane | | 0.50 | 1.00 | | |
| Phenylmethylpolysiloxane | 2.00 | | | 0.50 | 0.50 |
| Shea butter | | 2.00 | | | 0.50 |
| PVP Hexadecene copolymer | 0.50 | | | 0.50 | 1.00 |
| Glycerol | 3.00 | 7.50 | 5.00 | 7.50 | 2.50 |
| Tocopherol acetate | 0.50 | | 0.25 | | 1.00 |
| Isoalkane mixture as in example 2 | 0.10 | 1.00 | 0.20 | 0.50 | 1.50 |
| Diethylhexyl 2,6-naphthalate | | | 2.00 | | |
| Alpha-glucosylrutin | 0.10 | | 0.20 | | |
| DMDM Hydantoin | | 0.25 | | 0.60 | 0.45 |
| Paraben | 0.15 | | 0.50 | 0.30 | |
| Konkaben LMB ® | 0.20 | | 0.40 | | |
| Trisodium EDTA | | 0.80 | | | 1.00 |
| Phenoxyethanol | 0.30 | | | 0.20 | 0.50 |

| Additive | App. Ex. 43 | App. Ex. 44 | App. Ex. 45 | App. Ex. 46 | App. Ex. 47 |
|---|---|---|---|---|---|
| Ethanol | 3.00 | 2.00 | 1.50 | | 1.00 |
| Perfume | q.s. | q.s. | q.s. | q.s. | q.s. |
| Water | ad 100 | ad 100 | ad 100 | ad 100 | ad 100 |

App. Ex. Application example

Application Examples 48-52 and Application Examples 53-57

Application examples 43-47 were repeated but using the isoalkane mixture from example 3 or from example 4, respectively, instead of the isoalkane mixture from example 2.

Application Examples 58-117

O/W Emulsions

Application Examples 58-62

| Additive | App. Ex. 58 | App. Ex. 59 | App. Ex. 60 | App. Ex. 61 | App. Ex. 62 |
|---|---|---|---|---|---|
| Glyceryl stearate citrate | | | 2.00 | | 2.00 |
| Glyceryl stearate self-emulsifying | 4.00 | 3.00 | | | |
| PEG-40 stearate | 1.00 | | | | |
| Polyglyceryl-3-methylglucose distearate | | | | 3.00 | |
| Sorbitan stearate | | | | | 2.00 |
| Stearic acid | | 1.00 | | | |
| Stearyl alcohol | | | 5.00 | | |
| Cetyl alcohol | 3.00 | 2.00 | | 3.00 | |
| Cetylstearyl alcohol | | | | | 2.00 |
| Caprylic/capric triglyceride | 5.00 | 3.00 | 4.00 | 3.00 | 3.00 |
| Octyldodecanol | | | 2.00 | | 2.00 |
| Dicaprylyl ether | | 4.00 | | 2.00 | 1.00 |
| Paraffinum liquidum | 5.00 | 2.00 | | 3.00 | |
| Titanium dioxide | | | 1.00 | | |
| Octocrylene | | | 3.50 | | |
| Butyldimethoxydibenzoylmethane | | | 0.50 | | |
| Isoalkane mixture as in example 2 | 0.10 | 0.20 | 0.70 | 0.15 | 1.00 |
| Tocopherol | 0.10 | | | | 0.20 |
| Biotin | | | 0.05 | | |
| Ethylenediaminetetraacetic acid trisodium | 0.1 | | 0.10 | 0.1 | |
| Preservative | q.s. | q.s. | q.s. | q.s. | q.s. |
| Polyacrylic acid | 3.00 | 0.1 | | 0.1 | 0.1 |
| Sodium hydroxide solution 45% | q.s | q.s. | q.s. | q.s. | q.s. |
| Glycerol | 5.00 | 3.00 | 4.00 | 3.00 | 3.00 |
| Butylene glycol | | 3.00 | | | |
| Perfume | q.s. | q.s. | q.s. | q.s. | q.s. |
| Water | ad 100 | ad 100 | ad 100 | ad 100 | ad 100 |

App. Ex. Application example

Application Examples 63-67 and Application Examples 68-72

Application examples 58-62 were repeated but using the isoalkane mixture from example 3 or from example 4, respectively, instead of the isoalkane mixture from example 2.

Application Examples 73-77

| Additive | App. Ex. 73 | App. Ex. 74 | App. Ex. 75 | App. Ex. 76 | App. Ex. 77 |
|---|---|---|---|---|---|
| Glyceryl stearate citrate | | 2.00 | 2.00 | | |
| Glyceryl stearate self-emulsifying | 5.00 | | | | |
| Stearic acid | | | | 2.50 | 3.50 |
| Stearyl alcohol | 2.00 | | | | |
| Cetyl alcohol | | | | 3.00 | 4.50 |
| Cetylstearyl alcohol | | 3.00 | 1.00 | | 0.50 |
| $C_{12-15}$-alkylbenzoate | | 2.00 | 3.00 | | |
| Caprylic/capric triglyceride | 2.00 | | | | |
| Octyldodecanol | 2.00 | 2.00 | | 4.00 | 6.00 |
| Dicaprylyl ether | | | | | |
| Paraffinum liquidum | | 4.00 | 2.00 | | |
| Cyclic dimethylpolysiloxane | | | | 0.50 | 2.00 |
| Dimethicone polydimethyl siloxane | 2.00 | | | | |
| Titanium dioxide | 2.00 | | | | |
| 4-Methylbenzylidenecamphor | 1.00 | | | | |
| Ethylhexyltriazone | | | | | 2.00 |
| Butyldimethoxydibenzoylmethane | 0.50 | | | | 0.50 |
| Isoalkane mixture as in example 2 | 0.30 | 0.10 | 1.00 | 0.50 | 0.10 |
| Tocopherol | | | | | 0.10 |
| Ethylenediaminetetraacetic acid trisodium | | | 0.20 | | 0.20 |
| Preservative | q.s. | q.s. | q.s. | q.s. | q.s. |
| Xanthan gum | | | 0.20 | | |
| Polyacrylic acid | 0.15 | 0.1 | | 0.05 | 0.05 |
| Sodium hydroxide solution 45% | q.s. | q.s. | q.s. | q.s. | q.s. |
| Glycerol | 3.00 | | 3.00 | 5.00 | 3.00 |
| Butylene glycol | | 3.00 | | | |
| Ethanol | | 3.00 | | 3.00 | |
| Perfume | q.s. | q.s. | q.s. | q.s. | q.s. |
| Water | ad 100 | ad 100 | ad 100 | ad 100 | ad 100 |

App. Ex. Application example

Application Examples 78-82 and Application Examples 83-87

Application examples 73-77 were repeated but using the isoalkane mixture from example 3 or from example 4, respectively, instead of the isoalkane mixture from example 2.

Application Examples 88-92

| Additive | App. Ex. 88 | App. Ex. 89 | App. Ex. 90 | App. Ex. 91 | App. Ex. 92 |
|---|---|---|---|---|---|
| Glyceryl stearate citrate | | | 2.00 | | 2.00 |
| Glyceryl stearate self-emulsifying | 4.00 | 3.00 | | | |
| PEG-40 stearate | 1.00 | | | | |
| Polyglyceryl-3 methylglucose distearate | | | | 3.00 | |
| Sodium cetearyl sulphate | 0.50 | | | | 1.00 |
| Sorbitan stearate | | | | | 2.00 |
| Stearic acid | | 1.00 | | | |
| Stearyl alcohol | | | 5.00 | | |
| Cetyl alcohol | 3.00 | 2.00 | | 3.00 | |
| Cetylstearyl alcohol | | | | | 2.00 |
| Caprylic/capric triglyceride | 5.00 | 3.00 | 4.00 | 3.00 | 3.00 |
| Octyldodecanol | | | 2.00 | | 2.00 |
| Dicaprylyl ether | | 4.00 | | 2.00 | 1.00 |
| Paraffinum liquidum | 5.00 | 2.00 | | 3.00 | |
| Zinc oxide | 1.00 | | | | 2.00 |
| Titanium dioxide | | | 1.00 | | |
| Hexyl 2-(4'-(diethylamino)-2'-hydroxybenzoyl)benzoate | 0.50 | 2.50 | 3.00 | 1.50 | 5.50 |
| 2-Ethylhexyl methoxycinnamate | | 5.50 | | | |
| 2,4-bis(4-(2-ethylhexyloxy)-2-hydroxyl)phenyl)-6-(4-methoxyphenyl)-(1,3,5)-triazine | 3.00 | | 1.50 | 0.80 | |
| Diethylhexylbutamidotriazone | | 2.00 | | | 1.00 |
| Ethylhexyltriazone | 1.80 | | | | |
| Phenylene-1,4-bis(monosodium, 2-benzimidazyl-5,7-disulfonic acid) | 0.50 | | | | 0.50 |
| Phenylbenzimidazolesulfonic acid | | | 0.50 | 2.00 | |

| Additive | App. Ex. 88 | App. Ex. 89 | App. Ex. 90 | App. Ex. 91 | App. Ex. 92 |
|---|---|---|---|---|---|
| Octocrylene | | | 3.50 | | |
| Butyldimethoxydibenzoylmethane | | | 0.50 | | |
| Isoalkane mixture as in example 2 | 0.10 | 0.20 | 0.70 | 0.15 | 1.00 |
| Tocopherol | 0.10 | | | | 0.20 |
| Diethylhexyl-2,6-naphthalate | | | 3.50 | | |
| Biotin | | 0.05 | | | |
| Ethylenediaminetetraacetic acid trisodium | 0.1 | | 0.10 | 0.1 | |
| Preservative | q.s. | q.s. | q.s. | q.s. | q.s. |
| Polyacrylic acid | 3.00 | 0.1 | | 0.1 | 0.1 |
| Sodium hydroxide solution 45% | q.s | q.s. | q.s. | q.s. | q.s. |
| Glycerol | 5.00 | 3.00 | 4.00 | 3.00 | 3.00 |
| Butylene glycol | | 3.00 | | | |
| Perfume | q.s. | q.s. | q.s. | q.s. | q.s. |
| Water | ad 100 | ad 100 | ad 100 | ad 100 | ad 100 |

App. Ex. Application example

Application Examples 93-97 and Application Examples 98-102

Application examples 88-92 were repeated but using the isoalkane mixture from example 3 or from example 4, respectively, instead of the isoalkane mixture from example 2.

Application Examples 103-107

| Additive | App. Ex. 103 | App. Ex. 104 | App. Ex. 105 | App. Ex. 106 | App. Ex. 107 |
|---|---|---|---|---|---|
| Glyceryl stearate citrate | | 2.00 | 2.00 | | |
| Glyceryl stearate self-emulsifying | 5.00 | | | | |
| Stearic acid | | | | 2.50 | 3.50 |
| Stearyl alcohol | 2.00 | | | | |
| Cetyl alcohol | | | | 3.00 | 4.50 |
| Cetylstearyl alcohol | | 3.00 | 1.00 | | 0.50 |
| $C_{12\text{-}15}$-Alkylbenzoate | | 2.00 | 3.00 | | |
| Caprylic/capric triglyceride | 2.00 | | | | |
| Octyldodecanol | 2.00 | 2.00 | | 4.00 | 6.00 |
| Dicaprylyl ether | | | | | |
| Paraffinum liquidum | | 4.00 | 2.00 | | |
| Cyclic dimethylpolysiloxane | | | | 0.50 | 2.00 |
| Dimethicone polydimethylsiloxane | 2.00 | | | | |
| Titanium dioxide | 2.00 | | | | |
| 4-Methylbenzylidenecamphor | 1.00 | | | | |
| Ethylhexyltriazone | | 3.00 | | | 2.00 |
| Butyldimethoxydibenzoylmethane | 0.50 | | | | 0.50 |
| Hexyl 2-(4'-(diethylamino)-2'-hydroxybenzoyl)benzoate | 0.50 | 1.50 | 5.00 | 3.30 | 4.00 |
| Isoalkane mixture as in example 2 | 0.30 | 0.10 | 1.00 | 0.50 | 0.10 |
| 2-Ethylhexyl methoxycinnamate | 1.50 | 4.00 | | 2.50 | |
| 2,4-Bis(4-(2-ethylhexyloxy-)-2-hydroxyl)phenyl)-6-(4-methoxyphenyl)-(1,3,5)-triazine | 0.80 | | 1.50 | 2.50 | |
| Dimethicodiethylbenzalmalonate | | | 6.00 | | |
| Diethylhexylbutamidotriazone | 1.00 | 3.00 | | 2.00 | |
| Octocrylene | 4.00 | | 5.00 | | 3.50 |
| Phenylene-1,4-bis(monosodium, 2-benzimidazyl-5,7-disulfonic acid) | 0.50 | | 1.00 | | |
| Phenylbenzimidazolesulfonic acid | | 2.00 | | 1.50 | 0.50 |
| Tocopherol | | | | | 0.10 |
| Ethylenediaminetetraacetic acid trisodium | | | 0.20 | | 0.20 |
| Preservative | q.s. | q.s. | q.s. | q.s. | q.s. |
| Xanthan gum | | | 0.20 | | |
| Polyacrylic acid | 0.15 | 0.1 | | 0.05 | 0.05 |
| Sodium hydroxide solution 45% | q.s. | q.s. | q.s. | q.s. | q.s. |
| Glycerol | 3.00 | | 3.00 | 5.00 | 3.00 |
| Butylene glycol | | 3.00 | | | |
| Ethanol | | 3.00 | | 3.00 | |
| Perfume | q.s. | q.s. | q.s. | q.s. | q.s. |
| Water | ad 100 | ad 100 | ad 100 | ad 100 | ad 100 |

App. Ex. Application example

Application Examples 108-112 and Application Examples 113-117

Application examples 103-107 were repeated but using the isoalkane mixture from example 3 or from example 4, respectively, instead of the isoalkane mixture from example 2.

Application Examples 118-159

W/O Emulsions

Application Examples 118-122

| Additive | App. Ex. 118 | App. Ex. 119 | App. Ex. 120 | App. Ex. 121 | App. Ex. 122 |
|---|---|---|---|---|---|
| Cetyldimethicone copolyol | | 2.50 | | 4.00 | |
| Polyglyceryl-2 dipolyhydroxystearate | 5.00 | | | | 4.50 |
| PEG-30-dipolyhydroxystearate | | | 5.00 | | |
| 2-Ethylhexyl methoxycinnamate | | 8.00 | | 5.00 | 4.00 |
| 2,4-Bis(4-(2-ethylhexyloxy)-2-hydroxyl)phenyl)-6-(4-methoxyphenyl)-(1,3,5)-triazine | 2.00 | 2.50 | | 2.00 | 2.50 |
| Butyldimethoxydibenzoylmethane | | | 2.00 | 1.00 | |
| Diethylhexylbutamidotriazone | 3.00 | 1.00 | | | 3.00 |
| Ethylhexyltriazone | | | 3.00 | 4.00 | |
| 4-Methylbenzylidenecamphor | | 2.00 | | 4.00 | 2.00 |
| Octocrylene | 7.00 | 2.50 | 4.00 | | 2.50 |
| Diethylhexylbutamidotriazone | 1.00 | | | 2.00 | |
| Phenylene-1,4-bis(monosodium, 2-benzimidazyl-5,7-disulfonic acid) | 1.00 | 2.00 | 0.50 | | |
| Phenylbenzimidazolesulfonic acid | 0.50 | | | 3.00 | 2.00 |
| Titanium dioxide | | 2.00 | 1.50 | | 3.00 |
| Zinc oxide | 3.00 | 1.00 | 2.00 | 0.50 | |
| Paraffinum liquidum | | | 10.0 | | 8.00 |
| $C_{12-15}$-Alkylbenzoate | | | | 9.00 | |
| Dicaprylyl ether | 10.00 | | | | 7.00 |
| Butylene glycoldicaprylate/dicaprate | | | 2.00 | 8.00 | 4.00 |
| Dicaprylyl carbonate | 5.00 | | 6.00 | | |
| Dimethicone polydimethylsiloxane | | 4.00 | 1.00 | 5.00 | |
| Phenylmethylpolysiloxane | 2.00 | 25.00 | | | 2.00 |
| Shea butter | | | 3.00 | | |
| PVP Hexadecene copolymer | 0.50 | | | 0.50 | 1.00 |
| Octoxyglycerol | | 0.30 | 1.00 | | 0.50 |
| Glycerol | 3.00 | 7.50 | | 7.50 | 2.50 |
| Glycine soya | | 1.00 | 1.50 | | |
| Magnesium sulphate | 1.00 | 0.50 | | 0.50 | |
| Magnesium chloride | | | 1.00 | | 0.70 |
| Tocopherol acetate | 0.50 | | 0.25 | | 1.00 |
| Isoalkane mixture as in example 2 | 0.2 | 0.3 | 0.6 | 1 | 1.5 |
| Preservative | q.s. | q.s. | q.s. | q.s. | q.s. |
| Ethanol | 3.00 | | 1.50 | | 1.00 |
| Perfume | q.s. | q.s. | q.s. | q.s. | q.s. |
| Water | ad 100 | ad 100 | ad 100 | ad 100 | ad 100 |

App. Ex. Application example

Application Examples 123-127 and Application Examples 128-132

Application examples 118-122 were repeated but using the isoalkane mixture from example 3 or from example 4, respectively, instead of the isoalkane mixture from example 2.

Application Examples 133-134

| Additive | App. Ex. 133 | App. Ex. 134 |
|---|---|---|
| Polyglyceryl-2-dipolyhydroxystearate | 4.00 | 5.00 |
| Lanolin alcohol | 0.50 | 1.50 |
| Isohexadecane | 1.00 | 2.00 |
| Myristyl myristate | 0.50 | 1.50 |
| Vaseline | 1.00 | 2.00 |
| Butyldimethoxydibenzoylmethane | 0.50 | 1.50 |
| 4-Methylbenzylidenecamphor | 1.00 | 3.00 |
| Butylene glycol dicaprylate/dicaprate | 4.00 | 5.00 |
| Shea butter | | 0.50 |
| Butylene glycol | | 6.00 |
| Octoxyglycerol | | 3.00 |
| Glycerol | 5.00 | |
| Tocopherol acetate | 0.50 | 1.00 |
| Isoalkane mixture as in example 2 | 0.50 | 0.20 |
| Trisodium EDTA | 0.20 | 0.20 |
| Preservative | q.s. | q.s. |
| Ethanol | | 3.00 |
| Perfume | q.s. | q.s. |
| Water | ad 100 | ad 100 |

App. Ex. Application example

Application Examples 135-136 and Application Examples 137-138

Application examples 133-134 were repeated but using the isoalkane mixture from example 3 or from example 4, respectively, instead of the isoalkane mixture from example 2.

Application Examples 139-143

| Additive | App. Ex. 139 | App. Ex. 140 | App. Ex. 141 | App. Ex. 142 | App. Ex. 143 |
|---|---|---|---|---|---|
| Cetyldimethicone copolyol | | 2.50 | | 4.00 | |
| Polyglyceryl-2 dipolyhydroxystearate | 5.00 | | | | 4.50 |
| PEG-30 dipolyhydroxystearate | | | 5.00 | | |
| Ethylhexyl methoxycinnamate | | 8.00 | | 5.00 | 4.00 |
| 2,4-Bis(4-(2-ethylhexyloxy)-2-hydroxyl)phenyl)-6-(4-methoxyphenyl)-(1,3,5)-triazine | 2.00 | 2.50 | | 2.00 | 2.50 |
| Butyldimethoxydibenzoylmethane | | | 2.00 | 1.00 | |
| Diethylhexylbutamidotriazone | 3.00 | 1.00 | | | 3.00 |
| Ethylhexyltriazone | | | 3.00 | 4.00 | |
| 4-Methylbenzylidenecamphor | | 2.00 | | | |
| Hexyl 2-(4'-(diethylamino)-2'-hydroxybenzoyl)benzoate | 0.50 | 2.50 | 4.50 | 3.00 | 1.80 |
| Octocrylene | 7.00 | 2.50 | 4.00 | | 2.50 |
| Phenylene-1,4-bis(monosodium,2-benzimidazyl-5,7-disulfonic acid) | 1.00 | 2.00 | 0.50 | | |
| Phenylbenzimidazolesulfonic acid | 0.50 | | | 3.00 | 2.00 |
| Dimethicodiethylbenzalmalonate | | | 5.50 | | |
| Titanium dioxide | | 2.00 | 1.50 | | 3.00 |
| Zinc oxide | 3.00 | 1.00 | 2.00 | 0.50 | |
| Paraffinum liquidum | | | 10.0 | | 8.00 |
| C$_{12-15}$-Alkyl benzoate | | | | 9.00 | |
| Dicaprylyl ether | 10.00 | | | | 7.00 |
| Butylene glycoldicaprylate/dicaprate | | | 2.00 | 8.00 | 4.00 |
| Dicaprylyl carbonate | 5.00 | | 6.00 | | |
| Dimethicone polydimethylsiloxane | | 4.00 | 1.00 | 5.00 | |
| Phenylmethylpolysiloxane | 2.00 | 25.00 | | | 2.00 |
| Shea butter | | | 3.00 | | |
| Diethylhexyl 2,6-naphthalate | | | 6.50 | | |
| PVP Hexadecene copolymer | 0.50 | | | 0.50 | 1.00 |
| Octoxyglycerol | | 0.30 | 1.00 | | 0.50 |
| Glycerol | 3.00 | 7.50 | | 7.50 | 2.50 |
| Glycine soya | | 1.00 | 1.50 | | |
| Magnesium sulfate | 1.00 | 0.50 | | 0.50 | |
| Magnesium chloride | | | 1.00 | | 0.70 |
| Tocopherol acetate | 0.50 | | 0.25 | | 1.00 |
| Isoalkane mixture as in example 2 | 0.10 | 0.20 | 0.50 | 0.90 | 1.00 |
| DMDM Hydantoin | | 0.25 | | 0.60 | 0.45 |
| Parabens | 0.15 | | 0.50 | 0.30 | |
| Konkaben LMB ® | 0.20 | | 0.40 | | |
| Trisodium EDTA | | 0.80 | | | 1.00 |
| Phenoxyethanol | 0.30 | | | 0.20 | 0.50 |
| Ethanol | 3.00 | 2.00 | 1.50 | | 1.00 |
| Perfume | q.s. | q.s. | q.s. | q.s. | q.s. |
| Water | ad 100 | ad 100 | ad 100 | ad 100 | ad 100 |

App. Ex. Application example

Application Examples 144-148 and Application Examples 149-153

Application examples 139-143 were repeated but using the isoalkane mixture from example 3 or from example 4, respectively, instead of the isoalkane mixture from example 2.

Application Examples 154-155

| Additive | App. Ex. 154 | App. Ex. 155 |
|---|---|---|
| Polyglyceryl-2 dipolyhydroxystearate | 4.00 | 5.00 |
| Lanolin alcohol | 0.50 | 1.50 |
| Isohexadecane | 1.00 | 2.00 |
| Myristyl myristate | 0.50 | 1.50 |
| Vaseline | 1.00 | 2.00 |
| Butyldimethoxydibenzoylmethane | 0.50 | 1.50 |
| Diethylhexylbutamidotriazone | 1.50 | 0.50 |
| Butylene glycol dicaprylate/dicaprate | 4.00 | 5.00 |
| Hexyl 2-(4'-(diethylamino)-2'-hydroxybenzoyl)benzoate | 2.50 | 4.50 |
| Shea butter | | 0.50 |
| Butylene glycol | | 6.00 |
| Octoxyglycerol | | 3.00 |
| Glycerol | 5.00 | |
| Tocopherol acetate | 0.50 | 1.00 |
| Isoalkane mixture as in example 2 | 0.10 | 0.70 |
| Trisodium EDTA | 0.20 | 0.20 |
| Preservative | q.s. | q.s. |
| Ethanol | | 3.00 |

| Additive | App. Ex. 154 | App. Ex. 155 |
|---|---|---|
| Perfume | q.s. | q.s. |
| Water | ad 100 | ad 100 |

App. Ex. Application example

Application Examples 156-157 and Application Examples 158-159

Application examples 154-155 were repeated but using the isoalkane mixture from example 3 or from example 4, respectively, instead of the isoalkane mixture from example 2.

Application Examples 160-189

Hydrodispersions

Application Examples 160-164

| Additive | App. Ex. 160 | App. Ex. 161 | App. Ex. 162 | App. Ex. 163 | App. Ex. 164 |
|---|---|---|---|---|---|
| Polyoxyethylene(20) cetylstearyl ether | 1.00 | | | 0.5 | |
| Cetyl alcohol | | | 1.00 | | |
| Sodium polyacrylate | | 0.20 | | 0.30 | |
| Acrylate/$C_{10-30}$-alkyl acrylate crosspolymer | 0.50 | | 0.40 | 0.10 | 0.10 |
| Xanthan gum | | 0.30 | 0.15 | | 0.50 |
| 2-Ethylhexyl methoxycinnamate | | | | 5.00 | 8.00 |
| 2,4-Bis(4-(2-ethylhexyloxy)-2-hydroxyl)phenyl)-6-(4-methoxyphenyl)-(1,3,5)-triazine | | 1.50 | | 2.00 | 2.50 |
| Butyldimethoxydibenzoylmethane | 1.00 | | 2.00 | | |
| Diethylhexylbutamidotriazone | | 2.00 | | 2.00 | 1.00 |
| Ethylhexyltriazone | 4.00 | | 3.00 | 4.00 | |
| 4-Methylbenzylidenecamphor | 4.00 | 4.00 | | | 2.00 |
| Octocrylene | | 4.00 | 4.00 | | 2.50 |
| Phenylene-1,4-bis(monosodium, 2-benzimidazyl-5,7-disulfonic acid | 1.00 | | 0.50 | | 2.00 |
| Phenylbenzimidazolesulfonic acid | 0.50 | | | 3.00 | |
| Titanium dioxide | 0.50 | | 2.00 | 3.00 | 1.00 |
| Zinc oxide | 0.50 | 1.00 | 3.00 | | 2.00 |
| $C_{12-15}$-Alkyl benzoate | 2.00 | 2.50 | | | |
| Dicaprylyl ether | | 4.00 | | | |
| Butylene glycol dicaprylate/dicaprate | 4.00 | | 2.00 | 6.00 | |
| Dicaprylyl carbonate | | 2.00 | 6.00 | | |
| Dimethicone polydimethylsiloxane | | | 0.50 | 1.00 | |
| Phenylmethylpolysiloxane | 2.00 | | | 0.50 | 2.00 |
| Shea butter | | 2.00 | | | |
| PVP Hexadecene copolymer | 0.50 | | | 0.50 | 1.00 |
| Octoxyglycerol | | | 1.00 | | 0.50 |
| Glycerol | 3.00 | 7.50 | | 7.50 | 2.50 |
| Glycine soya | | | 1.50 | | |
| Tocopherol acetate | 0.50 | | 0.25 | | 1.00 |
| Isoalkane mixture as in example 2 | 0.4 | 0.2 | 0.6 | 0.5 | 1 |
| Preservative | q.s. | q.s. | q.s. | q.s. | q.s. |
| Ethanol | 3.00 | 2.00 | 1.50 | | 1.00 |
| Perfume | q.s. | q.s. | q.s. | q.s. | q.s. |
| Water | ad 100 | ad 100 | ad 100 | ad 100 | ad 100 |

App. Ex. Application example

Application Examples 165-169 and Application Examples 170-174

Application examples 160-164 were repeated but using the isoalkane mixture from example 3 or from example 4, respectively, instead of the isoalkane mixture from example 2.

Application Examples 175-179

| Additive | App. Ex. 175 | App. Ex. 176 | App. Ex. 177 | App. Ex. 178 | App. Ex. 179 |
|---|---|---|---|---|---|
| Polyoxyethylene(20) cetylstearyl ether | 1.00 | | | 0.5 | |
| Cetyl alcohol | | | 1.00 | | |
| Sodium polyacrylate | | 0.20 | | 0.30 | |
| Acrylate/$C_{10-30}$-alkyl acrylate crosspolymer | 0.50 | | 0.40 | 0.10 | 0.10 |
| Xanthan gum | | 0.30 | 0.15 | | 0.50 |
| 2-Ethylhexyl methoxycinnamate | | | | 5.00 | 8.00 |
| 2,4-Bis(4-(2-ethylhexyloxy)-2-hydroxyl)phenyl)-6-(4-methoxyphenyl)-(1,3,5)-triazine | | 1.50 | 2.00 | | 2.50 |
| Dimethicodiethylbenzalmalonate | | 3.50 | | | |
| Butyldimethoxydibenzoylmethane | 1.00 | | 2.00 | | |
| Diethylhexylbutamidotriazone | | 2.00 | | 2.00 | 1.00 |
| Ethylhexyltriazone | 4.00 | | 3.00 | 4.00 | |
| 4-Methylbenzylidenecamphor | | | | | 2.00 |
| Hexyl 2-(4'-(diethylamino)-2'-hydroxybenzoyl)benzoate | 2.00 | 1.40 | 0.50 | 4.60 | 5.20 |
| Octocrylene | | 4.00 | 4.00 | | 2.50 |
| Phenylene-1,4-bis(monosodium, 2-benzimidazyl-5,7-disulfonic acid) | 1.00 | | 0.50 | | 2.00 |
| Phenylbenzimidazolesulfonic acid | 0.50 | | | 3.00 | |
| Titanium dioxide | 0.50 | | 2.00 | 3.00 | 1.00 |
| Zinc oxide | 0.50 | 1.00 | 3.00 | | 2.00 |
| $C_{12-15}$-Alkylbenzoate | 2.00 | 2.50 | | | |
| Diethylhexyl-2,6-naphthalate | 4.00 | | | | |
| Dicaprylyl ether | | 4.00 | | | |
| Butylene glycol dicaprylate/dicaprate | 4.00 | | 2.00 | 6.00 | |
| Dicaprylyl carbonate | | 2.00 | 6.00 | | |
| Dimethiconepolydimethylsiloxane | | 0.50 | 1.00 | | |
| Phenylmethylpolysiloxane | 2.00 | | | 0.50 | 2.00 |
| Shea butter | | 2.00 | | | |
| PVP Hexadecene copolymer | 0.50 | | | 0.50 | 1.00 |
| Octoxyglycerol | | | 1.00 | | 0.50 |
| Glycerol | 3.00 | 7.50 | | 7.50 | 2.50 |
| Glycine soya | | | 1.50 | | |
| Tocopherol acetate | 0.50 | | 0.25 | | 1.00 |
| Isoalkane mixture as in example 2 | 0.3 | 0.10 | 0.50 | 1.00 | 0.20 |
| DMDM Hydantoin | | 0.25 | | 0.60 | 0.45 |
| Parabene | 0.15 | | 0.50 | 0.30 | |
| Konkaben LMB ® | 0.10 | | 0.30 | | |
| Trisodium EDTA | | | 0.70 | | 1.00 |
| Phenoxyethanol | | 0.40 | | 0.20 | 0.50 |
| Ethanol | 3.00 | 2.00 | 1.50 | | 1.00 |
| Perfume | q.s. | q.s. | q.s. | q.s. | q.s. |
| Water | ad 100 | ad 100 | ad 100 | ad 100 | ad 100 |

App. Ex. Application example

Application Examples 180-184 and Application Examples 185-189

Application examples 175-179 were repeated but using the isoalkane mixture from example 3 or from example 4, respectively, instead of the isoalkane mixture from example 2.

Application Examples 191-196

Gel Cream

Application Example 191

| Additive | % by wt. |
|---|---|
| Acrylate/$C_{10-30}$-alkyl acrylate crosspolymer | 0.40 |
| Polyacrylic acid | 0.20 |
| Xanthan gum | 0.10 |
| Cetearyl alcohol | 3.00 |
| $C_{12-15}$-Alkyl benzoate | 4.00 |
| Caprylic/capric triglyceride | 3.00 |
| Ethylhexyl methoxycinnamate | 5.00 |
| Bis-ethylhexyloxyphenol methoxyphenyltriazine | 1.00 |
| Ethylhexyltriazone | 2.00 |
| Cyclic dimethylpolysiloxane | 5.00 |
| Dimethicone polydimethylsiloxane | 1.00 |
| Isoalkane mixture as in example 2 | 1.00 |
| Glycerol | 3.00 |
| Sodium hydroxide | q.s. |
| Preservative | q.s. |
| Perfume | q.s. |
| Water | ad 100.0 | pH adjusted to 6.0

Application Example 192 and Application Example 193

Application example 191 was repeated but using the isoalkane mixture from example 3 or from example 4, respectively, instead of the isoalkane mixture from example 2.

Application Example 194

| Additive | % by wt. |
| --- | --- |
| Acrylate/$C_{10-30}$-alkyl acrylate crosspolymer | 0.40 |
| Polyacrylic acid | 0.20 |
| Xanthan gum | 0.10 |
| Cetearyl alcohol | 3.00 |
| $C_{12-15}$-Alkyl benzoate | 4.00 |
| Caprylic/capric triglyceride | 3.00 |
| Cyclic dimethylpolysiloxane | 5.00 |
| Dimethicone polydimethylsiloxane | 1.00 |
| Hexyl 2-(4'-(diethylamino)-2'-hydroxybenzoyl)-benzoate | 1.20 |
| Isoalkane mixture as in example 2 | 1.00 |
| Ethylhexyltriazone | 2.00 |
| 2,4-Bis(4-(2-ethylhexyloxy)-2-hydroxyl)phenyl)-6-(4 methoxyphenyl)-(1,3,5)-triazine | 1.50 |
| Glycerol | 3.00 |
| Sodium hydroxide | q.s. |
| Preservative | q.s. |
| Perfume | q.s. |
| Water | ad 100.0 | pH adjusted to 6.0

Application Example 195 and Application Example 196

Application example 194 was repeated but using the isoalkane mixture from example 3 or from example 4, respectively, instead of the isoalkane mixture from example 2.

Application Examples 197-199

W/O Cream

Application Example 197

| Additive | % by wt. |
| --- | --- |
| Polyglyceryl 3-diisostearates | 3.50 |
| Glycerol | 3.00 |
| Polyglyceryl-2 dipolyhydroxystearates | 3.50 |
| Isoalkane mixture as in example 2 | 1 |
| Preservative | q.s. |
| Ethylhexyl methoxycinnamate | 5.00 |
| Bis-ethylhexyloxyphenol methoxyphenyltriazine | 0.80 |
| Octocrylene | 3.00 |
| Perfume | q.s. |
| Water | ad 100.0 |
| Magnesium sulfate | 0.6 |
| Isopropyl stearate | 2.0 |
| Caprylyl ether | 8.0 |
| Cetearyl isononanoate | 6.0 |

Application Example 198 and Application Example 199

Application example 197 was repeated but using the isoalkane mixture from example 3 or from example 4, respectively, instead of the isoalkane mixture from example 2.

Application Examples 200-202

W/O/W Cream

Application Example 200

| Additive | % by wt. |
| --- | --- |
| Glyceryl stearate | 3.00 |
| PEG-100 stearate | 0.75 |
| Behenyl alcohol | 2.00 |
| Caprylic/capric triglyceride | 8.0 |
| Octyldodecanol | 5.00 |
| $C_{12-15}$-Alkyl benzoate | 3.00 |
| Isoalkane mixture as in example 2 | 1 |
| Ethylhexylmethoxycinnamate | 5.00 |
| Bis-ethylhexyloxyphenol methoxyphenyltriazine | 1.80 |
| Ethylhexyltriazone | 1.50 |
| Magnesium sulfate ($MgSO_4$) | 0.80 |
| Ethylenediaminetetraacetic acid | 0.10 |
| Preservative | q.s. |
| Perfume | q.s. |
| Water | ad 100.0 | pH adjusted to 6.0

Application Example 201 and Application Example 202

Application example 200 was repeated but using the isoalkane mixture from example 3 or from example 4, respectively, instead of the isoalkane mixture from example 2.

Application Examples 203-220

Conditioner Shampoo with Pearlesence

Application Examples 203-205

| Additive | App. Ex. 203 | App. Ex. 204 | App. Ex. 205 |
| --- | --- | --- | --- |
| Polyquaternium-10 | 0.5 | 0.5 | 0.5 |
| Sodium laureth sulfate | 9.0 | 9.0 | 9.0 |
| Cocoamidopropylbetaine | 2.5 | 2.5 | 2.5 |
| Benzophenone-3 | 1.5 | 0.5 | 1.00 |
| Pearlizing agent | 2.0 | 2.0 | 2.0 |
| Isoalkane mixture as in example 2 | 0.1 | 0.15 | 0.05 |
| Disodium EDTA | 0.1 | 0.2 | 0.15 |
| Preservative, perfume, thickener, pH regulator and solubility promoter | q.s. | q.s. | q.s. |
| Water, DEM. (demineralized) | ad 100.0 | ad 100.0 | ad 100.0 |

The pH is adjusted to 6.
App. Ex. Application example

Application Examples 206-208 and Application Examples 209-211

Application examples 203-205 were repeated but using the isoalkane mixture from example 3 or from example 4, respectively, instead of the isoalkane mixture from example 2.

Application Examples 212-214

| Additive | App. Ex. 212 | App. Ex. 213 | App. Ex. 214 |
|---|---|---|---|
| Polyquaternium-10 | 0.50 | 0.50 | 0.40 |
| Sodium laureth sulfate | 9.00 | 8.50 | 8.90 |
| Cocoamidopropylbetaine | 2.50 | 2.60 | 3.00 |
| Benzophenone-4 | 0.50 | 0.50 | 1.00 |
| Isoalkane mixture from example 2 | 10.50 | 3.00 | 1.00 |
| Pearlizing agent | 2.00 | 2.50 | |
| Disodium EDTA | 0.10 | 0.15 | 0.05 |
| Preservative, perfume, thickener, pH regulator and solubility promoter | q.s. | q.s. | q.s. |
| Water (demineralized) | ad 100 | ad 100 | ad 100 | pH adjusted to 6.0
App. Ex. Application example

Application Examples 215-217 and Application Examples 218-220

Application examples 212-214 were repeated but using the isoalkane mixture from example 3 or from example 4, respectively, instead of the isoalkane mixture from example 2.

Application Examples 221-253

Clear Conditioner Shampoo

Application Examples 221-223

| Additive | App. Ex. 221 | App. Ex. 222 | App. Ex. 223 |
|---|---|---|---|
| Polyquaternium-10 | 0.5 | 0.5 | 0.5 |
| Sodium laureth sulfate | 9.0 | 9.0 | 9.0 |
| Benzophenone 3 | 1.00 | 1.50 | 0.50 |
| Cocoamidopropylbetaine | 2.5 | 2.5 | 2.5 |
| Isoalkane mixture as in example 2 | 0.05 | 0.15 | 0.1 |
| Iminodisuccinic acid, Na salt | 0.2 | 0.3 | 0.8 |
| Preservative, perfume, thickener, pH regulator and solubility promoter | q.s. | q.s. | q.s. |
| Water, DEM (demineralized) | ad 100.0 | ad 100.0 | ad 100.0 |

The pH is adjusted to 6
App. Ex. Application example

Application Examples 224-226 and Application Examples 227-229

Application examples 221-223 were repeated but using the isoalkane mixture from example 3 or from example 4, respectively, instead of the isoalkane mixture from example 2.

Application Examples 230-234

| Additive | App. Ex. 230 | App. Ex. 231 | App. Ex. 232 | App. Ex. 233 | App. Ex. 234 |
|---|---|---|---|---|---|
| Amphotensid GB 2009 | 10.00 | 15.00 | 20.00 | 12.00 | 17.00 |
| Plantacare 2000 | 5.00 | 6.00 | 7.00 | 8.00 | 4.00 |
| Tego Betain L7 | 15.00 | 12.00 | 10.00 | 18.00 | 20.00 |
| Luviquat FC 550 | 0.30 | 0.20 | 0.20 | 0.20 | 0.30 |
| Perfume | 0.10 | 0.10 | 0.10 | 0.10 | 0.10 |
| Isoalkane mixture from example 2 | 2.00 | 4.00 | 7.00 | 1.90 | 6.00 |
| Cremophor PS 20 | 5.00 | 1.00 | 1.00 | 7.00 | 5.00 |
| Preservative | 0.10 | 0.10 | 0.10 | 0.10 | 0.10 |
| Rewopal LA 3 | 2.00 | 1.00 | 0.50 | 2.00 | 2.00 |
| Citric acid | 0.20 | 0.20 | 0.20 | 0.20 | 0.20 |
| Stepan PEG 600 DS | 3.00 | 2.00 | 2.00 | 3.00 | 2.50 |
| Water dem. | ad 100 | ad 100 | ad 100 | ad 100 | ad 100 |

App. Ex. Application example

Application Examples 235-239 and Application Examples 240-244

Application examples 230-234 were repeated but using the isoalkane mixture from example 3 or from example 4, respectively, instead of the isoalkane mixture from example 2.

Application Examples 245-247

| Additive | App. Ex. 245 | App. Ex. 246 | App. Ex. 247 |
|---|---|---|---|
| Polyquaternium-10 | 0.50 | 0.50 | 0.50 |
| Sodium laureth sulfate | 9.00 | 8.50 | 9.50 |
| Isoalkane mixture from example 2 | 4.00 | 3.00 | 9.00 |
| Benzophenone-3 | 1.00 | 1.50 | 0.50 |
| Imidosuccinic acid, Na salt | 0.20 | 0.20 | 0.80 |
| Preservative, perfume, thickener, pH regulator and solubility promoter | q.s. | q.s. | q.s. |
| Water (demineralized) | ad 100 | ad 100 | ad 100 | pH adjusted to 6.0
App. Ex. Application example

Application Examples 248-250 and Application Examples 251-253

Application examples 245-247 were repeated but using the isoalkane mixture from example 3 or from example 4, respectively, instead of the isoalkane mixture from example 2.

Application Examples 254-271

Clear Light Shampoo with Volume Effect

Application Examples 254-256

| Additive | App. Ex. 254 | App. Ex. 255 | App. Ex. 256 |
|---|---|---|---|
| Sodium laureth sulfate | 10.0 | 10.0 | 10.0 |
| Ethylhexyl methoxycinnamate | 2 | 2 | 2 |
| Cocoamidopropylbetaine | 2.5 | 2.5 | 2.5 |
| Isoalkane mixture as in example 2 | 0.05 | 0.1 | 0.01 |
| Disodium EDTA | 0.2 | 0.15 | 0.7 |
| Preservative, perfume, thickener, pH regulator and solubility promoter | q.s. | q.s. | q.s. |
| Water, DEM (demineralized) | ad 100.0 | ad 100.0 | ad 100.0 |

The pH is adjusted to 5.5.

App. Ex. Application example

Application Examples 257-259 and Application Examples 260-262

Application examples 254-256 were repeated but using the isoalkane mixture from example 3 or from example 4, respectively, instead of the isoalkane mixture from example 2.

Application Examples 263-265

| Additive | App. Ex. 263 | App. Ex. 264 | App. Ex. 265 |
|---|---|---|---|
| Sodium laureth sulfate | 10.00 | 10.50 | 11.00 |
| Ethylhexyl methoxycinnamate | 2.00 | 1.50 | 2.30 |
| Isoalkane mixture from example 2 | 9.00 | 7.00 | 1.00 |
| Cocoamidopropylbetaine | 2.50 | 2.60 | 2.20 |
| Disodium EDTA | 0.01 | 0.10 | 0.01 |
| Preservative, perfume, thickener, pH regulator and solubility promoter | q.s. | q.s. | q.s. |
| Water (demineralized) | ad 100 | ad 100 | ad 100 | pH adjusted to 5.5

App. Ex. Application example

Application Examples 266-268 and Application Examples 269-271

Application examples 263-265 were repeated but using the isoalkane mixture from example 3 or from example 4, respectively, instead of the isoalkane mixture from example 2.

Application Examples 272-286

Clear Shampoo

Application Examples 272-276

| Additive | App. Ex. 272 | App. Ex. 273 | App. Ex. 274 | App. Ex. 275 | App. Ex. 276 |
|---|---|---|---|---|---|
| Texapon N 70 | 13.00 | 15.00 | 10.50 | 12.50 | 10.00 |
| Dehyton PK 45 | 7.50 | 7.00 | 5.00 | 5.50 | 10.00 |
| Cetiol HE | 2.00 | 2.50 | 3.50 | 5.00 | 2.30 |
| Perfume | 0.10 | 0.10 | 0.10 | 0.10 | 0.10 |
| Isoalkane mixture from example 2 | 2.00 | 4.00 | 6.00 | 3.50 | 7.00 |
| D-Panthenol USP | 1.00 | 1.50 | 1.80 | 1.70 | 1.40 |
| Preservative | 0.10 | 0.10 | 0.10 | 0.10 | 0.10 |
| Citric acid | 0.10 | 0.10 | 0.10 | 0.10 | 0.10 |
| Luviquat Ultra Care | 1.50 | 1.00 | 1.50 | 1.20 | 1.10 |
| Sodium chloride | 1.50 | 1.40 | 1.40 | 1.30 | 1.50 |
| Water dem. | ad 100 | ad 100 | ad 100 | ad 100 | ad 100 |

App. Ex. Application example

Application Examples 277-281 and Application Examples 282-286

Application examples 254-256 were repeated but using the isoalkane mixture from example 3 or from example 4, respectively, instead of the isoalkane mixture from example 2.

Application Examples 287-301

Shampoo

Application Examples 287-291

| Additive | App. Ex. 287 | App. Ex. 288 | App. Ex. 289 | App. Ex. 290 | App. Ex. 291 |
|---|---|---|---|---|---|
| Texapon NSO | 35.00 | 40.00 | 30.00 | 45.00 | 27.00 |
| Plantacare 2000 | 5.00 | 5.50 | 4.90 | 3.50 | 7.00 |
| Tego Betain L7 | 10.00 | 5.00 | 12.50 | 7.50 | 15.00 |
| Perfume | 0.10 | 0.10 | 0.10 | 0.10 | 0.10 |
| Isoalkane mixture from example 2 | 3.50 | 3.50 | 10.5 | 10.00 | 20.00 |
| D-Panthenol USP | 0.50 | 1.00 | 0.80 | 1.50 | 0.50 |
| Preservative | 0.10 | 0.10 | 0.10 | 0.10 | 0.10 |
| Citric acid | 0.10 | 0.10 | 0.10 | 0.10 | 0.10 |
| Rewopal LA 3 | 0.50 | 2.00 | 0.50 | 0.50 | 2.00 |
| Sodium chloride | 1.50 | 1.50 | 1.50 | 1.50 | 1.50 |
| Water dem. | ad 100 | ad 100 | ad 100 | ad 100 | ad 100 |

App. Ex. Application example

Application Examples 292-296 and Application Examples 297-301

Application examples 287-291 were repeated but using the isoalkane mixture from example 3 or from example 4, respectively, instead of the isoalkane mixture from example 2.

Application Examples 302-304

W/O/W Emulsion

Application Example 302

| Additive | % by wt. |
|---|---|
| Glyceryl stearate | 3.00 |
| PEG-100 stearate | 0.75 |
| Behenyl alcohol | 2.00 |
| Caprylic/capric triglyceride | 8.0 |
| Octyldodecanol | 5.00 |
| $C_{12-15}$-Alkyl benzoate | 3.00 |
| Hexyl 2-(4'-(diethylamino)-2'-hydroxybenzoyl)-benzoate | 1.30 |
| Isoalkane mixture as in example 2 | 1.00 |
| Ethylhexyl methoxycinnamate | 5.00 |
| 2,4-Bis(4-(2-ethylhexyloxy)-2-hydroxyl)phenyl)-6-(4-methoxyphenyl)-(1,3,5)-triazine | 1.80 |
| Ethylhexyltriazone | 1.50 |
| Magnesium sulphate ($MgSO_4$) | 0.80 |
| Ethylenediaminetetraacetic acid | 0.10 |
| Preservative | q.s. |
| Perfume | q.s. |
| Water | ad 100.0 | pH adjusted to 6.0

Application Example 303 and Application Example 304

Application example 302 was repeated but using the isoalkane mixture from example 3 or from example 4, respectively, instead of the isoalkane mixture from example 2.

Application Examples 305-334

Solids-Stabilized Emulsions

Application Examples 305-309

| Additive | App. Ex. 305 | App. Ex. 306 | App. Ex. 307 | App. Ex. 308 | App. Ex. 309 |
|---|---|---|---|---|---|
| Mineral oil | | | | 16.0 | 16.0 |
| Octyldodecanol | 9.0 | 9.0 | 5.0 | | |
| Caprylic/capric triglyceride | 9.0 | 9.0 | 6.0 | | |
| $C_{12-15}$-Alkyl benzoate | | | | 5.0 | 8.0 |
| Butylene glycol dicaprylate/dicaprate | | | | | 8.0 |
| Dicaprylyl ether | 9.0 | | | 4.0 | |
| Dicaprylyl carbonate | | 9.0 | | | |
| Hydroxyoctacosanyl hydroxystearate | 2.0 | 2.0 | 2.0 | 2.0 | 1.5 |
| Disteardimonium hectorite | 1.0 | 0.75 | 0.5 | 0.5 | 0.25 |
| Cera Microcristallina + Paraffinum Liquidum | | | | | 5.0 |
| Hydroxypropylmethylcellulose | | | | | 0.05 |
| Dimethicone | | | | | 3.0 |
| Ethylhexyl methoxycinnamate | | | | | 3.0 |
| 4-Methylbenzylidenecamphor | | | | | 4.0 |
| Diethylhexylbutamidotriazone | | | | | 4.0 |
| Methylenebisbenzotriazolyl tetramethylbutylphenol | | | | | 4.0 |
| Bis-ethylhexyloxyphenol methoxyphenyltriazine | | 0.5 | | 2.00 | 1.00 |
| Drometrizole trisiloxane | | | 0.50 | 1.00 | |
| Terephthalidenedicamphorsulfonic acid | | | 1.00 | 0.50 | 1.50 |
| Phenyldibenzimidazoletetrasulfonic acid | | | | 1.50 | 0.5 |
| Titanium dioxide + alumina + simethicone + aqua | | 2.0 | 4.0 | 2.0 | 4.0 |
| Titanium dioxide + trimethoxycaprylylsilane | | | | | 3.0 |
| Zinc oxide | | | | 6.0 | |
| Silica dimethyl silylate | | | 1.0 | | |
| Boron nitride | 2.0 | | | | |
| Starch/sodium metaphosphate polymer | | | 0.5 | | |
| Tapioca starch | | | | | 1.0 |
| Isoalkane mixture as in example 2 | 0.80 | 0.10 | 0.40 | 0.50 | 1.00 |
| Hexyl 2-(4'-(diethylamino)-2'-hydroxybenzoyl)benzoate | 0.40 | 1.80 | 5.00 | 3.50 | 4.00 |
| Sodium chloride | 1.0 | 1.0 | 1.0 | 1.0 | 1.0 |
| Glycerol | 5.0 | 10.0 | 3.0 | 6.0 | 10.0 |
| Trisodium EDTA | | | 1.0 | 1.0 | |
| Methyl paraben | 0.21 | | | | 0.2 |
| Propyl paraben | 0.07 | | | | |
| Phenoxyethanol | 0.5 | | 0.4 | 0.4 | 0.5 |
| Hexamidine diisethionate | | | | | 0.08 |

-continued

| Additive | App. Ex. 305 | App. Ex. 306 | App. Ex. 307 | App. Ex. 308 | App. Ex. 309 |
|---|---|---|---|---|---|
| Diazolidinylurea | | | 0.28 | 0.28 | |
| Alcohol | | | | 2.5 | |
| Perfume | q.s. | q.s. | q.s. | q.s. | q.s. |
| Water | ad 100 | ad 100 | ad 100 | ad 100 | ad 100 |

App. Ex. Application example

Application Examples 310-314 and Application Examples 315-319

Application examples 305-309 were repeated but using the isoalkane mixture from example 3 or from example 4, respectively, instead of the isoalkane mixture from example 2.

Application Examples 320-324

| Additive | App. Ex. 320 | App. Ex. 321 | App. Ex. 322 | App. Ex. 323 | App. Ex. 324 |
|---|---|---|---|---|---|
| Mineral oil | | | | | 16.0 |
| Octyldodecanol | 6.0 | | 7.5 | 7.5 | 5.0 |
| Caprylic/capric triglyceride | | | | | 6.0 |
| $C_{12\text{-}15}$-Alkyl benzoate | 7.0 | 8.0 | 7.5 | 7.5 | |
| Butylene glycol dicaprylate/dicaprate | 4.0 | 8.0 | | | |
| Dicaprylyl ether | | 8.0 | 7.5 | 7.5 | |
| Dicaprylyl carbonate | 4.0 | | | | |
| Hydroxyoctacosanyl hydroxystearate | 2.0 | 2.0 | 2.0 | 2.0 | 1.5 |
| PVP/Hexadecene copolymer | | | | 1.0 | 0.7 |
| Disteardimonium hectorite | 1.0 | 1.0 | 1.0 | 0.5 | 1.0 |
| Dimethicone | | 2.0 | | | |
| Cyclomethicone | | | | 2.0 | |
| Ethylhexyl methoxycinnamate | 5.0 | | 5.0 | | |
| Butylmethoxydibenzoylmethane | | 2.0 | | | 1.0 |
| 4-Methylbenzylidenecamphor | | 4.0 | | | 2.0 |
| Ethylhexyltriazone | 2.0 | 2.0 | | | 1.0 |
| Methylenebisbenzotriazolyltetramethylbutylphenol | | | 1.00 | | 0.50 |
| Dimethicodiethylbenzalmalonate | | 3.80 | | | |
| Bis-ethylhexyloxyphenol methoxyphenyltriazine | 2.5 | | 1.5 | 3.00 | |
| Titanium dioxide + alumina + simethicone + aqua | 1.5 | 2.0 | 4.0 | 0.5 | 1.5 |
| Titanium dioxide + trimethoxycaprylylsilane | | | 2.0 | | |
| Zinc oxide | | | 2.0 | | |
| Phenyldibenzimidazoletetrasulfonic acid | 1.00 | | | 2.00 | |
| Phenylbenzimidazolesulfonic acid | 2.0 | | | | |
| Diethylhexyl 2,6-naphthalate | | | | | 3.50 |
| Boron nitride | | | | | 0.5 |
| Starch/sodium metaphosphate polymer | 0.5 | | 1.5 | | |
| Corn starch modified | | 1.0 | | | |
| Acrylate copolymer | | | | 0.25 | |
| Talc | | | | 2.0 | |
| Sodium chloride | 1.0 | 1.0 | 1.0 | | |
| Isoalkane mixture as in example 2 | 0.10 | 0.80 | 0.60 | 1.50 | 0.40 |
| Hexyl 2-(4'-(diethylamino)-2'-hydroxybenzoyl)benzoate | 4.80 | 1.00 | 0.50 | 2.50 | 3.50 |
| Magnesium sulfate | | | | | 0.7 |
| Sodium hydroxide solution 45% | 0.5 | 0.5 | | | |
| Glycerol | 5.0 | 7.5 | 5.0 | 10.0 | 3.0 |
| Trisodium EDTA | | 1.0 | 1.0 | | 1.0 |
| Propylene carbonate | 0.33 | 0.33 | 0.33 | | 0.33 |
| Methyl paraben | 0.21 | 0.21 | 0.2 | 0.2 | 0.21 |
| Propyl paraben | 0.07 | 0.07 | | | 0.07 |
| Phenoxyethanol | 0.5 | 0.5 | 0.5 | 0.5 | 0.5 |
| Hexamidine diisethionate | | | 0.08 | 0.08 | |
| Alcohol | | 5.0 | | | |
| Perfume | q.s. | q.s. | q.s. | q.s. | q.s. |
| Water | ad 100 | ad 100 | ad 100 | ad 100 | ad 100 |

App. Ex. Application example

Application Examples 325-329 and Application Examples 330-334

Application examples 320-324 were repeated, but the isoalkane mixture from example 3 or from example 4, respectively, was used instead of the isoalkane mixture from example 2.

Application Examples 335-349

Antiperspirant Roll-On

Application Examples 335-339

|  | Additive | INCI | App. Ex. 335 | App. Ex. 336 | App. Ex. 337 | App. Ex. 338 | App. Ex. 339 |
|---|---|---|---|---|---|---|---|
| Phase A | Natrosol 250 HR | Hydroxyethyl-cellulose | 0.4 | 0.2 | 0.3 | 0.4 | 0.3 |
|  | Water dem. | Water | 30 | 30 | 30 | 30 | 30 |
| Phase B | Cremophor CO 40 | PEG-40 Hydrogenated Castor Oil | 2 | 2.5 | 3 | 3.5 | 3 |
|  | Bisabolol rac | Bisabolol | 0.1 | 0.1 | 0.1 | 0.1 | 0.1 |
|  | Farnesol | Farnesol | 0.3 | 0.2 | 0.3 | 0.1 | 0.3 |
|  | Perfume | Perfume | 0.1 | 0.2 | 0.2 | 0.1 | 0.3 |
|  | Water dem. | Water | ad 100 | ad 100 | ad 100 | ad 100 | ad 100 |
|  | Ethanol 96% | Alcohol | 25 | 30 | 35 | 30 | 32 |
|  | Isoalkane mixture from example 2 |  | 2 | 5 | 7 | 5 | 6 |
| Phase C | 1,2-propylene glycol care | Propylene glycol | 3 | 2 | 2 | 3 | 2.5 |
|  | Luviquat FC 370 | Polyquaternium-16 | 3 | 2.5 | 2 | 3.5 | 4 |
|  | Allantoin | Allantoin | 0.1 | 0.1 | 0.1 | 0.1 | 0.1 |
|  | Locron L | Aluminum Chlorohydrate | 5 | 5.5 | 7.5 | 6 | 5.5 |

App. Ex. Application example

To prepare the antiperspirant roll-on, phase A was left to swell; phase B and phase C were then dissolved separately. The solutions of phases B and C were then stirred into phase A.

Application Examples 340-344 and Application Examples 345-349

Application examples 335-339 were repeated but using the isoalkane mixture from example 3 or from example 4, respectively, instead of the isoalkane mixture from example 2.

Application Examples 350-364

Emulsion

Application Examples 350-354

|  | Additive | INCI | App. Ex. 350 | App. Ex. 351 | App. Ex. 352 | App. Ex. 353 | App. Ex. 354 |
|---|---|---|---|---|---|---|---|
| Phase A | Abil EM 97 | Sodium Laureth Sulfate | 3 | 3.5 | 4 | 3 | 3.5 |
|  | Isoalkane mixture from example 2 | Hydrogenated Polyisobutene | 15 | 10 | 20 | 5 | 17 |
|  | Luvitol EHO | Cetearyl Ethylhexanoate | 1 | 1 | 0.5 | 5 | 3 |
| Phase B | Water dem. | Water | ad 100 | ad 100 | ad 100 | ad 100 | ad 100 |
|  | Ethanol 96% | Alcohol | 5 | 7 | 5 | 7.5 | 6 |
|  | 1,2-Propylene glycol care | Propylene glycol | 15 | 17 | 17 | 20 | 15 |

-continued

| Additive | INCI | App. Ex. 350 | App. Ex. 351 | App. Ex. 352 | App. Ex. 353 | App. Ex. 354 |
|---|---|---|---|---|---|---|
| Locron L | Aluminum Chlorohydrate | 50 | 50 | 50 | 50 | 50 |

App. Ex. Application example

To prepare the antiperspirant emulsion, phases A and B were mixed thoroughly. Phase B was then stirred into phase A and homogenized.

Application Examples 355-359 and Application Examples 360-364

Application examples 350-354 were repeated but using the isoalkane mixture from example 3 or from example 4, respectively, instead of the isoalkane mixture from example 2.

Application Examples 365-379

Deodorant Stick

Application Examples 365-369

| | Additive | INCI | App. Ex. 365 | App. Ex. 366 | App. Ex. 367 | App. Ex. 368 | App. Ex. 369 |
|---|---|---|---|---|---|---|---|
| Phase A | Stearyl alcohol | Stearyl alcohol | 26 | 30 | 28 | 27 | 26 |
| | Isoalkane mixture from example 2 | | 60 | 51 | 58 | 43.5 | 56 |
| | Cremophor CO 40 | PEG-40 Hydrogenated Castor Oil | 5 | 10 | 2.5 | 5 | 5 |

| | Additive | INCI | App. Ex. 365 | App. Ex. 366 | App. Ex. 367 | App. Ex. 368 | App. Ex. 369 |
|---|---|---|---|---|---|---|---|
| Phase B | Isopropyl palmitate | Isopropyl Palmitate | 2.5 | 3 | 1 | 4 | 2.5 |
| | Locron L | Aluminum Chlorohydrate | 5 | 5 | 10 | 20 | 15 |
| | Perfume | Fragrance | 1.45 | 1 | 0.5 | 0.5 | 0.5 |
| | BHT | BHT | 0.05 | | | | |

App. Ex. Application example

To prepare the deodorant stick, the components of phase A were weighed in and melted; with stirring, phase A was left to cool to 50° C.; the components of phase B were then added one after the other and homogenized. The molten mixture was poured into suitable molds.

Application Examples 370-374 and Application Examples 375-379

Application Examples 365-369 were repeated but using the isoalkane mixture from example 3 or from example 4, respectively, instead of the isoalkane mixture from example 2.

Application Examples 380-391

Sunscreen Gel Cream

Application Examples 380-383

| Additive | App. Ex. 380 | App. Ex. 381 | App. Ex. 382 | App. Ex. 383 |
|---|---|---|---|---|
| Acrylate/C10-30 alkyl acrylate crosspolymer | 0.40 | 0.35 | 0.40 | 0.35 |
| Polyacrylic acid | 0.20 | 0.22 | 0.20 | 0.22 |
| Xanthan gum | 0.10 | 0.13 | 0.10 | 0.13 |
| Cetearyl alcohol | 3.00 | 2.50 | 3.00 | 2.50 |
| C12-15 Alkyl benzoate | 4.00 | 4.50 | 4.00 | 4.50 |
| Caprylic/capric triglyceride | 3.00 | 3.50 | 3.00 | 3.50 |
| Uvinul A Plus | 2.00 | 1.50 | 0.75 | 1.00 |
| UVASorb K2A | | 3.00 | | |
| Ethylhexyl methoxycinnamate | 3.00 | | 1.00 | |
| Bis-ethylhexyloxyphenol methoxyphenyl triazine | | 1.50 | | 2.00 |
| Butylmethoxydibenzoylmethane | | | 2.00 | |
| Disodium phenyldibenzimidazole tetrasulfonate | 2.50 | | 0.50 | 2.00 |
| Ethylhexyltriazone | 4.00 | | 3.00 | 4.00 |
| Octocrylene | | 4.00 | | |
| Diethylhexylbutamidotriazone | 1.00 | | | 2.00 |
| Phenylbenzimidazolesulfonic acid | 0.50 | 3.00 | | |
| Methylenebis-benzotriazolyl tetramethylbutylphenol | 2.00 | | 0.50 | 1.50 |
| Ethylhexyl salicylate | | | 3.00 | |
| Drometrizole trisiloxane | | | 0.50 | |
| Terephthalidenedicamphorsulfonic acid | | 1.50 | | 1.00 |
| Diethylhexyl 2,6-naphthalate | | | 7.00 | |
| microfine titanium dioxide | 6.00 | | 3.00 | |
| microfine zinc oxide | | 9.00 | | 5.25 |
| Isoalkane mixture from example 2 | 10.30 | 5.00 | 4.00 | 8.00 |

-continued

| Additive | App. Ex. 380 | App. Ex. 381 | App. Ex. 382 | App. Ex. 383 |
|---|---|---|---|---|
| Cyclic dimethylpolysiloxane | 5.00 | 5.50 | 5.00 | 5.50 |
| Dimethicone polydimethylsiloxane | 1.00 | 0.60 | 1.00 | 0.60 |
| Glycerol | 1.00 | 1.20 | 1.00 | 1.20 |
| Sodium hydroxide | q.s. | q.s. | q.s. | q.s. |
| Preservative | 0.30 | 0.23 | 0.30 | 0.23 |
| Perfume | 0.20 | | 0.20 | |
| Water | ad 100 | ad 100 | ad 100 | ad 100 | pH adjusted to 6.0

App. Ex. Application example

Application Examples 384-387 and Application Examples 388-391

Application examples 380-383 were repeated but using the isoalkane mixture from example 3 or from example 4, respectively, instead of the isoalkane mixture from example 2.

Application Examples 392-412

O/W Sunscreen Formulation

Application Examples 392-398

| Additive | App. Ex. 392 | App. Ex. 393 | App. Ex. 394 | App. Ex. 395 | App. Ex. 396 | App. Ex. 397 | App. Ex. 398 |
|---|---|---|---|---|---|---|---|
| Glycerol monostearate SE | 0.50 | 1.00 | 3.00 | | | 1.50 | |
| Glyceryl stearate citrate | 2.00 | | 1.00 | | 4.00 | | |
| Stearic acid | | 3.00 | | 2.00 | | | |
| PEG-40 stearate | 0.50 | | | | | 2.00 | |
| Cetyl phosphate | | | | | | 1.00 | |
| Cetearyl sulfate | | | | | | | 0.75 |
| Stearyl alcohol | | | 3.00 | | | 2.00 | 0.60 |
| Cetyl alcohol | 2.50 | 1.10 | | 1.50 | 0.60 | | 2.00 |
| Isoalkane mixture from example 2 | 2.00 | 5.00 | 7.00 | 10.00 | 8.00 | 5.50 | 1.00 |
| Uvinul A Plus | 2.00 | 1.50 | 0.75 | 1.00 | 2.10 | 4.50 | 5.00 |
| UVASorb K2A | | | | | | | |
| Ethylhexyl methoxycinnamate | | | | | 5.00 | 6.00 | 8.00 |
| Bis-Ethylhexyloxyphenol methoxyphenyltriazine | | 1.50 | | 2.00 | 2.50 | | 2.50 |
| Butylmethoxydibenzoyl methane | | | 2.00 | | 2.00 | 1.50 | |
| Disodium phenyl dibenzimidazoletetrasulfonate | 2.50 | | 0.50 | 2.00 | | 0.30 | |
| Ethylhexyltriazone | 4.00 | | 3.00 | 4.00 | | 2.00 | |
| Octocrylene | | 4.00 | | | | | 7.50 |
| Diethylhexylbutamidotriazone | 1.00 | | | 2.00 | 1.00 | | 1.00 |
| Phenylbenzimidazole sulfonic acid | 0.50 | | 3.00 | | | | |
| Methylenebisbenzotriazolyl tetramethylbutylphenol | 2.00 | | 0.50 | 1.50 | 2.50 | | |
| Ethylhexyl salicylate | | | 3.00 | | | | 5.00 |
| Drometrizole trisiloxane | | | 0.50 | | | 1.00 | |
| Terephthalidenedicamphor sulfonic acid | | 1.50 | | 1.00 | 1.00 | | 0.50 |
| Diethylhexyl 2,6-naphthalate | 3.50 | | 7.00 | | 3.50 | 4.00 | |
| microfine titanium dioxide | 1.00 | | 3.00 | | 3.50 | | 1.50 |
| microfine zinc oxide | | | | 0.25 | | 2.00 | |
| $C_{12-15}$-Alkyl benzoate | | 0.25 | | | 4.00 | 7.00 | |
| Dicapryl ether | | | 3.50 | | 2.00 | | |
| Butylene glycol dicaprylate/dicaprate | 5.00 | | 6.00 | | | | |
| Cocoglycerides | | | 6.00 | | 2.00 | | |
| Dimethicone | 0.50 | | 1.00 | | 2.00 | | |
| Cyclomethicone | 2.00 | | 0.50 | | 0.50 | | |
| Shea butter | | 2.00 | | | | | |
| PVP Hexadecene copolymer | 0.200 | | | 0.50 | | 1.00 | |
| Glycerol | 3.00 | 7.50 | | 7.50 | 5.00 | | 2.50 |

-continued

| Additive | App. Ex. 392 | App. Ex. 393 | App. Ex. 394 | App. Ex. 395 | App. Ex. 396 | App. Ex. 397 | App. Ex. 398 |
|---|---|---|---|---|---|---|---|
| Xanthan gum | 0.15 | | 0.05 | | | 0.30 | |
| Sodium carbomer | | 0.20 | | 0.15 | 0.25 | | |
| Vitamin E acetate | 0.60 | | 0.23 | | 0.70 | 1.00 | |
| Glycine soya | | | | 0.50 | | 1.50 | 1.00 |
| Ethylhexyloxyglycine | 0.30 | | | | | | |
| DMDM hydantoin | | 0.60 | 0.40 | 0.20 | | | |
| Glyacil-L | | | | 0.18 | 0.20 | | |
| Methylparaben | 0.15 | | 0.25 | | 0.50 | | |
| Phenoxyethanol | 1.00 | 0.40 | | | 0.40 | 0.50 | 0.40 |
| Trisodium EDTA | 0.02 | | 0.05 | | | | |
| Iminosuccinic acid | | | | 0.25 | 1.00 | | |
| Ethanol | 2.00 | 1.50 | | 3.00 | | 1.20 | 5.00 |
| Perfume | 0.10 | 0.25 | 0.30 | | 0.40 | 0.20 | |
| Water | ad 100 | ad 100 | ad 100 | ad 100 | ad 100 | ad 100 | ad 100 |

App. Ex. Application example

Application Examples 399405 and Application Examples 406-412

Application examples 392-398 were repeated but using the isoalkane mixture from example 3 or from example 4, respectively, instead of the isoalkane mixture from example 2.

Application Examples 414-428

Sunscreen Hydrodispersions

Application Examples 414-418

| Additive | App. Ex. 414 | App. Ex. 415 | App. Ex. 416 | App. Ex. 417 | App. Ex. 418 |
|---|---|---|---|---|---|
| Ceteaereth-20 | 1.00 | | | 0.50 | |
| Cetyl alcohol | | | 1.00 | | |
| Sodium carbomer | | 0.20 | | 0.30 | |
| Acrylate/C10-30 alkyl acrylate crosspolymer | 0.50 | | 0.40 | 0.10 | 0.50 |
| Xanthan gum | | 0.30 | 0.15 | | |
| Isoalkane mixture from example 2 | 3.00 | 6.00 | 2.00 | 6.50 | 8.90 |
| Uvinul A Plus | 2.00 | 1.50 | 0.75 | 1.00 | 2.10 |
| UVASorb K2A | | 2.00 | | | |
| Ethylhexyl methoxycinnamate | | | | | 5.00 |
| Bis-ethylhexyloxyphenol methoxyphenyl triazine | | 1.50 | | 2.00 | 2.50 |
| Butylmethoxydibenzoylmethane | | | 2.00 | | 2.00 |
| Disodium phenyldibenzimidazole tetrasulfonate | 2.50 | | 0.50 | 2.00 | |
| Ethylhexyltriazone | 4.00 | | 3.00 | 4.00 | |
| Octocrylene | | 4.00 | | | |
| Diethylhexylbutamidotriazone | 1.00 | | | 2.00 | 1.00 |
| Phenylbenzimidazolesulfonic acid | 0.50 | | 3.00 | | |
| Methylenebisbenzotriazolyl tetramethylbutylphenol | 2.00 | | 0.50 | 1.50 | 2.50 |
| Ethylhexyl salicylate | | | 3.00 | | |
| Drometrizole trisiloxane | | | 0.50 | | |
| Terephthalidenedicamphorsulfonic acid | | 1.50 | | 1.00 | 1.00 |
| Diethylhexyl 2,6-naphthalate | | | 7.00 | | 9.50 |
| microfine titanium dioxide | 1.00 | | 3.00 | | 3.50 |
| microfine zinc oxide | | | | 0.25 | |
| $C_{12-15}$-Alkyl benzoate | | 2.50 | | | |
| Dicapryl ether | | 4.00 | | | |
| Butylene glycol dicaprylate/dicaprate | 4.00 | | 2.00 | 6.00 | |
| Dicapryl carbonate | | 2.00 | 6.00 | | |
| Dimethicone | | | 0.50 | 1.00 | |
| Phenyltrimethicone | 2.00 | | 0.50 | | |
| Shea butter | | 2.00 | | 5.00 | |
| PVP Hexadecene copolymer | 0.50 | | | 0.50 | 1.00 |
| Tricontanyl PVP | 0.50 | | 1.00 | | |
| Ethylhexylglycerol | | | 1.00 | | 0.80 |
| Glycerol | | 3.00 | 7.50 | 7.50 | 8.50 |

| Additive | App. Ex. 414 | App. Ex. 415 | App. Ex. 416 | App. Ex. 417 | App. Ex. 418 |
|---|---|---|---|---|---|
| Glycine soya | | | 1.50 | | 1.00 |
| Vitamin E acetate | 0.50 | | 0.25 | | 1.00 |
| Alpha-glucosylrutin | 0.60 | | | 0.25 | |
| DMDM hydantoin | | 0.60 | 0.45 | 0.25 | |
| Glyacil-S | 0.20 | | | | |
| Methyl paraben | 0.50 | | 0.25 | 0.15 | |
| Phenoxyethanol | 0.50 | 0.40 | | 1.00 | |
| Trisodium EDTA | | 0.01 | 0.05 | | 0.10 |
| Ethanol | 3.00 | 2.00 | 1.50 | | 7.00 |
| Perfume | 0.20 | | 0.05 | 0.40 | |
| Water | ad 100 | ad 100 | ad 100 | ad 100 | ad 100 |

App. Ex. Application example

Application Examples 419-423 and Application Examples 424-428

Application examples 414-418 were repeated but using the isoalkane mixture from example 3 or from example 4, respectively, instead of the isoalkane mixture from example 2.

Application Examples 429-443

W/O Sunscreen Formulations

Application Examples 429-433

| Additive | App. Ex. 429 | App. Ex. 430 | App. Ex. 431 | App. Ex. 432 | App. Ex. 433 |
|---|---|---|---|---|---|
| Cetyldimethicone copolyol | | 2.50 | | 4.00 | |
| Polyglyceryl-2 dipolyhydroxystearate | 5.00 | | | | 4.50 |
| PEG-30 dipolyhydroxystearate | | | 5.00 | | |
| Isoalkane mixture from example 2 | 1.00 | 8.00 | 9.50 | 3.00 | 9.00 |
| Uvinul A Plus | 2.00 | 1.50 | 0.75 | 1.00 | 2.10 |
| UVASorb K2A | | | 1.50 | | |
| Ethylhexyl methoxycinnamate | | | | | 5.00 |
| Bis-ethylhexyloxyphenol methoxyphenyl triazine | | 1.50 | | 2.00 | 2.50 |
| Butylmethoxydibenzoylmethane | | | 2.00 | | 2.00 |
| Disodium phenyldibenzimidazoletetrasulfonate | 2.50 | | 0.50 | 2.00 | |
| Ethylhexyltriazone | 4.00 | | 3.00 | 4.00 | |
| Octocrylene | | 4.00 | | | |
| Diethylhexylbutamidotriazone | 1.00 | | | 2.00 | 1.00 |
| Phenylbenzimidazolesulfonic acid | 0.50 | | 3.00 | | |
| Methylenebisbenzotriazolyl tetramethylbutylphenol | 2.00 | | 0.50 | 1.50 | 2.50 |
| Ethylhexyl salicylate | | | 3.00 | | |
| Drometrizole trisiloxane | | | 0.50 | | |
| Terephthalidenedicamphorsulfonic acid | | 1.50 | | 1.00 | 1.00 |
| Diethylhexyl-2,6-naphthalate | | | 7.00 | | 3.50 |
| microfine titanium dioxide | 1.00 | | 3.00 | | 3.50 |
| microfine zinc oxide | | | | 0.25 | |
| Mineral oil | | 12.00 | 10.00 | | 8.00 |
| C12-15 alkyl benzoate | | | | 9.00 | |
| Dicaprylyl ether | 10.00 | | | | 7.00 |
| Butylene glycol dicaprylate/dicaprate | | | 2.00 | 8.00 | 4.00 |
| Dicaprylyl carbonate | 5.00 | | 6.00 | | |
| Dimethicone | | 4.00 | 1.00 | 5.00 | |
| Cyclomethicone | 2.00 | 25.00 | | | 2.00 |
| Shea butter | | | 3.00 | | |
| Vaseline | | 4.50 | | | |
| PVP Hexadecene copolymer | 0.50 | | | 0.50 | 1.00 |
| Ethylhexylglycerol | | 0.30 | 1.00 | | 0.50 |
| Glycerol | 3.00 | 7.50 | | 7.50 | 8.50 |
| Glycine soya | | 1.00 | 1.50 | | 1.00 |
| MgSO$_4$ | 1.00 | 0.50 | | 0.50 | |
| MgCl$_2$ | | | 1.00 | | 0.70 |
| Vitamin E acetate | 0.50 | | 0.25 | | 1.00 |

-continued

| Additive | App. Ex. 429 | App. Ex. 430 | App. Ex. 431 | App. Ex. 432 | App. Ex. 433 |
|---|---|---|---|---|---|
| Ascorbyl palmitate | 0.50 | | | 2.00 | |
| DMDM Hydantoin | | 0.60 | 0.40 | 0.20 | |
| Methyl paraben | 0.50 | | 0.25 | 0.15 | |
| Phenoxyethanol | 0.50 | 0.40 | | 1.00 | |
| Trisodium EDTA | 0.12 | 0.05 | | 0.30 | |
| Ethanol | 3.00 | | 1.50 | | 5.00 |
| Perfume | 0.20 | | 0.40 | 0.35 | |
| Water | ad 100 | ad 100 | ad 100 | ad 100 | ad 100 |

App. Ex. Application example

Application Examples 434-438 and Application Examples 439-443

Application examples 429-433 were repeated but using the isoalkane mixture from example 3 or from example 4, respectively, instead of the isoalkane mixture from example 2.

Application Examples 444-458

Solids-Stabilized Emulsions

Application Examples 444-448

| Additive | App. Ex. 444 | App. Ex. 445 | App. Ex. 446 | App. Ex. 447 | App. Ex. 448 |
|---|---|---|---|---|---|
| Mineral oil | | | 16.00 | 16.00 | |
| Octyldodecanol | 9.00 | 9.00 | 5.00 | | |
| Caprylic/capric triglyceride | 9.00 | 9.00 | 6.00 | | |
| C12-15 Alkyl benzoate | | | | 5.00 | 8.00 |
| Butylene glycol dicaprylate/dicaprate | | | | | 8.00 |
| Dicaprylyl ether | 9.00 | | | 4.00 | |
| Dicaprylyl carbonate | | 9.00 | | | |
| Hydroxyoctacosanyl hydroxystearate | 2.00 | 2.00 | 2.20 | 2.50 | 1.50 |
| Disteardimonium hectorite | 1.00 | 0.75 | | 0.50 | 0.25 |
| Cera Microcristallina + Paraffinum Liquidum | | 0.35 | | | 5.00 |
| Hydroxypropylmethylcellulose | | | 0.10 | | 0.05 |
| Dimethicone | | | | | 3.00 |
| Isoalkane mixture from example 2 | 3.00 | 5.00 | 5.50 | 8.50 | 2.00 |
| Uvinul A Plus | 2.00 | 1.50 | 0.75 | 1.00 | 2.10 |
| UVASorb K2A | | | | | |
| Ethylhexyl methoxycinnamate | | | | | 5.00 |
| Bis-ethylhexyloxyphenol methoxyphenyl triazine | | 1.50 | | 2.00 | 2.50 |
| Butylmethoxydibenzoylmethane | | | 2.00 | | 2.00 |
| Disodium phenyldibenzimidazoletetrasulfonate | 2.50 | | 0.50 | 2.00 | |
| Ethylhexyltriazone | 4.00 | | 3.00 | 4.00 | |
| Octocrylene | | 4.00 | | | |
| Diethylhexylbutamidotriazone | 1.00 | | | 2.00 | 1.00 |
| Phenylbenzimidazolesulfonic acid | 0.50 | | 3.00 | | |
| Methylenebisbenzotriazolyl tetramethylbutylphenol | 2.00 | | 0.50 | 1.50 | 2.50 |
| Ethylhexyl salicylate | | | 3.00 | | |
| Drometrizole trisiloxane | | | 0.50 | | |
| Terephthalidenedicamphorsulfonic acid | | 1.50 | | 1.00 | 1.00 |
| Diethylhexyl 2,6-naphthalate | | | 7.00 | | 10.00 |
| microfine titanium dioxide | 1.00 | | 3.00 | | 3.50 |
| microfine zinc oxide | | | | 0.25 | |
| Titanium dioxide + alumina + simethicone + aqua | | 3.0 | | 4.0 | |
| Titanium dioxide + trimethoxycaprylylsilane | | 2.00 | 4.00 | 2.00 | 4.00 |
| Silica dimethyl silylate | 2.50 | | | 6.00 | 2.50 |
| Boron nitride | | | 1.00 | | |
| Starch/sodium metaphosphate polymer | 2.00 | | | | |
| Tapioca starch | | 0.50 | | | |
| Sodium chloride | 5.00 | 7.00 | 8.50 | 3.00 | 4.50 |
| Glycerol | | | | 1.00 | |
| Trisodium EDTA | 1.00 | 1.00 | 1.00 | 1.00 | 1.00 |
| Vitamin E acetate | 5.00 | 10.00 | 3.00 | 6.00 | 10.00 |

-continued

| Additive | App. Ex. 444 | App. Ex. 445 | App. Ex. 446 | App. Ex. 447 | App. Ex. 448 |
|---|---|---|---|---|---|
| Ascorbyl palmitate | 1.00 | 1.00 | | 1.00 | |
| Methyl paraben | | 0.60 | | | 0.20 |
| Propyl paraben | | | | | 0.20 |
| Phenoxyethanol | | | 0.20 | | |
| Hexamidine diisethionate | | | 0.40 | 0.50 | 0.40 |
| Diazolidinylurea | | | | | 0.08 |
| Ethanol | | | 0.23 | 0.20 | |
| Perfume | 5.00 | | 3.00 | 4.00 | |
| Water | ad 100 | ad 100 | ad 100 | ad 100 | ad 100 |

App. Ex. Application example

Application Examples 449-453 and Application Examples 454-458

Application examples 444-448 were repeated but using the isoalkane mixture from example 3 or from example 4, respectively, instead of the isoalkane mixture from example 2.

Application Examples 459-470

Sunscreen Sticks

Application examples 459-462

| Additive | App. Ex. 459 | App. Ex. 460 | App. Ex. 461 | App. Ex. 462 |
|---|---|---|---|---|
| Caprylic/capric triglyceride | 12.00 | 10.00 | 6.00 | |
| Octyldodecanol | 7.00 | 14.00 | 8.00 | 3.00 |
| Butylene glycol dicaprylate/dicaprate | | | | 12.00 |
| Pentaerythrityl tetraisostearate | 10.00 | 6.00 | 8.00 | 7.00 |
| Polyglyceryl-3 diisostearate | 2.50 | | | |
| Bis-Diglyceryl polyacyladipate-2 | 9.00 | 8.00 | 10.00 | 8.00 |
| Cetearyl alcohol | 8.00 | 11.00 | 9.00 | 7.00 |
| Myristyl myristate | 3.50 | 3.00 | 4.00 | 3.00 |
| Beeswax | 5.00 | 5.00 | 6.00 | 6.00 |
| Cera Carnauba | 1.50 | 2.00 | 2.00 | 1.50 |
| Cera Alba | 0.50 | 0.50 | 0.50 | 0.40 |
| C16-40 Alkyl stearate | | 1.50 | 1.50 | 1.50 |
| Isoalkane mixture from example 2 | 2.00 | 3.00 | 6.50 | 12.00 |
| Uvinul A Plus | 2.00 | 1.50 | 0.75 | 9.00 |
| UVASorb K2A | | 2.00 | | 4.00 |
| Ethylhexyl methoxycinnamate | | 3.00 | | |
| Bis-Ethylhexyloxyphenole methoxyphenyl triazine | | 1.50 | | 2.00 |
| Butylmethoxydibenzoylmethane | | | 2.00 | |
| Disodium phenyldibenzimidazole tetrasulfonate | 2.50 | | 0.50 | 2.00 |
| Ethylhexyltriazone | 4.00 | | 3.00 | 4.00 |
| Octocrylene | | 4.00 | | |
| Diethylhexylbutamidotriazone | 1.00 | | | 2.00 |
| Phenylbenzimidazolesulfonic acid | 0.50 | | 3.00 | |
| Methylenebis-benzotriazolyl tetramethylbutylphenol | 2.00 | | 0.50 | 1.50 |
| Ethylhexyl salicylate | | | 3.00 | |
| Drometrizole trisiloxane | | | 0.50 | |
| Terephthalidenedicamphorsulfonic acid | | 1.50 | | 1.00 |
| Diethylhexyl 2,6-naphthalate | | | 7.00 | |
| microfine titanium dioxide | 1.00 | | 3.00 | |
| microfine zinc oxide | | | | 0.25 |
| Vitamin E acetate | 0.50 | 1.00 | | |
| Ascorbyl palmitate | 0.05 | | 0.05 | |
| *Buxux Chinensis* | 2.00 | 1.00 | | 1.00 |
| Perfume, BHT | 0.10 | 0.25 | | 0.35 |
| *Ricinus Communis* | ad 100 | ad 100 | ad 100 | ad 100 |

App. Ex. Application example

Application Examples 463-466 and Application Examples 467-470

Application examples 459-462 were repeated but using the isoalkane mixture from example 3 or from example 4, respectively, instead of the isoalkane mixture from example 2.

Application Examples 471-494

PIT Sunscreen Emulsions

Application Examples 471-478

| Additive | App. Ex. 471 | App. Ex. 472 | App. Ex. 473 | App. Ex. 474 | App. Ex. 475 | App. Ex. 476 | App. Ex. 477 | App. Ex. 478 |
|---|---|---|---|---|---|---|---|---|
| Glycerol monostearate SE | 0.50 | 2.00 | 3.00 | 5.00 | | 0.50 | 4.00 | |
| Glyceryl isostearate | | | | | 3.50 | 4.00 | 2.00 | |
| Isoceteth-20 | | 0.50 | | | 2.00 | | | |
| Ceteareth-12 | | 5.00 | | 1.00 | | | 3.50 | 5.00 |
| Ceteareth-20 | | 5.00 | | 1.00 | | | | 3.50 |
| PEG-100 stearate | | | | 2.80 | | 2.30 | 3.30 | |
| Cetyl alcohol | 5.20 | | 1.20 | 1.00 | 1.30 | | 0.50 | 0.30 |
| Cetyl palmitate | 2.50 | 1.20 | | 1.50 | | 0.50 | | 1.50 |
| Cetyl dimethicone copolyol | | | | 0.50 | | 1.00 | | |
| Polyglyceryl-2 | | | | 0.75 | 0.30 | | | |
| Isoalkane mixture from example 2 | 2.00 | 5.00 | 7.90 | 15.00 | 1.00 | 5.50 | 12.5 | 5.00 |
| Uvinul A Plus | 2.00 | 1.50 | 0.75 | 1.00 | 2.10 | 4.50 | | 2.10 |
| UVASorb K2A | | | 3.50 | | | | | 1.20 |
| Ethylhexyl methoxycinnamate | | | | | 5.00 | 6.00 | 8.00 | 5.00 |
| Bis-Ethylhexyloxyphenol methoxyphenyl triazine | | 1.50 | | 2.00 | 2.50 | | 2.50 | 2.50 |
| Butyl methoxydibenzoylmethane | | | 2.00 | | 2.00 | 1.50 | | 2.00 |
| Disodium phenyl dibenzimidazole tetrasulfonate | 2.50 | | 0.50 | 2.00 | | 0.30 | | |
| Ethylhexyl triazone | 4.00 | | 3.00 | 4.00 | | 2.00 | | |
| Octocrylene | | 4.00 | | | | | 7.50 | |
| Diethylhexylbutamido-triazone | 1.00 | | | 2.00 | 1.00 | | 1.00 | 1.00 |
| Phenylbenzimidazolesulfonic acid | 0.50 | | 3.00 | | | | | |
| Methylenebis-benzotriazolyl tetramethylbutylphenol | 2.00 | | 0.50 | 1.50 | 2.50 | | | 2.50 |
| Ethylhexyl salicylate | | | 3.00 | | | | 5.00 | |
| Drometrizole trisiloxane | | | 0.50 | | | 1.00 | | |
| Terephthalidenedicamphor-sulfonic acid | | 1.50 | | 1.00 | 1.00 | | 0.50 | 1.00 |
| Diethylhexyl 2,6-naphthalate | | | 7.00 | | 9.50 | 8.00 | | 8.00 |
| microfine titanium dioxide | 1.00 | | 3.00 | | 3.50 | | 1.50 | 3.50 |
| microfine zinc oxide | | | | 0.25 | | 2.00 | | |
| C12-15 Alkyl benzoate | 3.50 | | | 6.35 | | | | 0.10 |
| Cocoglycerides | | 3.00 | | 3.00 | | | | 1.00 |
| Dicapryl ether | 4.50 | | | | | | | |
| Dicaprylyl carbonate | | 4.30 | | 3.00 | | | | 7.00 |
| Dibutyl adipate | | | | 0.50 | | | | 0.30 |
| Phenyltrimethicone | 2.00 | | | 3.50 | | 2.00 | | |
| Cyclomethicone | | 3.00 | | | | | | |
| Ethyl galactomannan | | 0.50 | | | 2.00 | | | |
| Hydrogenated cocoglycerides | | | | | 3.00 | 4.00 | | |
| Abil Wax 2440 | | | | | | | 1.50 | 2.00 |
| PVP Hexadecene copolymer | | | | 1.00 | 1.20 | | | |
| Glycerol | 4.00 | 6.00 | 5.00 | | 8.00 | 10.00 | | |
| Vitamin E acetate | 0.20 | 0.30 | 0.40 | | 0.30 | | | |
| Shea butter | | 2.00 | | 3.60 | | 2.00 | | |
| Iodopropyl butylcarbamate | 0.12 | | | | 0.20 | | | |
| DMDM Hydantoin | 0.10 | | | | 0.12 | | 0.13 | |
| Methyl paraben | | 0.50 | 0.30 | | 0.35 | | | |
| Phenoxyethanol | 0.50 | 0.40 | | 1.00 | | | | |
| Octoxyglycerol | | 0.30 | | | 1.00 | | 0.35 | |
| Ethanol | 2.00 | | 2.00 | | | 5.00 | | |
| Trisodium EDTA | 0.40 | | 0.15 | | | 0.20 | | |

-continued

| Additive | App. Ex. 471 | App. Ex. 472 | App. Ex. 473 | App. Ex. 474 | App. Ex. 475 | App. Ex. 476 | App. Ex. 477 | App. Ex. 478 |
|---|---|---|---|---|---|---|---|---|
| Perfume | 0.20 | | 0.20 | | 0.24 | 0.16 | 0.10 | 0.10 |
| Water | ad 100 | ad 100 | ad 100 | ad 100 | ad 100 | ad 100 | ad 100 | ad 100 |

App. Ex. Application example

Application examples 479-486 and Application Examples 487-494

Application examples 471-478 were repeated but using the isoalkane mixture from example 3 or from example 4, respectively, instead of the isoalkane mixture from example 2.

Application Examples 495-506

Gel Cream

Application examples 495-498

| Additive | App. Ex. 495 | App. Ex. 496 | App. Ex. 497 | App. Ex. 498 |
|---|---|---|---|---|
| Acrylate/C10-30 alkyl acrylate crosspolymer | 0.40 | 0.35 | 0.40 | 0.35 |
| Polyacrylic acid | 0.20 | 0.22 | 0.20 | 0.22 |
| Luvigel EM | 1.50 | 2.50 | 2.80 | 3.50 |
| Xanthan gum | 0.10 | 0.13 | 0.10 | 0.13 |
| Cetearyl alcohol | 3.00 | 2.50 | 3.00 | 2.50 |
| C12-15 Alkyl benzoate | 4.00 | 4.50 | 4.00 | 4.50 |
| Caprylic/capric triglyceride | 3.00 | 3.50 | 3.00 | 3.50 |
| microfine titanium dioxide | 1.00 | | 1.50 | |
| microfine zinc oxide | | 2.00 | | 0.25 |
| Isoalkane mixture from example 2 | 2.00 | 5.00 | 8.00 | 7.50 |

-continued

| Additive | App. Ex. 495 | App. Ex. 496 | App. Ex. 497 | App. Ex. 498 |
|---|---|---|---|---|
| Dihydroxyacetone | | | 3.00 | 5.00 |
| Cyclic dimethylpolysiloxane | 5.00 | 5.50 | 5.00 | 5.50 |
| Dimethicone polydimethylsiloxane | 1.00 | 0.60 | 1.00 | 0.60 |
| Glycerol | 1.00 | 1.20 | 1.00 | 1.20 |
| Sodium hydroxide | q.s. | q.s. | q.s. | q.s. |
| Preservative | 0.30 | 0.23 | 0.30 | 0.23 |
| Perfume | 0.20 | | 0.20 | |
| Water | ad 100 | ad 100 | ad 100 | ad 100 | pH adjusted to 6.0
App. Ex. Application example

Application Examples 499-502 and Application Examples 503-506

Application examples 495-498 were repeated but using the isoalkane mixture from example 3 or from example 4, respectively, instead of the isoalkane mixture from example 2.

Application Examples 507-527

Cosmetic O/W Formulations

Application Examples 507-513

| Additive | App. Ex. 507 | App. Ex. 508 | App. Ex. 509 | App. Ex. 510 | App. Ex. 511 | App. Ex. 512 | App. Ex. 513 |
|---|---|---|---|---|---|---|---|
| Glycerol monostearate SE | 0.50 | 1.00 | 3.00 | | | 1.50 | |
| Glyceryl stearate citrate | 2.00 | | 1.00 | 2.00 | 4.00 | | |
| Stearic acid | | 3.00 | | 2.00 | | | |
| PEG-40 stearate | 0.50 | | | | | 2.00 | |
| Cetyl phosphate | | | | | | 1.00 | |
| Cetearyl sulfate | | | | | | | 0.75 |
| Stearyl alcohol | | | 3.00 | | | 2.00 | 0.60 |
| Cetyl alcohol | 2.50 | 1.10 | | 1.50 | 0.60 | | 2.00 |
| Isoalkane mixture from example 2 | 2.00 | 5.00 | 7.00 | 10.0 | 8.0 | 5.00 | 1.00 |
| Dihydroxyacetone | | | 3.00 | 5.00 | | 4 | 1.50 |
| microfine titanium dioxide | 1.00 | | | | 1.50 | | 1.50 |
| microfine zinc oxide | | | | 0.25 | | 2.00 | |
| C12-15 Alkyl benzoate | | 0.25 | | | 4.00 | 7.00 | |
| Dicapryl ether | | | 3.50 | | 2.00 | | |
| Butylene glycol dicaprylate/dicaprate | 5.00 | | 6.00 | | | | |
| Cocoglycerides | | | | 6.00 | | 2.00 | |
| Dimethicone | 0.50 | | 1.00 | | 2.00 | | |
| Cyclomethicone | 2.00 | | 0.50 | | 0.50 | | |
| Shea butter | | 2.00 | | | | | |
| PVP Hexadecene copolymer | 0.20 | | | 0.50 | | 1.00 | |
| Glycerol | 3.00 | 7.50 | | 7.50 | 5.00 | | 2.50 |
| Xanthan gum | 0.15 | | 0.05 | | | 0.30 | |
| Sodium carbomer | | 0.20 | | 0.15 | 0.25 | | |
| Vitamin E acetate | 0.60 | | 0.23 | | 0.70 | 1.00 | |
| Fucogel 1000 | | 3.00 | 10.00 | | | | |
| Glycine soya | | | | | 0.50 | 1.50 | 1.00 |

-continued

| Additive | App. Ex. 507 | App. Ex. 508 | App. Ex. 509 | App. Ex. 510 | App. Ex. 511 | App. Ex. 512 | App. Ex. 513 |
|---|---|---|---|---|---|---|---|
| Ethylhexyloxyglycine | 0.30 | | | | | | |
| DMDM Hydantoin | | 0.60 | 0.40 | 0.20 | | | |
| Glyacil-L | | | | 0.18 | 0.20 | | |
| Methyl paraben | 0.15 | | 0.25 | | 0.50 | | |
| Phenoxyethanol | 1.00 | 0.40 | | | 0.40 | 0.50 | 0.40 |
| Trisodium EDTA | 0.02 | | 0.05 | | | | |
| Iminosuccinic acid | | | | 0.25 | 1.00 | | |
| Ethanol | 2.00 | 1.50 | | 3.00 | | 1.20 | 5.00 |
| Perfume | 0.10 | 0.25 | 0.30 | | 0.40 | 0.20 | |
| Water | ad 100 | ad 100 | ad 100 | ad 100 | ad 100 | ad 100 | ad 100 |

App. Ex. Application example

Application Examples 514-520 and Application Examples 521-527

Application examples 507-513 were repeated but using the isoalkane mixture from example 3 or from example 4, respectively, instead of the isoalkane mixture from example 2.

Application Examples 528-542

Cosmetic Hydrodispersion Formulations

Application Examples 528-532

| Additive | App. Ex. 528 | App. Ex. 529 | App. Ex. 530 | App. Ex. 531 | App. Ex. 532 |
|---|---|---|---|---|---|
| Ceteareth-20 | 1.00 | | | 0.50 | |
| Cetyl alcohol | | | 1.00 | | |
| Luvigel EM | | 2.00 | | 2.50 | 2.00 |
| Acrylate/C10-30 alkyl acrylate crosspolymer | 0.50 | | 0.40 | 0.10 | 0.50 |
| Xanthan gum | | 0.30 | 0.15 | | |
| Isoalkane mixture from example 2 | 3.00 | 6.00 | 2.00 | 4.00 | 7.00 |
| Dihydroxyacetone | | | 3.00 | 5.00 | |
| Uvinul A Plus | 2.00 | 1.50 | 0.75 | 1.00 | 2.10 |
| microfine titanium dioxide | 1.00 | | 1.00 | | 1.00 |
| microfine zinc oxide | | 1.90 | | 0.25 | |
| C12-15 Alkyl benzoate | 2.00 | 2.50 | | | |
| Dicapryl ether | | 4.00 | | | |
| Butylene glycol dicaprylate/dicaprate | 4.00 | | 2.00 | 6.00 | |
| Dicapryl carbonate | | 2.00 | 6.00 | | |
| Dimethicone | | 0.50 | 1.00 | | |
| Phenyltrimethicone | 2.00 | | 0.50 | | |
| Shea butter | | 2.00 | | 5.00 | |
| PVP Hexadecene copolymer | 0.50 | | | 0.50 | 1.00 |
| Tricontanyl PVP | 0.50 | | 1.00 | | |
| Ethylhexylglycerol | | | 1.00 | | 0.80 |
| Glycerol | 3.00 | 7.50 | | 7.50 | 8.50 |
| Glycine soya | | | 1.50 | | 1.00 |
| Vitamin E acetate | 0.50 | | 0.25 | | 1.00 |
| Alpha-glucosilrutin | 0.60 | | | 0.25 | |
| DMDM Hydantoin | | 0.60 | 0.45 | 0.25 | |
| Glyacil-S | 0.20 | | | | |
| Methyl paraben | 0.50 | | 0.25 | 0.15 | |
| Phenoxyethanol | 0.50 | 0.40 | | 1.00 | |
| Trisodium EDTA | | 0.01 | 0.05 | | 0.10 |
| Ethanol | | 3.00 | 2.00 | 1.50 | 7.00 |
| Perfume | 0.20 | | 0.05 | 0.40 | |
| Water | ad 100 | ad 100 | ad 100 | ad 100 | ad 100 |

App. Ex. Application example

Application Examples 533-537 and Application Examples 538-542

Application examples 528-532 were repeated but using the isoalkane mixture from example 3 or from example 4, respectively, instead of the isoalkane mixture from example 2.

Application Examples 543-557

Cosmetic W/O Formulations

Application Examples 543-547

| Additive | App. Ex. 543 | App. Ex. 544 | App. Ex. 545 | App. Ex. 546 | App. Ex. 547 |
|---|---|---|---|---|---|
| Cetyldimethicone copolyol | | 2.50 | | 4.00 | |
| Polyglyceryl-2 dipolyhydroxystearate | 5.00 | | | | 4.50 |
| PEG-30 dipolyhydroxystearate | | | 5.00 | | |
| Isoalkane mixture from example 2 | 2.00 | 3.00 | 5.00 | 8.50 | 9.00 |
| Uvinul A Plus | 2.00 | 1.50 | 0.75 | 1.00 | 2.10 |
| microfine titanium dioxide | 1.00 | | 3.00 | | 3.50 |
| microfine zinc oxide | | 0.90 | | 0.25 | |
| Mineral oil | | 12.00 | 10.00 | | 8.00 |
| C12-15 Alkyl benzoate | | | | 9.00 | |
| Dicaprylyl ether | 10.00 | | | | 7.00 |
| Butylene glycol dicaprylate/dicaprate | | | 2.00 | 8.00 | 4.00 |
| Dicaprylyl carbonate | 5.00 | | 6.00 | | |
| Dimethicone | | 4.00 | 1.00 | 5.00 | |
| Cyclomethicone | 2.00 | 25.00 | | | 2.00 |
| Shea butter | | | 3.00 | | |
| Vaseline | | 4.50 | | | |
| PVP Hexadecene copolymer | 0.50 | | | 0.50 | 1.00 |
| Ethylhexylglycerol | | 0.30 | 1.00 | | 0.50 |
| Glycerol | 3.00 | 7.50 | | 7.50 | 8.50 |
| Glycine soya | | 1.00 | 1.50 | | 1.00 |
| MgSO$_4$ | 1.00 | 0.50 | | 0.50 | |
| MgCl$_2$ | | | 1.00 | | 0.70 |
| Vitamin E acetate | 0.50 | | 0.25 | | 1.00 |
| Ascorbyl palmitate | 0.50 | | | 2.00 | |
| DMDM Hydantoin | | 0.60 | 0.40 | 0.20 | |
| Methyl paraben | 0.50 | | 0.25 | 0.15 | |
| Phenoxyethanol | 0.50 | 0.40 | | 1.00 | |
| Trisodium EDTA | 0.12 | 0.05 | | 0.30 | |
| Ethanol | 3.00 | | 1.50 | | 5.00 |
| Perfume | 0.20 | | 0.40 | 0.35 | |
| Water | ad 100 | ad 100 | ad 100 | ad 100 | ad 100 |

App. Ex. Application example

Application Examples 548-552 and Application Examples 553-557

Application examples 543-547 were repeated but using the isoalkane mixture from example 3 or from example 4, respectively, instead of the isoalkane mixture from example 2.

Application Examples 558-572

Solids-Stabilized Formulations

Application Examples 558-562

| Additive | App. Ex. 558 | App. Ex. 559 | App. Ex. 560 | App. Ex. 561 | App. Ex. 562 |
|---|---|---|---|---|---|
| Mineral oil | | | | 16.00 | 16.00 |
| Octyldodecanol | 9.00 | 9.00 | 5.00 | | |
| Caprylic/capric triglyceride | 9.00 | 9.00 | 6.00 | | |
| C12-15 Alkyl benzoate | | | | 5.00 | 8.00 |
| Butylene glycol dicaprylate/dicaprate | | | | | 8.00 |

| Additive | App. Ex. 558 | App. Ex. 559 | App. Ex. 560 | App. Ex. 561 | App. Ex. 562 |
|---|---|---|---|---|---|
| Dicaprylyl ether | 9.00 | | | 4.00 | |
| Dicaprylyl carbonate | | 9.00 | | | |
| Hydroxyoctacosanyl hydroxystearate | 2.00 | 2.00 | 2.20 | 2.50 | 1.50 |
| Disteardimonium hectorite | 1.00 | 0.75 | | 0.50 | 0.25 |
| Cera Microcristallina + Paraffinum Liquidum | | 0.35 | | | 5.00 |
| Hydroxypropylmethylcellulose | | | 0.10 | | 0.05 |
| Dimethicone | | | | | 3.00 |
| Isoalkane mixture from example 2 | 3.00 | 5.00 | 5.00 | 6.50 | 2.00 |
| Titanium dioxide + alumina + simethicone + aqua | | 3.00 | | | |
| Titanium dioxide + trimethoxycaprylylsilane | | 2.00 | 4.00 | 2.00 | 4.00 |
| Silica dimethyl silylate | 2.50 | | | 6.00 | 2.50 |
| Boron nitride | | | 1.00 | | |
| Starch/sodium metaphosphate polymer | 2.00 | | | | |
| Tapioca starch | | 0.50 | | | |
| Sodium chloride | 5.00 | 7.00 | 8.50 | 3.00 | 4.50 |
| Glycerol | | | | 1.00 | |
| Trisodium EDTA | 1.00 | 1.00 | 1.00 | 1.00 | 1.00 |
| Vitamin E acetate | 5.00 | 10.00 | 3.00 | 6.00 | 10.00 |
| Ascorbyl palmitate | 1.00 | 1.00 | | 1.00 | |
| Methyl paraben | | 0.60 | | | 0.20 |
| Propyl paraben | | | | | 0.20 |
| Phenoxyethanol | | | 0.20 | | |
| Hexamidine diisethionate | | | 0.40 | 0.50 | 0.40 |
| Diazolidinylurea | | | | | 0.08 |
| Ethanol | | | 0.23 | 0.20 | |
| Perfume | 5.00 | | 3.00 | 4.00 | |
| Water | 0.20 | | 0.30 | 0.10 | |

App. Ex. Application example

Application Examples 563-567 and Application Examples 568-572

Application examples 558-562 were repeated but using the isoalkane mixture from example 3 or from example 4, respectively, instead of the isoalkane mixture from example 2.

Application Examples 574-585

Cosmetic Stick Formulations

Application Examples 574-577

| Additive | App. Ex. 574 | App. Ex. 575 | App. Ex. 576 | App. Ex. 577 |
|---|---|---|---|---|
| Caprylic/capric triglyceride | 12.00 | 10.00 | 6.00 | |
| Octyldodecanol | 7.00 | 14.00 | 8.00 | 3.00 |
| Butylene glycol dicaprylate/dicaprate | | | | 12.00 |
| Pentaerythrityl tetraisostearate | 10.00 | 6.00 | 8.00 | 7.00 |
| Polyglyceryl-3 diisostearate | 2.50 | | | |
| Bis-diglyceryl polyacyl adipate-2 | 9.00 | 8.00 | 10.00 | 8.00 |
| Cetearyl alcohol | 8.00 | 11.00 | 9.00 | 7.00 |
| Myristyl myristate | 3.50 | 3.00 | 4.00 | 3.00 |
| Beeswax | 5.00 | 5.00 | 6.00 | 6.00 |
| Cera Carnauba | 1.50 | 2.00 | 2.00 | 1.50 |
| Cera Alba | 0.50 | 0.50 | 0.50 | 0.40 |
| C16-40 Alkyl stearate | | 1.50 | 1.50 | 1.50 |
| Isoalkane mixture from example 2 | 2.00 | 3.00 | 3.00 | 12.00 |
| microfine titanium dioxide | 1.00 | | 3.00 | |
| microfine zinc oxide | | 1.00 | | 0.25 |
| Vitamin E acetate | 0.50 | 1.00 | | |
| Ascorbyl palmitate | 0.05 | | 0.05 | |
| Buxux Chinensis | 2.00 | 1.00 | | 1.00 |
| Perfume, BHT | 0.10 | 0.25 | | 0.35 |
| Ricinus Communis | ad 100 | ad 100 | ad 100 | ad 100 |

App. Ex. Application example

Application examples 578-581 and application examples 582-585: Application examples 574-577 were repeated but using the isoalkane mixture from example 3 or from example 4, respectively, instead of the isoalkane mixture from example 2.

Application Examples 586-609

Cosmetic PIT Formulations

Application Examples 586-593

| Additive | App. Ex. 586 | App. Ex. 587 | App. Ex. 588 | App. Ex. 589 | App. Ex. 590 | App. Ex. 591 | App. Ex. 592 | App. Ex. 593 |
|---|---|---|---|---|---|---|---|---|
| Glycerol monostearate SE | 0.50 | 2.00 | 3.00 | 5.00 | | 0.50 | 4.00 | |
| Glyceryl isostearate | | | | | 3.50 | 4.00 | 2.00 | |
| Isoceteth-20 | | 0.50 | | | 2.00 | | | |
| Ceteareth-12 | | 5.00 | | 1.00 | | | 3.50 | 5.00 |
| Ceteareth-20 | | 5.00 | | 1.00 | | | | 3.50 |
| PEG-100 stearate | | | | 2.80 | | 2.30 | 3.30 | |
| Cetyl alcohol | 5.20 | | 1.20 | 1.00 | 1.30 | | 0.50 | 0.30 |
| Cetyl palmitate | 2.50 | 1.20 | | 1.50 | | 0.50 | | 1.50 |
| Cetyl dimethicone copolyol | | | | 0.50 | | 1.00 | | |
| Polyglyceryl-2 | | | | 0.75 | 0.30 | | | |
| Isoalkane mixture from example 2 | 2.00 | 5.00 | 7.90 | 15.00 | 1.00 | 6.50 | 5.50 | 9.50 |
| Dihydroxyacetone | | | 3.00 | 5.00 | | | 4.00 | |
| Uvinul A Plus | 2.00 | 1.50 | 0.75 | 1.00 | 2.10 | 4.50 | 5.00 | 2.10 |
| microfine titanium dioxide | 1.00 | | 1.50 | | 3.50 | | 1.50 | 1.00 |
| microfine zinc oxide | | 1.00 | | 0.25 | | 2.00 | | 1.50 |
| C12-15 Alkyl benzoate | 3.50 | | | 6.35 | | | | 0.10 |
| Cocoglycerides | | 3.00 | | 3.00 | | | | 1.00 |
| Dicapryl ether | 4.50 | | | | | | | |
| Dicaprylyl carbonate | | 4.30 | | 3.00 | | | | 7.00 |
| Dibutyl adipate | | | | 0.50 | | | | 0.30 |
| Phenyltrimethicones | 2.00 | | | 3.50 | | 2.00 | | |
| Cyclomethicone | | 3.00 | | | | | | |
| Ethylgalactomannan | | 0.50 | | | 2.00 | | | |
| Hydrogenated cocoglycerides | | | | | 3.00 | 4.00 | | |
| Abil Wax 2440 | | | | | | | 1.50 | 2.00 |
| PVP Hexadecene copolymer | | | | 1.00 | 1.20 | | | |
| Glycerol | 4.00 | 6.00 | 5.00 | | 8.00 | 10.00 | | |
| Vitamin E acetate | 0.20 | 0.30 | 0.40 | | 0.30 | | | |
| Shea butter | | 2.00 | | 3.60 | | 2.00 | | |
| Iodopropyl butylcarbamate | 0.12 | | | | 0.20 | | | |
| DMDM Hydantoin | 0.10 | | | | 0.12 | | 0.13 | |
| Methyl paraben | | 0.50 | 0.30 | | 0.35 | | | |
| Phenoxyethanol | 0.50 | 0.40 | | 1.00 | | | | |
| Octoxyglycerol | | 0.30 | | | 1.00 | | 0.35 | |
| Ethanol | 2.00 | | 2.00 | | | 5.00 | | |
| Trisodium EDTA | 0.40 | | 0.15 | | | 0.20 | | |
| Perfume | 0.20 | | 0.20 | | 0.24 | 0.16 | 0.10 | 0.10 |
| Water | ad 100 | ad 100 | ad 100 | ad 100 | ad 100 | ad 100 | ad 100 | ad 100 |

App. Ex. Application example

Application Examples 594-601 and Application Examples 602-609

Application examples 586-593 were repeated but using the isoalkane mixture from example 3 or from example 4, respectively, instead of the isoalkane mixture from example 2.

Application Examples 610-621

Cosmetic Oils and Oil Gels

Application Examples 610-613

| Additive | App. Ex. 610 | App. Ex. 611 | App. Ex. 612 | App. Ex. 613 |
|---|---|---|---|---|
| Caprylic/capric triglyceride | 12.00 | 10.00 | 6.00 | |
| Octyldodecanol | 7.00 | 14.00 | 8.00 | 3.00 |
| Butylene glycol dicaprylate/dicaprate | | | | 12.00 |
| Pentaerythrityl tetraisostearate | 10.00 | 6.00 | 8.00 | 7.00 |
| Polyglyceryl-3 diisostearate | 2.50 | | | |
| Bis-diglyceryl polyacyladipate-2 | 9.00 | 8.00 | 10.00 | 8.00 |
| Myristyl myristate | 3.50 | 3.00 | 4.00 | 3.00 |
| Bentone-34 | 5.00 | 5.00 | 6.00 | 6.00 |

-continued

| Additive | App. Ex. 610 | App. Ex. 611 | App. Ex. 612 | App. Ex. 613 |
|---|---|---|---|---|
| Propylene carbonate | 15.00 | 20.00 | 18.00 | 19.50 |
| Isoalkane mixture from example 2 | 2.00 | 3.00 | 9.50 | 12.00 |
| Vitamin E acetate | 0.50 | 1.00 | | |
| Ascorbyl palmitate | 0.05 | | 0.05 | |
| *Buxux Chinensis* | 2.00 | 1.00 | | 1.00 |
| Perfume, BHT | 0.10 | 0.25 | | 0.35 |
| *Ricinus Communis* | ad 100 | ad 100 | ad 100 | ad 100 |

App. Ex. Application example

Application Examples 614-617 and Application Examples 618-621

Application examples 610-613 were repeated but using the isoalkane mixture from example 3 or from example 4, respectively, instead of the isoalkane mixture from example 2.

Application Examples 622-636

Cosmetic Aftersun Formulations

Application examples 622-626

| Additive | App. Ex. 622 | App. Ex. 623 | App. Ex. 624 | App. Ex. 625 | App. Ex. 626 |
|---|---|---|---|---|---|
| Ceteaereth-20 | 1.00 | | | 0.50 | |
| Cetyl alcohol | | | 1.00 | | |
| Luvigel EM | | 2.00 | | 2.50 | 2.00 |
| Acrylate/C10-30 alkyl acrylate crosspolymer | 0.50 | 0.30 | 0.40 | 0.10 | 0.50 |
| Xanthan gum | | 0.30 | 0.15 | | |
| Isoalkane mixture from example 2 | 3.00 | 6.00 | 2.00 | 6.50 | 8.50 |
| C12-15 Alkyl benzoate | 2.00 | 2.50 | | | |
| Dicapryl ether | | 4.00 | | | |
| Butylene glycol dicaprylate/dicaprate | 4.00 | | 2.00 | 6.00 | |
| Dicapryl carbonate | | 2.00 | 6.00 | | |
| Dimethicone | | | 0.50 | 1.00 | |
| Phenyltrimethicone | 2.00 | | 0.50 | | |
| Tricontanyl PVP | 0.50 | | 1.00 | | |
| Ethylhexylglycerol | | | 1.00 | | 0.80 |
| Glycerol | 3.00 | 7.50 | | 7.50 | 8.50 |
| Glycine soya | | | 1.50 | | 1.00 |
| Vitamin E acetate | 0.50 | | 0.25 | | 1.00 |
| Alpha-glucosilrutin | 0.60 | | | 0.25 | |
| Trisodium EDTA | | 0.01 | 0.05 | | 0.10 |
| Ethanol | 15.00 | 10.00 | 8.00 | 12.00 | 9.00 |
| Perfume | 0.20 | | 0.05 | 0.40 | |
| Water | ad 100 | ad 100 | ad 100 | ad 100 | ad 100 |

App. Ex. Application example

Application Examples 627-631 and Application Examples 632-636

Application examples 622-626 were repeated but using the isoalkane mixture from example 3 or from example 4, respectively, instead of the isoalkane mixture from example 2.

Application Examples 637-657

Cosmetic Formulations for Decorative Cosmetics

Application Examples 637-643

| Additive | App. Ex. 637 | App. Ex. 638 | App. Ex. 639 | App. Ex. 640 | App. Ex. 641 | App. Ex. 642 | App. Ex. 643 |
|---|---|---|---|---|---|---|---|
| Glycerol monostearate SE | 0.50 | 1.00 | 3.00 | | | 1.50 | |
| Glyceryl stearate citrate | 2.00 | | 1.00 | 2.00 | 4.00 | | |
| Stearic acid | | 3.00 | | 2.00 | | | |
| PEG-40 stearate | 0.50 | | | | | 2.00 | |
| Cetyl phosphate | | | | | | 1.00 | |
| Cetearyl sulfate | | | | | | | 0.75 |
| Stearyl alcohol | | | 3.00 | | | 2.00 | 0.60 |
| Cetyl alcohol | 2.50 | 1.10 | | 1.50 | 0.60 | | 2.00 |
| Isoalkane mixture from example 2 | 2.00 | 5.00 | 7.00 | 5.50 | 7.50 | 10.00 | 1.00 |
| Titanium dioxide | 10.00 | 12.00 | 9.00 | 8.50 | 11.00 | 9.50 | 10.00 |
| Iron oxides | 2.00 | 4.00 | 3.00 | 5.00 | 3.40 | 6.00 | 4.40 |
| Zinc oxide | | 4.00 | | 2.00 | | 3.00 | |
| C12-15 alkyl benzoate | | 0.25 | | | 4.00 | 7.00 | |
| Dicapryl ether | | | 3.50 | | 2.00 | | |
| Butylene glycol dicaprylate/dicaprate | 5.00 | | 6.00 | | | | |
| Cocoglycerides | | | 6.00 | | 2.00 | | |
| Dimethicone | 0.50 | | 1.00 | | 2.00 | | |
| Cyclomethicone | 2.00 | | 0.50 | | 0.50 | | |
| Shea butter | | 2.00 | | | | | |
| PVP Hexadecene copolymer | 0.20 | | | 0.50 | | 1.00 | |
| Glycerol | 3.00 | 7.50 | | 7.50 | 5.00 | | 2.50 |
| Xanthan gum | 0.15 | | 0.05 | | | 0.30 | |
| Sodium carbomer | | 0.20 | | 0.15 | 0.25 | | |
| Vitamin E acetate | 0.60 | | 0.23 | | 0.70 | 1.00 | |
| Glycine soya | | | | 0.50 | | 1.50 | 1.00 |
| Ethylhexyloxyglycine | 0.30 | | | | | | |
| DMDM Hydantoin | | 0.60 | 0.40 | 0.20 | | | |
| Glyacil-L | | | | 0.18 | 0.20 | | |
| Methyl paraben | 0.15 | | 0.25 | | 0.50 | | |
| Phenoxyethanol | 1.00 | 0.40 | | | 0.40 | 0.50 | 0.40 |
| Trisodium EDTA | 0.02 | | 0.05 | | | | |
| Iminosuccinic acid | | | | 0.25 | 1.00 | | |
| Ethanol | 2.00 | 1.50 | | 3.00 | | 1.20 | 5.00 |
| Perfume | 0.10 | 0.25 | 0.30 | | 0.40 | 0.20 | |
| Water | ad 100 | ad 100 | ad 100 | ad 100 | ad 100 | ad 100 | ad 100 |

App. Ex. Application example

Application Examples 644-650 and Application Examples 651-657

Application examples 637-643 were repeated but using the isoalkane mixture from example 3 or from example 4, respectively, instead of the isoalkane mixture from example 2.

Application Examples 658-713

Cleaning Formulations for Showering/Bathing/Washing

Application Examples 658-662

| Additive | App. Ex. 658 | App. Ex. 659 | App. Ex. 660 | App. Ex. 661 | App. Ex. 662 |
|---|---|---|---|---|---|
| Texapon N 70 | 13.00 | 15.00 | 10.50 | 12.50 | 10.00 |
| Dehyton PK 45 | 7.50 | 7.00 | 5.00 | 5.50 | 10.00 |
| Cetiol HE | 2.00 | 2.50 | 3.50 | 5.00 | 2.30 |
| Perfume | 0.10 | 0.10 | 0.10 | 0.10 | 0.10 |
| Isoalkane mixture from example 2 | 1.00 | 4.50 | 7.00 | 1.40 | 3.00 |
| D-Panthenol USP | 1.00 | 1.50 | 1.80 | 1.70 | 1.40 |
| Preservative | 0.10 | 0.10 | 0.10 | 0.10 | 0.10 |
| Citric acid | 0.10 | 0.10 | 0.10 | 0.10 | 0.10 |
| Luviquat Ultra Care | 1.50 | 1.00 | 1.50 | 1.20 | 1.10 |
| Sodium chloride | 1.50 | 1.40 | 1.40 | 1.30 | 1.50 |
| Water dem. | ad 100 | ad 100 | ad 100 | ad 100 | ad 100 |

App. Ex. Application example

Application Examples 663-667 and Application Examples 668-672

Application examples 658-662 were repeated but using the isoalkane mixture from example 3 or from example 4, respectively, instead of the isoalkane mixture from example 2.

Application Examples 673-677

| Additive | App. Ex. 673 | App. Ex. 674 | App. Ex. 675 | App. Ex. 676 | App. Ex. 677 |
|---|---|---|---|---|---|
| Amphotensid GB 2009 | 10.00 | 15.00 | 20.00 | 12.00 | 17.00 |
| Plantacare 2000 | 5.00 | 6.00 | 7.00 | 8.00 | 4.00 |
| Tego Betain L7 | 15.00 | 12.00 | 10.00 | 18.00 | 20.00 |
| Luviquat FC 550 | 0.30 | 0.20 | 0.20 | 0.20 | 0.30 |
| Perfume | 0.10 | 0.10 | 0.10 | 0.10 | 0.10 |
| Isoalkane mixture from example 2 | 3.00 | 6.00 | 5.50 | 4.00 | 1.50 |

-continued

| Additive | App. Ex. 673 | App. Ex. 674 | App. Ex. 675 | App. Ex. 676 | App. Ex. 677 |
|---|---|---|---|---|---|
| Cremophor PS 20 | 5.00 | 1.00 | 1.00 | 7.00 | 5.00 |
| Preservative | 0.10 | 0.10 | 0.10 | 0.10 | 0.10 |
| Rewopal LA 3 | 2.00 | 1.00 | 0.50 | 2.00 | 2.00 |
| Citric acid | 0.20 | 0.20 | 0.20 | 0.20 | 0.20 |
| Stepan PEG 600 DS | 3.00 | 2.00 | 2.00 | 3.00 | 2.50 |
| Water dem. | ad 100 | ad 100 | ad 100 | ad 100 | ad 100 |

App. Ex. Application example

Application Examples 678-682 and Application Examples 683-687

Application examples 673-677 were repeated but using the isoalkane mixture from example 3 or from example 4, respectively, instead of the isoalkane mixture from example 2.

Application Examples 693-699

| Additive | App. Ex. 693 | App. Ex. 694 | App. Ex. 695 | App. Ex. 696 | App. Ex. 697 | App. Ex. 698 | App. Ex. 699 |
|---|---|---|---|---|---|---|---|
| Texapon NSO | 35.00 | 40.00 | 30.00 | 45.00 | 27.00 | | |
| Plantacare 2000 | 5.00 | 5.50 | 4.90 | 3.50 | 7.00 | | |
| Tego Betain L7 | 10.00 | 5.00 | 12.50 | 7.50 | 15.00 | | |
| Perfume | 0.10 | 0.10 | 0.10 | 0.10 | 0.10 | 0.10 | 0.10 |
| Isoalkane mixture from example 2 | 3.00 | 5.50 | 12.00 | 8.00 | 4.00 | 9.50 | 20.00 |
| D-Panthenol USP | 0.50 | 1.00 | 0.80 | 1.50 | 0.50 | | |
| Preservative | 0.10 | 0.10 | 0.10 | 0.10 | 0.10 | 0.10 | 0.10 |
| Citric acid | 0.10 | 0.10 | 0.10 | 0.10 | 0.10 | | |
| Rewopal LA 3 | 0.50 | 2.00 | 0.50 | 0.50 | 2.00 | | |
| Sodium chloride | 1.50 | 1.50 | 1.50 | 1.50 | 1.50 | | |
| Water dem. | ad 100 | ad 100 | ad 100 | ad 100 | ad 100 | ad 100 | ad 100 |

App. Ex. Application example

Application Examples 700-706 and Application Examples 707-713

Application examples 693-699 were repeated but using the isoalkane mixture from example 3 or from example 4, respectively, instead of the isoalkane mixture from example 2.

Application Examples 714-728

Aerosol Hair Spray

Application Example 714

VOC 80 Aerosol Hair Spray

| Additive | % |
|---|---|
| Isoalkane mixture from example 2 | 2.00 |
| Water | 18.00 |
| Dimethyl ether | 40.00 |
| Ethanol | 40.00 | further additive: silicone, perfume, antifoam etc.

Application example 715 and application example 716

Application example 714 was repeated but using the isoalkane mixture from example 3 or from example 4, respectively, instead of the isoalkane mixture from example 2.

Application Example 717

VOC 55 Aerosol Hair Spray

| Additive | % |
|---|---|
| Isoalkane mixture from example 2 | 2.00 |
| Water | 33.00 |
| Dimethyl ether | 40.00 |
| Ethanol | 25.00 | further additive: silicone, perfume, antifoam

Application Example 718 and Application Example 719

Application example 717 was repeated but using the isoalkane mixture from example 3 or from example 3, respectively, instead of the isoalkane mixture from example 4.

Application Example 720

VOC 55 Aerosol Hair Spray

| Additive | % |
|---|---|
| Isoalkane mixture from example 2 | 6.00 |
| Water | 39.00 |
| HFC 152A | 40.00 |
| Ethanol | 15.00 | further additive: silicone, perfume, antifoam, etc.

Application Example 721 and Application Example 722

Application example 720 was repeated, but using the isoalkane mixture from example 3 or from example 4, respectively, instead of the isoalkane mixture from example 2.

Application Example 723

VOC 55 Aerosol Hair Spray

| Additive | % |
|---|---|
| Isoalkane mixture from example 2 | 5.00 |
| Ultrahold Strong (BASF) | 1.00 |
| Water | 39.00 |
| Dimethyl ether | 40.00 |
| Ethanol | 15.00 |
| +AMP | to pH 8.3 | further additive: silicone, perfume, antifoam, etc.

Application Example 724 and Application Example 725

Application example 723 was repeated but using the isoalkane mixture from example 3 or from example 4, respectively, instead of the isoalkane mixture from example 2.

Application Example 726

VOC 55 Aerosol Hair Spray

| Additive | % |
|---|---|
| Isoalkane mixture from example 2 | 4.00 |
| Stepanhold R-1[*] (Stepan Chemical Co.) | 1.00 |
| Water | 40.00 |
| Dimethyl ether | 40.00 |
| Ethanol | 15.00 |
| + AMP | to pH 8.3 | further additive: silicone, perfume, antifoam, etc.
[*] Stepanhold R-1 = Poly(vinylpyrrolidone/ethyl methacrylate/methacrylic acid)

Application Example 727 and Application Example 728

Application example 726 was repeated but using the isoalkane mixture from example 3 or from example 4, respectively, instead of the isoalkane mixture from example 2.

Application Example 729

VOC 55 Hand Pump Spray

| Additive | % |
|---|---|
| Isoalkane mixture from example 2 | 4.00 |
| Water | 41.00 |
| Ethanol | 55.00 | further additive: silicone, perfume, antifoam, etc.

Application Example 730 and Application Example 731

Application example 729 was repeated but using the isoalkane mixture from example 3 or from example 4, respectively, instead of the isoalkane mixture from example 2.

Application Example 732

Aqueous Hand Pump Spray

| Additive | % |
|---|---|
| Isoalkane mixture from example 2 | 5.00 |
| Luviset Clear[*] (20% strength solution) | 5.00 |
| Water | 90.00 | further additive: water-soluble silicone, perfume, antifoam, etc.
[*] Luviset Clear: Poly(vinylpyrrolidone/methacrylamide/vinylimidazole), BASF

Application Example 733 and Application Example 734

Application example 732 was repeated but using the isoalkane mixture from example 3 or from example 4, respectively, instead of the isoalkane mixture from example 2.

Application example 735

Hair gel Containing Aculyn 28

| Additive | % |
| --- | --- |
| Phase 1: | |
| Isoalkane mixture from example 2 | 6.00 |
| Water, dist. | 43.00 |
| Aminomethylpropanol (38% strength solution) | 1.0 |
| Phase 2: | |
| Aculyn 28 (1% strength aqueous suspension) | 50.00 | further additive: preservative, soluble ethoxylated silicone, perfume, etc.

Preparation: Phases 1 and 2 were weighed separately and homogenized. Phase 2 was then slowly stirred into phase 1. An essentially clear, stable gel was formed.

Application Example 736 and Application Example 737

Application example 735 was repeated but using the isoalkane mixture from example 3 or from example 4, respectively, instead of the isoalkane mixture from example 2.

Application Examples 738-740

Hair Gel with Hydroxyethylcellulose

Application Example 738

| Additive | % |
| --- | --- |
| Phase 1: | |
| Isoalkane mixture from example 2 | 6.00 |
| Water, dist. | 36.00 |
| Phase 2: | |
| Natrosol HR 250 (5% strength solution) Hydroxyethylcellulose (Hercules) | 50.00 | further additive: preservative, soluble ethoxylated silicone, perfume, etc.

Preparation: Phases 1 and 2 were weighed separately and homogenized. Phase 2 was then slowly stirred into phase 1. An essentially clear, stable gel was formed.

Application Example 739 and Application Example 740

Application example 738 was repeated but using the isoalkane mixture from example 3 or from example 4, respectively, instead of the isoalkane mixture from example 2.

Application Examples 741-743

Liquid Make-Up

Application Example 741

| Additive | |
| --- | --- |
| Phase A | |
| Glyceryl stearate | 1.70 |
| Cetyl alcohol | 1.70 |
| Ceteareth-6 | 1.70 |
| Ceteareth-25 | 1.70 |
| Caprylic/capric triglyceride | 5.20 |
| Mineral oil | 5.20 |
| Phase B | |
| Preservative | q.s. |
| Propylene glycol | 4.30 |
| Isoalkane mixture from example 2 | 2.50 |
| Dist. water | 59.50 |
| Phase C | |
| Perfume oil | q.s. |
| Phase D | |
| Iron oxide | 2.00 |
| Titanium dioxide | 12.00 |

Preparation: Phase A and Phase B were heated separately from one another to 80° C. Phase B was then mixed into phase A with a stirrer. Everything was allowed to cool to 40° C. and then phase C and phase D were added. The mixture was homogenized a number of times.

Application Example 742 and Application Example 743

Application example 741 was repeated but using the isoalkane mixture from example 3 or from example 4, respectively, instead of the isoalkane mixture from example 2.

Application Examples 744-746

Oil-Free Make-Up

Application Example 744

| Phase A | |
| --- | --- |
| Veegum | 0.35 |
| Butylene glycol | 5.00 |
| Xanthan gum | 0.15 |

-continued

| Phase B | |
|---|---|
| Dist. water | 44.0 |
| Preservative | q.s. |
| Polysorbate-20 | 0.2 |
| Tetrahydroxypropylethylenediamine | 1.6 |
| Phase C | |
| Silicon dioxide | 1.0 |
| Nylon-12 | 2.0 |
| Mica | 4.15 |
| Titanium dioxide | 6.0 |
| Iron oxide | 1.85 |
| Phase D | |
| Stearic acid | 4.0 |
| Glyceryl stearate | 1.5 |
| Benzyl laurate | 7.0 |
| Isoeicosane | 5.0 |
| Preservative | q.s. |
| Phase E | |
| Panthenol | 0.5 |
| Imidazolidinylurea | 0.1 |
| Isoalkane mixture from example 2 | 15.0 |

Preparation: Phase A was wetted with butylene glycol, added to phase B and mixed thoroughly. The phase mixture of phase A and phase B was then heated to 75° C. The feed substances of phase C were pulverized and added to the mixture of phase A and B and carefully homogenized. The feed substances of phase D were mixed, heated to 80° C. and added to the mixture of phase A, phase B and phase C. Mixing was carried out until the mixture was homogeneous. The mixture was then transferred to a vessel with propeller mixer and the feed substances of phase E were mixed, which was then added to the mixture of phases A, B, C and D and thoroughly mixed.

Application Example 745 and Application Example 746

Application example 744 was repeated but using the isoalkane mixture from example 3 or from example 4, respectively, instead of the isoalkane mixture from example 2.

Application Examples 747-749

Face Mask

Application Example 747

| Phase A | |
|---|---|
| Ceteareth-6 | 3.00 |
| Ceteareth-25 | 1.50 |
| Cetearyl alcohol | 5.00 |
| Cetearyl octanoate | 6.00 |
| Mineral oil | 6.00 |
| Bisabolol | 0.20 |
| Glyceryl stearate | 3.00 |
| Phase B | |
| Propylene glycol | 2.00 |
| Panthenol | 5.00 |
| Isoalkane mixture from example 2 | 4.00 |
| Preservative | q.s. |
| Dist. water | 63.80 |

-continued

| Phase C | |
|---|---|
| Perfume | q.s. |
| Tocopheryl acetate | 0.50 |

Preparation: Phases A and B were heated separately to about 80° C. Phase B was then stirred into phase A with homogenization; after brief after-homogenization, the mixture was left to cool to about 40° C., phase C was added and homogenization was repeated. Application example 748 and application example 749: Application example 747 was repeated but using the isoalkane mixture from example 3 or from example 4, respectively, instead of the isoalkane mixture from example 2.

Application Examples 750-752

Face Lotion for Dry and Sensitive Skin

Application Example 750

| Phase A | |
|---|---|
| Hydrogenated castor oil PEG-40 | 2.50 |
| Perfume | q.s. |
| Bisabolol | 0.40 |
| Phase B | |
| Glycerol | 3.00 |
| Hydroxyethylcetyldimonium phosphate | 1.00 |
| Witch hazel (*Hamamelis Virginiana*) distillate | 5.00 |
| Panthenol | 0.50 |
| Isoalkane mixture from example 2 | 0.50 |
| Preservative | q.s. |
| Dist. water | 87.60 |

Preparation: Dissolve phase A until clear. Stir phase B into phase A.

Application Example 751 and Application Example 752

Application example 750 was repeated but using the isoalkane mixture from example 3 or from example 4, respectively, instead of the isoalkane mixture from example 2.

Application Examples 753-755

Face Washing Paste with Peeling Effect

Application Example 753

| Phase A | |
|---|---|
| Dist. water | 58.00 |
| Isoalkane mixture from example 2 | 15.00 |
| Carbomer | 1.50 |
| Preservative | q.s. |
| Phase B | |
| Perfume | q.s. |
| Potassium cocoyl hydrolyzed protein | 7.00 |
| Cocamidpropylbetaine | 4.00 |

-continued

| Phase C | |
| --- | --- |
| Triethanolamine | 1.50 |
| Phase D | |
| Polyethylene (Luwax ATM from BASF) | 13.00 |

Preparation: Phase A was allowed to swell. Phase B was then dissolved, forming a clear solution. Phase B was stirred into phase A and neutralized with phase C. Phase D was then stirred in.

Application Example 754 and Application Example 755

Application example 753 was repeated but using the isoalkane mixture from example 3 or from example 4, respectively, instead of the isoalkane mixture from example 2.

Application Examples 756-758

Peeling Cream, O/W Type

Application Example 756

| Phase A | |
| --- | --- |
| Ceteareth-6 | 3.00 |
| Ceteareth-25 | 1.50 |
| Glyceryl stearate | 3.00 |
| Cetearyl alcohol, sodium cetearyl sulfate | 5.00 |
| Cetearyl octanoate | 6.00 |
| Mineral oil | 6.00 |
| Bisabolol | 0.20 |
| Phase B | |
| Propylene glycol | 2.00 |
| Disodium EDTA | 0.10 |
| Isoalkane mixture from example 2 | 3.00 |
| Preservative | q.s. |
| Dist. water | 59.70 |
| Phase C | |
| Tocopheryl acetate | 0.50 |
| Perfume | q.s. |
| Phase D | |
| Polyethylene | 10.00 |

Preparation: Phases A and B were heated separately to about 80° C. Phase B was then stirred into phase A and homogenized. The mixture was left to cool to about 40° C., phase C was added and homogenization was repeated briefly. Phase D was then stirred in.

Application Example 757 and Application Example 758

Application example 756 was repeated but using the isoalkane mixture from example 3 or from example 4, respectively, instead of the isoalkane mixture from example 2.

Application Examples 759-761

Shaving Foam

Application Example 759

| Ceteareth-25 | 6.00 |
| --- | --- |
| Poloxamer 407 | 5.00 |
| Dist. water | 52.00 |
| Triethanolamine | 1.00 |
| Propylene glycol | 5.00 |
| Lanolin oil PEG-75 | 1.00 |
| Isoalkane mixture from example 2 | 5.00 |
| Preservative | q.s. |
| Perfume | q.s. |
| Sodium laureth sulfate | 25.00 |

Preparation: All of the components were weighed together and the mixture was stirred until everything had dissolved. Bottling: 90 parts of active substance and 10 parts of 25:75 propane/butane mixture.

Application Example 760 and Application Example 761

Application example 759 was repeated but using the isoalkane mixture from example 3 or from example 4, respectively, instead of the isoalkane mixture from example 2.

Application Example 762-764

After Shave Balsam

Application Example 762

| Phase A | |
| --- | --- |
| Acrylate/$C_{10-30}$ alkyl acrylate copolymer | 0.25 |
| Tocopheryl acetate | 1.50 |
| Bisabolol | 0.20 |
| Caprylic/capric triglyceride | 10.00 |
| Perfume | q.s. |
| Hydrogenated castor oil PEG-40 | 1.00 |
| Phase B | |
| Panthenol | 1.00 |
| Alcohol | 15.00 |
| Glycerol | 5.00 |
| Hydroxyethylcellulose | 0.05 |
| Isoalkane mixture from example 2 | 1.92 |
| Dist. water | 64.00 |
| Phase C | |
| Sodium hydroxide | 0.08 |

Preparation: The components of phase A are mixed. Phase B was then stirred into phase A with homogenization and the mixture was briefly after-homogenized. The mixture was neutralized with phase C and homogenized again.

Application Example 763 and Application Example 764

Application example 762 was repeated but using the isoalkane mixture from example 3 or from example 4, respectively, instead of the isoalkane mixture from example 2.

Application Examples 765-767

Toothpaste

Application Example 765

| | |
|---|---|
| Phase A | |
| Dist. water | 34.79 |
| Isoalkane mixture from example 2 | 3.00 |
| Preservative | 0.30 |
| Glycerol | 20.00 |
| Sodium monofluorophosphate | 0.76 |
| Phase B | |
| Sodium carboxymethylcellulose | 1.20 |
| Phase C | |
| Aroma oil | 0.80 |
| Saccharin | 0.06 |
| Preservative | 0.10 |
| Bisabolol | 0.05 |
| Panthenol | 1.00 |
| Tocopheryl acetate | 0.50 |
| Silicon dioxide | 2.80 |
| Sodium lauryl sulfate | 1.00 |
| Dicalcium phosphate, anhydrous | 7.90 |
| Dicalcium phosphate dihydrate | 25.29 |
| Titanium dioxide | 0.45 |

Preparation: Phase A was dissolved. Phase B was then sprinkled into phase A and dissolved. Phase C was added and left under reduced pressure at room temperature for about 45 minutes.

Application Example 766 and Application Example 767

Application example 765 was repeated but using the isoalkane mixture from example 3 or from example 4, respectively, instead of the isoalkane mixture from example 2.

Application Examples 768-770

Mouthwash

Application example 768

| | |
|---|---|
| Phase A | |
| Aroma oil | 2.00 |
| Hydrogenated castor oil PEG-40 | 4.00 |
| Bisabolol | 1.00 |
| Alcohol | 30.00 |
| Phase B | |
| Saccharin | 0.20 |
| Glycerol | 5.00 |
| Preservative | q.s. |
| Poloxamer 407 | 5.00 |
| Isoalkane mixture from example 2 | 2.5 |
| Dist. water | 50.30 |

Preparation: Phases A and B were dissolved separately until clear. Phase B was stirred into phase A.

Application Example 769 and Application Example 770

Application example 768 was repeated but using the isoalkane mixture from example 3 or from example 4, respectively, instead of the isoalkane mixture from example 2.

Application Examples 771-773

Prosthesis Adhesive

Application Example 771

| | |
|---|---|
| Phase A | |
| Bisabolol | 0.20 |
| Betacarotene | 1.00 |
| Aroma oil | q.s. |
| Cetearyl octanoate | 20.00 |
| Silicon dioxide | 5.00 |
| Mineral oil | 33.80 |
| Phase B | |
| Isoalkane mixture from example 2 | 5.00 |
| PVP (20% strength solution in water) | 35.00 |

Preparation: Phase A was mixed thoroughly. Phase B was then stirred into phase A.

Application Example 772 and Application Example 773

Application example 771 was repeated, but using the isoalkane mixture from example 3 or from example 4, respectively, instead of the isoalkane mixture from example 2.

Application Examples 774-776

Lip Care Cream

Application example 774

| | |
|---|---|
| Phase A | |
| Cetearyl octanoate | 10.00 |
| Polybutene | 5.00 |
| Phase B | |
| Carbomer | 0.10 |
| Phase C | |
| Ceteareth-6 | 2.00 |
| Ceteareth-25 | 2.00 |
| Glyceryl stearate | 2.00 |
| Cetyl alcohol | 2.00 |
| Dimethicone | 1.00 |
| Benzophenone-3 | 1.00 |

-continued

| | |
|---|---|
| Bisabolol | 0.20 |
| Mineral oil | 6.00 |
| Phase D | |
| Isoalkane mixture from example 2 | 8.00 |
| Panthenol | 3.00 |
| Propylene glycol | 3.00 |
| Preservative | q.s. |
| Dist. water | 54.00 |
| Phase E | |
| Triethanolamine | 0.10 |
| Phase F | |
| Tocopheryl acetate | 0.50 |
| Tocopherol | 0.10 |
| Perfume | q.s. |

Preparation: Phase A was dissolved until clear. Phase B was added thereto and homogenized. The components of phase C were added and melted at 80° C. Phase D was heated to 80° C. Phase D was added to the mixture of phases A, B and C and homogenized. The mixture was left to cool to about 40° C., phase E and phase F were added and homogenization was carried out again.

Application Example 775 and Application Example 776

Application example 774 was repeated but using the isoalkane mixture from example 3 or from example 4, respectively, instead of the isoalkane mixture from example 2.

Application Examples 777-779

Refreshing Gel

Application Example 777

| | |
|---|---|
| Phase A | |
| Carbomer | 0.60 |
| Dist. water | 45.40 |
| Phase B | |
| Bisabolol | 0.50 |
| Farnesol | 0.50 |
| Perfume | q.s. |
| PEG-40 hydrogenated castor oil | 5.00 |
| Isoalkane mixture from example 2 | 2.50 |
| Tetrahydroxypropylethylenediamine | 1.00 |
| Menthol | 1.50 |
| Alcohol | 43.00 |
| C.I. 74 180, Direct Blue 86 | q.s. |

Preparation: Phase A was left to swell, phase B was dissolved and phase B was stirred into phase A.

Application Example 778 and Application Example 779

Application example 777 was repeated but using the isoalkane mixture from example 3 or from example 4, respectively, instead of the isoalkane mixture from example 2.

Application Examples 780-782

Roll-On Antiperspirant

Application Example 780

| | |
|---|---|
| Phase A | |
| Hydroxyethylcellulose | 0.40 |
| Dist. water | 50.00 |
| Phase B | |
| Alcohol | 25.00 |
| Bisabolol | 0.10 |
| Farnesol | 0.30 |
| PEG-40 hydrogenated castor oil | 2.00 |
| Perfume | q.s. |
| Phase C | |
| Aluminum chlorohydrate | 5.00 |
| Propylene glycol | 3.00 |
| Dimethicone copolyol | 3.00 |
| Polyquaternium-16 | 3.00 |
| Isoalkane mixture from example 2 | 6.00 |
| Dist. water | 2.20 |

Preparation: Phase A was left to swell; phases B and C were then in each case dissolved separately. Phase A and B were stirred into phase C.

Application Example 781 and Application Example 782

Application example 780 was repeated but using the isoalkane mixture from example 3 or from example 4, respectively, instead of the isoalkane mixture from example 2.

Application Examples 783-785

Transparent Deodorant Stick

Application example 783

| | |
|---|---|
| Sodium stearate | 5.00 |
| Triclosan | 0.50 |
| Ceteareth-25 | 3.00 |
| Glycerol | 20.00 |
| Isoalkane mixture from example 2 | 2.50 |
| Perfume | q.s. |
| Propylene glycol | 60.00 |
| Bisabolol | 0.20 |
| Dist. water | 10.80 |

Preparation: Phase A was weighed in together, melted and homogenized. The mixture was then poured into a mold.

Application Example 784 and Application Example 785

Application example 783 was repeated but using the isoalkane mixture from example 3 or from example 4, respectively, instead of the isoalkane mixture from example 2.

Application Examples 786-787

Daycare Aerosol

Application Example 786

| Phase A | |
|---|---|
| Ethylhexyl methoxycinnamate | 4.00 |
| Octocrylene | 1.50 |
| Caprylic/capric triglyceride | 9.00 |
| *Simmondsia Chinensis* (jojoba) seed oil | 5.00 |
| Cyclomethicone | 1.50 |
| Hydrogenated coco glycerides | 3.00 |
| PVP/Hexadecene copolymer | 1.00 |
| Ceteareth-6, stearyl alcohol | 1.00 |
| Phase B | |
| Zinc oxide | 5.00 |
| Phase C | |
| Ceteareth-25 | 2.00 |
| Panthenol | 1.20 |
| Sodium ascorbyl phosphate | 0.20 |
| Imidazolidinylurea | 0.30 |
| Disodium EDTA | 0.10 |
| Isoalkane mixture from example 2 | 7.50 |
| Dist. water | 56.67 |
| Phase D | |
| Tocopheryl acetate | 0.50 |
| Bisabolol | 0.20 |
| Caprylic/capric triglyceride, retinol | 0.33 |
| Perfume | q.s. |

Preparation: Phase A was heated to 80° C. Phase A was dissolved until clear. Phase B was worked in and homogenized. Phase C was then added, heated to 80° C., melted and homogenized. With stirring, the mixture was left to cool to about 40° C., phase D was added and the mixture was homogenized briefly. Bottle 90% active ingredient solution: 10% propane/butane at 3.5 bar (20° C.).

Application Example 787 and Application Example 788

Application example 786 was repeated but using the isoalkane mixture from example 3 or from example 4, respectively, instead of the isoalkane mixture from example 2.

Application Examples 789-791

Pump Mousse

Application Example 789

| Phase A | |
|---|---|
| Cocotrimonium methosulfate | 2.00 |
| Perfume | q.s. |

-continued

| Phase B | |
|---|---|
| Dist. water | 84.30 |
| Polyquaternium-46 (10% strength aqueous solution) | 7.00 |
| Isoalkane mixture from example 2 | 5.00 |
| PEG-8 | 0.50 |
| Panthenol | 1.00 |
| Preservative | q.s. |
| PEG-25 PABA (ethoxylated p-aminobenzoic acid) | 0.20 |

Preparation: The components of phase A were mixed. The components of phase B were added one after the other, and a clear solution was formed.

Application Example 790 and Application Example 791

Application example 789 was repeated but using the isoalkane mixture from example 3 or from example 4, respectively, instead of the isoalkane mixture from example 2.

Application Examples 792-794

Aerosol Foam

Application Example 792

| | |
|---|---|
| Isoalkane mixture from example 2 | 15.00 |
| PVP/VA copolymer (40% strength aqueous solution) | 5.00 |
| Hydroxyethylcetyldimonium phosphate | 0.50 |
| Ceteareth-25 | 0.20 |
| Perfume PC 910.781/cremophor | 0.40 |
| Dist. water | 68.90 |
| Preservative | q.s. |
| Propane/butane 3.5 bar (20° C.) | 10.00 |

Preparation: Everything was weighed in together, stirred until everything had dissolved and bottled.

Application Example 793 and Application Example 794

Application example 792 was repeated but using the isoalkane mixture from example 3 or from example 4, respectively, instead of the isoalkane mixture from example 2.

Application Examples 795-797

Color Styling Mousse

Application example 795

| Phase A | |
|---|---|
| Cocotrimonium methosulfate | 2.00 |
| Perfume | q.s. |
| Phase B | |
| Isoalkane mixture from example 2 | 23.50 |
| Acrylate copolymer (Luvimer 100 P ®, BASF) | 0.50 |
| Aminomethylpropanol | 0.10 |
| Ceteareth-25 | 0.20 |
| Panthenol | 0.20 |
| Hydroxyethylcellulose | 0.20 |
| Alcohol | 10.00 |

-continued

| | |
|---|---|
| Dist. water | 53.17 |
| C.I. 12245, Basic Red 76 | 0.08 |
| C.I. 42510, Basic Violet 14 | 0.05 |
| Phase C | |
| Propane/butane 3.5 bar (20° C.) | 10.00 |

Preparation: Everything was weighed in together, stirred until everything had dissolved and then bottled. This color styling mouse is suitable for dark blonde and brown hair.

Application Example 796 and Application Example 797

Application example 795 was repeated but using the isoalkane mixture from example 3 or from example 4, respectively, instead of the isoalkane mixture from example 2.

Application Examples 798-800

Dark Brown Permanent Hair Color (Oxidation Hair Color)

Application Example 798

| | |
|---|---|
| Phase A | |
| Dist. water | 46.90 |
| Sodium sulfite | 0.20 |
| Disodium EDTA | 0.05 |
| p-Phenylenediamine | 0.20 |
| Resorcinol | 0.30 |
| 4-Amino-2-hydroxytoluene | 0.20 |
| m-Aminophenol | 0.10 |
| Oleyl alcohol | 1.50 |
| Propylene glycol | 4.50 |
| Sodium $C_{12-15}$ Pareth-15 sulfonate | 2.30 |
| Oleic acid | 20.00 |
| Phase B | |
| Isoalkane mixture from example 2 | 5.00 |
| Ammonium hydroxide | 13.70 |
| Isopropanol | 6.00 |
| Perfume | q.s. |

Preparation: Phase A was solubilized. The components of phase B were added one after the other and mixed.

Application Example 799 and Application Example 800

Application example 798 was repeated but using the isoalkane mixture from example 3 or from example 4, respectively, instead of the isoalkane mixture from example 2.

Application Examples 801-803

Pale Brown Semipermanent Hair Color

Application Example 801

| | |
|---|---|
| Cocodiethanolamide | 10.00 |
| Sodium dodecylbenzylsulfonate, 50% strength | 4.00 |
| Isoalkane mixture from example 2 | 5.00 |
| $C_{9-11}$ Pareth-3 | 6.00 |

-continued

| | |
|---|---|
| Sodium lauryl sulfate | 2.50 |
| 2-Nitro-p-phenylenediamine | 0.40 |
| HC Red No. 3 | 0.20 |
| HC Yellow No. 2 | 0.20 |
| dist. water | 71.70 |

Preparation: The components were added one after the other and mixed.

Application Example 802 and Application Example 803

Application example 801 was repeated but using the isoalkane mixture from example 3 or from example 4, respectively, instead of the isoalkane mixture from example 2.

Application Examples 804-806

Setting Solution

Application Example 804

| Additive | % by wt. |
|---|---|
| Isoalkane mixture from example 2 | 18.00 |
| Ethanol | 82.00 | further additive: silicone, perfume, antifoam, etc.

Application Example 805 and Application Example 806

Application example 804 was repeated but using the isoalkane mixture from example 3 or from example 4, respectively, instead of the isoalkane mixture from example 2.

The invention claimed is:

1. An isoalkane mixture whose $^1$H NMR spectrum in the region of a chemical shift δ of from 0.6 to 1.0 ppm, based on tetramethylsilane, has a surface integral of from 25 to 70%, based on the total integral surface,
   wherein a fraction of side chains having two or more carbon atoms, from among all side chains of the longest continuous carbon chain of the isoalkane molecules in the isoalkane mixture, is less than 20%,
   wherein the isoalkane mixture comprises at least 70% by weight of alkanes having 8 to 20 carbon atoms, and
   wherein the isoalkane mixture is obtained by a method in which
   a) a $C_4$ hydrocarbon mixture is provided, which comprises less than 3% by weight of isobutene,
   b) the $C_4$ hydrocarbon mixture is subjected to an oligomerization over a transition-metal-containing catalyst, and
   c) the oligomerization product obtained in step b) is completely hydrogenated;
   wherein the oligomerization product obtained in step b) and/or the hydrogenation product obtained in step c) is subjected to a separation, wherein a fraction enriched in $C_{16}$-oligomers is obtained.

2. The isoalkane mixture according to claim 1, whose $^1$H NMR spectrum in the region of a chemical shift δ of from 0.6 to 1.0 ppm, has a surface integral of from 30 to 60% based on the total integral surface.

3. The isoalkane mixture according to claim 1, which has a degree of branching B in the range from 0.1 to 0.35.

4. The isoalkane mixture according to claim 1, which essentially has no tert-butyl groups.

5. The isoalkane mixture according to claim 1, which comprises at least 70% by weight of alkanes having 12 to 20 carbon atoms.

6. The isoalkane mixture according to claim 1, which consists essentially of alkanes having 8 or 12 or 16 carbon atoms.

7. The isoalkane mixture according to claim 1, which, based on its total weight, comprises less than 95% by weight of alkanes of the same molecular weight.

8. The isoalkane mixture according to claim 1, which has a spreading value of at least 130% based on Paraffinum perliquidum.

9. The isoalkane mixture according to claim 1, which has a viscosity, determined in accordance with Brookfield, in the range from 2 to 10 mPas.

10. The isoalkane mixture according to claim 1, which has a kinematic viscosity in the range from 5 to 25 cSt.

11. The isoalkane mixture according to claim 1, which has a density in the range from 0.7 to 0.82 g/cm$^3$.

12. The isoalkane mixture according to claim 1, which has a refractive index in the range from 1.4 to 1.5.

13. The isoalkane mixture according to claim 1, where the catalyst used in step b) is a heterogeneous catalyst comprising nickel.

14. The isoalkane mixture according to claim 1, obtainable by a method in which the hydrogenated oligomerization product obtained in step c) is subjected to a work-up by bringing it into contact with at least one adsorbent.

15. The isoalkane mixture according to claim 1, wherein the fraction of side chains having two or more carbon atoms is at most 10%.

16. The isoalkane mixture according to claim 1, wherein the fraction of side chains having two or more carbon atoms is at most 5%.

17. The isoalkane mixture according to claim 1, wherein the fraction of side chains having two or more carbon atoms is at most 1%.

18. The isoalkane mixture according to claim 1; wherein the isoalkane mixture has a $^1$H NMR spectrum in the region of a chemical shift δ of from 0.6 to 1.0 ppm, has a surface integral of from 30 to 60% based on the total integral surface; wherein the isoalkane mixture which has a degree of branching B in the range from 0.1 to 0.35; wherein the isoalkane mixture essentially has no test-butyl groups; and wherein the isoalkane mixture, based on its total weight, comprises less than 95% by weight of alkanes of the same molecular weight.

19. The isoalkane mixture according to claim 1, wherein the oligomerization product obtained in step b) consists of 7% $C_{12}$ oligomerization products, 70% $C_{16}$ oligomerization products, 17% $C_{20}$ oligomerization products, and higher homologues.

20. A cosmetic or pharmaceutical composition comprising at least one isoalkane mixture according to claim 1, which has at least 95% by weight of alkanes of the same molecular weight.

21. The composition according to claim 20, comprising a mixture having $C_{16}$-isoalkanes and having a composition in which the molecules present comprise, on average, fewer than 1.0 quaternary carbon atoms per molecule, where the mixture has a fraction of $C_{16}$-alkanes of ≥95% by mass and where the mixture has a fraction of less than 5% by mass of n-hexadecane.

22. The composition according to claim 20, comprising a mixture having $C_{16}$-isoalkanes, obtainable by a method where
 a) a butene-containing $C_4$-hydrocarbon stream which has less than 5% by mass, based on the total of all butenes, of isobutene, is oligomerized in the presence of a nickel-containing catalyst,
 b) a $C_{16}$-olefin fraction is separated off from the reaction mixture and
 c) the $C_{16}$ fraction is hydrogenated.

23. The composition according to claim 20, comprising
 A) at least one isoalkane mixture having $C_{16}$-isoalkanes,
 B) at least one cosmetically or pharmaceutically acceptable active ingredient or effect substance,
 C) if appropriate at least one further cosmetically or pharmaceutically acceptable auxiliary different from B).

24. The composition according to claim 20 in the form of an ointment, cream, emulsion, suspension, lotion, milk, paste, gel, foam or spray.

25. The composition according to claim 23 comprising component A) in a fraction of from 0.01 to 99.9% by weight, based on the total weight of the composition.

26. The composition according to claim 23, where components B) and C) are selected from carriers, excipients, emulsifiers, surfactants, preservatives, fragrances, perfume oils, thickeners, polymers, gel formers, dyes, pigments, photoprotective agents, consistency regulators, antioxidants, antifoams, antistats, resins, solvents, solubility promoters, neutralizing agents, stabilizers, sterilizing agents, propellants, drying agents, opacifiers, cosmetically active ingredients, hair polymers, hair and skin conditioners, graft polymers, water-soluble or dispersible silicone-containing polymers, bleaches, care agents, colorants, tinting agents, tanning agents, humectants, refatting agents, collagen, protein hydrolyzates, lipids, emollients and softeners, and mixtures thereof.

27. The composition according to claim 23, comprising, as active ingredient or effect substance B) or auxiliary C), at least one copolymer Ca) which is obtainable by copolymerization of
 (A) at least one ethylenically unsaturated dicarboxylic anhydride derived from at least one dicarboxylic acid having 4 to 8 carbon atoms,
 (B) at least one oligomer of branched or unbranched $C_3$-$C_{10}$-alkene, where at least one oligomer has an average molecular weight $M_n$ in the range from 300 to 5000 g/mol, preferably up to 1200 g/mol, or is obtainable by oligomerization of at least 3 equivalents of $C_3$-$C_{10}$-alkene,
 (C) optionally at least one α-olefin having up to 24 carbon atoms,
 (D) optionally at least one further ethylenically unsaturated comonomer different from (A), (B) and (C), if appropriate reaction with
 (E) at least one compound of the general formula Ia, Ib, Ic or Id

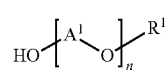

Ia

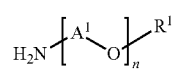

Ib

-continued

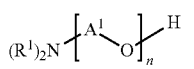

Ic

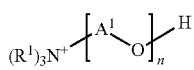

Id where

A$^1$ C$_2$-C$_{20}$-alkylene, identical or different,

R$^1$ C$_1$-C$_{30}$-alkyl, linear or branched, phenyl or hydrogen, n an integer from 1 to 200 and if appropriate subsequent contacting with water, where the copolymer Ca) is, if appropriate, mixed with at least one additional oligomer Z) of branched or unbranched C$_3$-C$_{10}$-alkene, where at least one oligomer Z) has an average molecular weight M$_n$ in the range from 300 to 5000 g/mol, or is obtainable by oligomerization of at least 3 equivalents of C$_3$-C$_{10}$-alkene, where the copolymer component B) and/or the oligomer Z) comprises an isoalkane mixture whose $^1$H NMR spectrum in the region of a chemical shift δ of from 0.6 to 1.0 ppm, based on tetramethylsilane, has a surface integral of from 25 to 70%, based on the total integral surface, or consists of such an isoalkane mixture.

28. A cosmetic or pharmaceutical composition comprising

A) at least one isoalkane mixture as defined in claim 1,

B) at least one cosmetically or pharmaceutically acceptable active ingredient or effect substance, C) if appropriate at least one further cosmetically or pharmaceutically acceptable auxiliary different from B).

29. A hair cosmetic composition comprising
   a) 0.05 to 20% by weight of at least one hair polymer,
   b) 20 to 99.95% by weight of a carrier comprising at least one isoalkane mixture as defined in claim 1, which has at least 95% by weight of alkanes of the same molecular weight,
   c) 0 to 50% by weight of at least one propellant gas,
   d) 0 to 5% by weight of at least one emulsifier,
   e) 0 to 3% by weight of at least one thickener, and
   f) up to 25% by weight of further constituents.

30. A method for the preparation of the isoalkane mixture according to claim 1 in which
   a) a C$_4$ hydrocarbon feed material is provided which comprises less than 3% by weight of isobutene,
   b) the feed material is subjected to an oligomerization over a transition-metal-containing catalyst,
   c) the oligomerization product obtained in step b) is completely hydrogenated;
   wherein the oligomerization product obtained in step b) and/or the hydrogenation product obtained in step c) is subjected to a separation, wherein a fraction enriched in C$_{16}$-oligomers is obtained.

31. The method of preparing of an isoalkane mixture as defined in claim 1 as or in the hydrophobic component of a homogeneous-phase or heterogeneous-phase cosmetic or pharmaceutical composition.

32. The method of preparing of an isoalkane mixture as defined in claim 1 in compositions for the care and protection of the skin, skin-cleansing compositions, preparations for decorative cosmetics, in hair-treatment compositions, for moisturizing the skin, for conditioning skin or hair, for modifying rheological properties, for improving skin compatibility and/or for generating better wetting.

33. The method of preparing of an isoalkane mixture as defined in claim 1 as heat-transfer liquid, solvent for fuel additives, low-temperature fuel or shock absorber oil.

* * * * *